(12) United States Patent
Karumanchi et al.

(10) Patent No.: US 7,435,419 B2
(45) Date of Patent: Oct. 14, 2008

(54) METHODS OF DIAGNOSING AND TREATING PRE-ECLAMPSIA OR ECLAMPSIA

(75) Inventors: S. Ananth Karumanchi, West Roxbury, MA (US); Vikas P. Sukhatme, Newton, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 11/019,559

(22) Filed: Dec. 21, 2004

(65) Prior Publication Data

US 2005/0170444 A1      Aug. 4, 2005

Related U.S. Application Data

(63) Continuation-in-part of application No. 10/771,518, filed on Feb. 4, 2004, now Pat. No. 7,335,362, which is a continuation-in-part of application No. 10/624,809, filed on Jul. 21, 2003.

(60) Provisional application No. 60/467,390, filed on May 2, 2003, provisional application No. 60/451,796, filed on Mar. 3, 2003, provisional application No. 60/397,481, filed on Jul. 19, 2002.

(51) Int. Cl.
*A61K 38/00* (2006.01)
*A61K 39/00* (2006.01)
*G01N 33/53* (2006.01)
*C07K 17/00* (2006.01)

(52) U.S. Cl. .................. 424/198.1; 435/7.1; 435/7.2; 514/2; 514/12; 530/350

(58) Field of Classification Search .......... None
See application file for complete search history.

(56) References Cited

U.S. PATENT DOCUMENTS

| | | | |
|---|---|---|---|
| 5,194,596 | A | 3/1993 | Tischer et al. |
| 5,219,739 | A | 6/1993 | Tischer et al. |
| 5,238,819 | A | 8/1993 | Roberts et al. |
| 5,240,848 | A | 8/1993 | Keck et al. |
| 5,332,671 | A | 7/1994 | Ferrara et al. |
| 5,543,138 | A | 8/1996 | Keith |
| 5,712,395 | A | 1/1998 | App et al. |
| 5,763,441 | A | 6/1998 | App et al. |
| 5,830,879 | A | 11/1998 | Isner |
| 5,958,715 | A | 9/1999 | Muller |
| 6,100,071 | A | 8/2000 | Davis-Smyth et al. |
| 6,258,787 | B1 | 7/2001 | Isner |
| 6,365,157 | B2 | 4/2002 | Rockwell et al. |
| 6,399,585 | B1 | 6/2002 | Larson et al. |
| 6,410,322 | B1 | 6/2002 | Robinson |
| 6,447,768 | B1 | 9/2002 | Van Zonneveld et al. |
| 6,660,534 | B2 | 12/2003 | McVicker et al. |
| 6,677,300 | B1 | 1/2004 | Schreiner et al. |
| 2003/0114412 | A1 | 6/2003 | Ward et al. |
| 2003/0144298 | A1 | 7/2003 | Curwen et al. |
| 2003/0220262 | A1 | 11/2003 | Schreiner et al. |
| 2004/0038305 | A1 | 2/2004 | Poston et al. |
| 2004/0126828 | A1 | 7/2004 | Karumanchi et al. |
| 2005/0025762 | A1 | 2/2005 | Karumanchi et al. |
| 2005/0148023 | A1 | 7/2005 | Thadhani et al. |
| 2005/0148040 | A1 | 7/2005 | Thadhani et al. |
| 2006/0183175 | A1* | 8/2006 | Buhimschi et al. ......... 435/7.92 |

FOREIGN PATENT DOCUMENTS

| | | |
|---|---|---|
| EP | 1 417 971 | 5/2004 |
| WO | WO 98/28006 | 7/1998 |
| WO | WO 02/37120 | 5/2002 |
| WO | WO 2006/069373 | 6/2006 |

OTHER PUBLICATIONS

Ferrara, N. Role of vascular endothelial growth factor in the regulation of angiogenesis, (1999) Kidney International, vol. 56, pp. 794-814.*
Carmeliet et al., Synergism between vascular endothelial growth factor and placental growth factor contributes to angiogenesis and plasma extravasation in pathological conditions, (2001) Nature Medicine, vol. 7, No. 5, pp. 575-583.*
Torry et al., Expression and function of Placenta Growth Factor: Implications for abnormal placentation, 2003, Journal of Society Gynecology Investigation, vol 10, pp. 178-188.*
Helske et al., "Expression of Vascular Endothelial Growth Factor Receptors 1, 2 and 3 in Placentas From Normal and Complicated Pregnancies," *Mol. Hum. Reprod.* 7: 205-210 (2001).
Levine et al., "Urinary Placental Growth Factor and Risk of Preeclampsia," *JAMA* 293: 77-85 (2005).
Livingston et al., "Placenta Growth Factor is not an Early Marker for the Development of Severe Preeclampsia," *Am. J. Obstet. Gynecol.* 184: 1218-1220 (2001).
Livingston et al., "Reductions of Vascular Endothelial Growth Factor and Placental Growth Factor Concentrations in Severe Preeclampsia," *Am. J. Obstet. Gynecol.* 183: 1554-1557 (2000).
International Search Report Application No. PCT/US05/03884.
International Search Report Application No. PCT/US03/22892.
Foreign Search Report Application No. SG 200500265-4.
Ahmed et al., "Regulation of Placental Vascular Endothelial Growth Factor (VEGF) and Placenta Growth Factor (PlGF) and Soluble Flt-1 by Oxygen—A Review," *Placenta* 21:S16-S24 (2000).
Baek et al., "Hypoxia-Induced VEGF Enhances Tumor Survivability Via Suppression of Serum Deprivation-Induced Apoptosis," *Oncogene* 19:4621-4631 (2000).

(Continued)

*Primary Examiner*—Manjunath Rao
*Assistant Examiner*—Ian Dang
(74) *Attorney, Agent, or Firm*—Kristina Bieker-Brady; Clark & Elbing LLP

(57) ABSTRACT

Disclosed herein are methods for diagnosing pre-eclampsia and eclampsia or a propensity to develop pre-eclampsia or eclampsia by detecting the levels of placental growth factor in a subject.

56 Claims, 18 Drawing Sheets

OTHER PUBLICATIONS

Barleon et al., "Soluble VEGFR-1 Secreted by Endothelial Cells and Monocytes is Present in Human Serum and Plasma from Healthy Donors," *Angiogenesis* 4:143-154 (2001).

Baumgartner et al., "Constitutive Expression of phVEGF$_{165}$ After Intramuscular Gene Transfer Promotes Collateral Vessel Development in Patients with Critical Limb Ischemia," *Circulation* 97:1114-1123 (1998).

Belgore et al., "Measurement of Free and Complexed Soluble Vascular Endothelial Growth Factor Receptor, Fit-1, in Fluid Samples: Development and Application of Two New Immunoassays," *Clin. Sci.* 100:567-575 (2001).

Belgore et al., "Plasma Levels of Vascular Endothelial Growth Factor and Its Soluble Receptor (SFit-1) in Essential Hypertension," *Am. J. Cardiol.* 87:805-807 (2001).

Belgore et al., "sFit-1, a Potential Antagonist for Exogenous VEGF," *Circulation* 102:E108-E109 (2000).

Belgore et al., "Successful Therapy Reduces Levels of Vascular Endothelial Growth Factor (VEGF) in Patients with Hypertension and Patients with Hypercholesterolemia," *Atherosclerosis* 151:599 (2000).

Belgore et al., "Vascular Endothelial Growth Factor and its Receptor, Fit-1, in Smokers and Non-Smokers," *Br. J. Biomed. Sci.* 57:207-213 (2000).

Blann et al., "Plasma Vascular Endothelial Growth Factor and Its Receptor Fit-1 in Patients with Hyperlipidemia and Atherosclerosis and the Effects of Fluvastatin or Fenofibrate," *Am. J. Cardiol.* 87:1160-1163 (2001).

Brown et al., "Vascular Permeability Factor mRNA and Protein Expression in Human Kidney," *Kidney Int.* 42:1457-1461 (1992).

Bouletreau et al., "Hypoxia and VEGF Up-Regulate BMP-2 mRNA and Protein Expression In Microvascular Endothelial Cells: Implications for Fracture Healing," *Plast. Reconstr. Surg.* 109:2384-2397 (2002).

Celletti et al., "Effect of Human Recombinant Vascular Endothelial Growth Factor165 on Progression of Atherosclerotic Plaque," *J. Am. Coll. Cardiol.* 37:2126-2130 (2001).

Charnock-Jones et al., Determination of the Circulating Levels of the Soluble Form of the VEGF-R1 (sFlt-1) in Women at High Risk of Developing Pre-Eclampsia, *J. Soc. Gynecol. Investig.* 10:166A Abstract No. 230 (2003).

Chamock-Jones et al., "Identification and Localization of Alternately Spliced mRNAs for Vascular Endothelial Growth Factor in Human Uterus and Estrogen Regulation in Endometrial Carcinoma Cell Lines," *Biol. Reprod.* 48:1120-1128 (1993).

Clark et al., "A Vascular Endothelial Growth Factor Antagonist is Produced by the Human Placenta and Released into the Maternal Circulation," *Biol. Reprod.* 59:1540-1548 (1998).

Cockell et al., "Human Placental Syncytiotrophoblast Microvillous Membranes Impair Maternal Vascular Endothelial Function," *Br. J. Obstet. Gynaecol.* 104:235-240 (1997).

Cohen et al., "Amelioration of Diabetic Nephropathy by Treatment with Monoclonal Antibodies Against Glycated Albumin," *Kidney Int.* 45:1673-1679 (1994).

Deodato et al., "Recombinant AAV Vector Encoding Human VEGF165 Enhances Wound Healing," *Gene Ther.* 9:777-785 (2002).

Eddahibi et al., "Imbalance Between Platelet Vascular Endothelial Growth Factor and Platelet-Derived Growth Factor in Pulmonary Hypertension," *Am. J. Respir. Crit. Care Med.* 162:1493-1499 (2000).

Eremina et al., "Glomerular-Specific Alterations of VEGF-A Expression Lead to Distinct Congenital and Acquired Renal Diseases," *J. Clin. Invest.* 111:707-716 (2003).

Ferguson, "Meeting Highlights: Highlights of the 48th Scientific Sessions of the American College of Cardiology," *Circulation* 100:570-575 (1999).

Ferrara et al., "The Role of Vascular Endothelial Growth Factor in Angiogenesis," *Acta Haematol.* 106:148-156 (2001).

Freedman et al., "Therapeutic Angiogenesis for Coronary Artery Disease," *Ann. Intern. Med.* 136:54-71 (2002).

Gille et al., "Analysis of Biological Effects and Signaling Properties of Fit-1 (VEGFR-1) and KDR (VEGFR-2)," *J. Biol. Chem,* 276:3222-3230 (2001).

Graubert et al., "Vascular Repair After Menstruation Involves Regulation of Vascular Endothelial Growth Factor-Receptor Phosphorylation by sFLT-1," *Am. J. Pathol.* 158:1399-1410 (2001).

Hayashi et al., "Changes in Urinary Excretion of Six Biochemical Parameters in Normotensive Pregnancy and Preeclampsia," *Am. J. Kidney Dis.* 39:392-400 (2002).

He et al., "Alternative Splicing of Vascular Endothelial Growth Factor (VEGF)-R1 (FLT-1) Pre-mRNA is Important for the Regulation of VEGF Activity," *Mol. Endocrinol.* 13:537-45 (1999).

He et al., "Vascular Endothelial Growth Factor Signals Endothelial Cell Production of Nitric Oxide and Prostacyclin through Flk-1/KDR Activation of c-Src," *J. Biol. Chem.* 274:25130-25135 (1999).

Heeschen et al., "Nicotine Stimulates Angiogenesis and Promotes Tumor Growth and Atherosclerosis," *Nat. Med.* 7:833-839 (2001).

Henry, et al., "Intracoronary Administration of Recombinant Human Vascular Endothelial Growth Factor to Patients with Coronary Artery Disease," *Am. Heart J.* 142:872-880 (2001).

Holzgreve et al., "Disturbed Feto-Maternal Cell Traffic in Preeclampsia," *Obstet. Gynecol.* 91:669-672 (1998).

Hornig et al., "Release and Complex Formation of Soluble VEGFR-1 from Endothelial Cells and Biological Fluids," *Lab. Invest.* 80:443-454 (2000).

Isner et al., "VEGF Gene Transfer for Diabetic Neuropathy," *Hum. Gene Ther.* 12:1593-1594 (2001).

Isner, "Myocardial Gene Therapy," *Nature* 415:234-239 (2002).

Kabbinavar et al., "Phase II, Randomized Trial Comparing Bevacizumab Plus Fluorouracil (FU)/Leucovorin (LV) with FU/LV Alone in Patients with Metastatic Randomized Colorectal Cancer," *J. Clin. Oncol.* 21:60-65 (2003).

Kaku et al., "Effects of Vascular Endothelial Growth Factor on Osteoclast Induction During Tooth Movement in Mice," *J. Dent. Res.* 80:1880-1883 (2001).

Kendall et al., "Identification of a Natural Soluble Form of the Vascular Endothelial Growth Factor Receptor, FLT-1, and Its Heterodimerization with KDR," *Biochem. Biophys. Res. Commun.* 226:324-328 (1996).

Kendall et al., "Inhibition of Vascular Endothelial Cell Growth Factor Activity by an Endogenously Encoded Soluble Receptor," *Proc. Natl. Acad. Sci.* 90:10705-10709 (1993).

Kincaid-Smith, "The Renal Lesion of Preeclampsia Revisited," *Am. J. Kidney Dis.* 17:144-148 (1991).

Knebelmann et al., "Transforming Growth Factor α Is a Target for the Von Hippel-Lindau Tumor Supressor," *Cancer Res.* 58:226-231 (1998).

Koga et al., "Elevated Serum Soluble Vascular Endothelial Growth Factor Receptor 1 (sVEGFR-1) Levels in Women with Preeclampsia," *J. Clin. Endocrinol. Metab.* 88:2348-2351 (2003).

Koransky, "VEGF Gene Delivery for Treatment of Ischemic Cardiovascular Disease," *Trends Cardiovasc. Med.* 12:108-114 (2002).

Kuo et al., "Comparative Evaluation of the Antitumor Activity of Antiangiogenic Proteins Delivered by Gene Transfer," *Proc. Natl. Acad. Sci. U.S.A.* 98:4605-4610 (2001).

Lai et al., "Inhibition of Angiogenesis by Adenovirus-Mediated sFlt-1 Expression in a Rat Model of Corneal Neovascularization," *Hum. Gene Ther.* 12:1299-1310 (2001).

Lai et al., "Potential Long-Term Inhibition of Ocular Neovascularisation by Recombinant Adeno-Associated Virus-Mediated Secretion Gene Therapy," *Gene Ther.* 9:804-813 (2002).

Lain et al., "Contemporary Concepts of the Pathogenesis and Management of Preeclampsia," *JAMA* 287:3183-3186 (2002).

LeCouter et al., "Identification of an Angiogenic Mitogen Selective for Endocrine Gland Endothelium," *Nature* 412:877-884 (2001).

Levine et al., "Circulating Angiogenic Factors and the Risk of Preeclampsia," *N. Engl. J. Med.* 350:672-683 (2004).

Levine et al., "Trial of Calcium for Preeclampsia Prevention (CPEP): Rationale, Design, and Methods," *Control Clin. Trials* 17:442-469 (1996).

Levine et al., "Trial of Calcium to Prevent Preeclampsia," *N. Engl. J. Med.* 337:69-76 (1997).

Levine et al., "Two-Stage Elevation of Cell-Free Fetal DNA in Maternal Sera Before Onset of Preeclampsia," *Am. J. Obstet. Gynecol.* 190:707-713 (2004).

Lip et al., "Plasma VEGF and Soluble VEGF Receptor FLT-1 in Proliferative Retinopathy: Relationship to Endothelial Dysfunction and Laser Treatment," *Invest. Ophthalmol. Vis. Sci.* 41:2115-2119 (2000).

Luttun et al., "Soluble VEGF Receptor Flt1: The Elusive Preeclampsia Factor Discovered?" *J. Clin. Invest.* 111:600-602 (2003).

Masuda et al., "Vascular Endothelial Growth Factor Enhances Glomerular Capillary Repair and Accelerates Resolution of Experimentally Induced Glomerulonephritis," *Am. J. Pathol.* 159:599-608 (2001).

Maynard et al., "Excess Placental Soluble fms-Like Tyrosine Kinase 1 (sFlt1) May Contribute to Endothelial Dysfunction, Hypertension, and Proteinuria in Preeclampsia," *J. Clinical Invest.* 111:649-658 (2003).

Mills et al., "Prostacyclin and Thromboxane Changes Predating Clinical Onset of Preeclampsia," *JAMA* 281:356-362 (1999).

Morbidelli et al., "Nitric Oxide Mediates Mitogenic Effect of VEGF on Coronary Venular Endothelium," *Am. J. Physiol*, 270:H411-H415 (1996).

Mortensen et al., "Smoking, Sex of the Offspring, and Risk of Placental Abruption, Placenta Previa, and Preeclampsia: A Population-Based Cohort Study," *Acta Obstet. Gynecol. Scan* 80:894-898 (2001).

Myers et al., "Hypertensive Diseases and Eclampsia," *Curr. Opin. Obstet. Gynecol.* 14:119-125 (2002).

Neufeld et al., "Similarities and Differences Between the Vascular Endothelial Growth Factor (VEGF) Splice Variants," *Cancer Metastasis Rev.* 15:153-158 (1996).

Newman et al., "Cigarette Smoking and Pre-Eclampsia: Their Association and Effects on Clinical Outcomes," *J Matern. Fetal. Med.* 10:166-170 (2001).

Nishimoto et al., "Glomerular Hypertrophy in Preeclamptic Patients with Focal Segmental Glomerulosclerosis: A Morphometric Analysis," *Clin. Nephrol.* 51:209-219 (1999).

Ong et al., "First-Trimester Maternal Serum Levels of Placenta Growth Factor as Predictor of Preeclampsia and Fetal Growth Restriction," *Obstet. Gynecol.* 98:608-611 (2001).

Ostendorf et al., "$VEGF_{165}$ Mediates Glomerular Endothelial Repair," *J. Clin. Invest.* 104:913-923 (1999).

Page et al., "Excessive Placental Secretion of Neurokinin B During the Third Trimester Causes Pre-Eclampsia," *Nature* 405:797-800 (2000).

Parry et al., "Dinucleotide Repeat Polymorphisms within the Flt-1 Gene in Minimal Change Nephropathy," *Eur. J. Immunogenet.* 26:321-323 (1999).

Paternoster et al., "Markers of Tubular Damage in Pre-Eclampsia," *Minerva Ginecol.* 51:373-377 (1999).

Polliotti et al., "Second-Trimester Maternal Serum Placental Growth Factor and Vascular Endothelial Growth Factor for Predicting Severe, Early-Onset Preeclampsia," *Obstet. Gynecol.* 101:1266-1274 (2003).

Quirici et al., "Differentiation and Expansion of Endothelial Cells from Human Bone Marrow CD 133[+] Cells," *Br. J. Haematol.* 115:186-194 (2001).

Regnault et al., "Placental Expression of VEGF, PlGF and their Receptors in a Model of Placental Insufficiency—Intrauterine Growth Restriction (PI-IUGR)," *Placenta* 23:132-144 (2002).

Roberts, "Endothelial Dysfunction in Preeclampsia," *Semin. Reprod. Endocrinol.* 16:5-15 (1998).

Roberts et al., "Pathogenesis and Genetics of Pre-Eclampsia," *Lancet* 357:53-56 (2001).

Roes et al., "High Levels of Urinary Vascular Endothelial Growth Factor in Women with Severe Preeclampsia," *Int. J. Biol. Markers* 19:72-75 (2004).

Sato et al., "Increased Pulmonary Vascular Contraction to Serotonin after Cardiopulmonary Bypass: Role of Cyclooxygenase," *J. Surg. Res.* 90:138-143 (2000).

Sibai, "Diagnosis and Management of Gestational Hypertension and Preeclampsia," *Obstet. Gynecol.* 102:181-192 (2003).

Sibai et al., "What We Have Learned About Preeclampsia," *Semin. Perinatol.* 27:239-246 (2003).

Simon et al., "Expression of Vascular Endothelial Growth Factor and its Receptors in Human Renal Ontogenesis and in Adult Kidney," *Am. J. Physiol.* 268:F240-F250 (1995).

Strevens et al., "Glomerular Endotheliosis in Normal Pregnancy and Pre-Eclampsia," *Br. J. Obstet. Gynaecol.* 110:831-836 (2003).

Su et al., "Decreased Maternal Serum Placenta Growth Factor in Early Second Trimester and Preeclampsia," *Obstet. Gynecol.* 97:898-904 (2001).

Taylor et al., "Longitudinal Serum Concentrations of Placental Growth Factor: Evidence for Abnormal Placental Angiogenesis in Pathologic Pregnancies," *Am. J. Obstet. Gynecol..* 188:177-182 (2003).

Thadhani et al., "First Trimester Placental Growth Factor and Soluble FMS-like Tyrosine Kinase 1 and Risk for Preeclampsia," *J. Clin. Endocrinol. Metab.* 89:770-775 (2004).

Tidwell et al., "Low Maternal Serum Levels of Placenta Growth Factor as an Antecedent of Clinical Preeclampsia," *Am. J. Obstet. Gynecol.* 184:1267-72 (2001).

Tischer et al., "The Human Gene for Vascular Endothelial Growth Factor," *J. Biol. Chem.* 266:11947-11954 (1991).

Tjoa et al., "Plasma Placenta Growth Factor Levels in Midtrimester Pregnancies," *Obstet. Gynecol.* 98:600-607 (2001).

Torry et al., "Expression and Function of Placenta Growth Factor: Implications for Abnormal Placentation," *J. Soc. Gynecol. Investig.* 10:178-88 (2003).

Torry et al., "Preeclampsia is Associated with Reduced Serum Levels of Placenta Growth Factor," *Am. J. Obstet. Gynecol.* 179:1539-1544 (1998).

Traver et al., "Walking the Walk: Migration and other Common Themes in Blood and Vascular Development," *Cell* 108:731-734 (2002).

Tsatsaris et al., "Overexpression of the Soluble Vascular Endothelial Growth Factor Receptor in Preeclamptic Patients: Pathophysiological Consequences," *J. Clin. Endocrinol. Metab.* 88:5555-5563 (2003).

Tucci et al., "rhVEGF and Experimental Rat Skin Flaps: Systemic or Local Administration and Morphological Characteristics," *Int. J. Artif. Organs* 24:743-751 (2001).

Vuorela et al., "Amniotic Fluid-Soluble Vascular Endothelial Growth Factor Receptor-1 in Preeclampsia," *Obstet. Gynecol.* 95:353-357 (2000).

Walker, "Pre-Eclampsia," *Lancet* 356:1260-1265 (2000).

Yang et al., "A Randomized Trial of Bevacizumab, an Anti-Vascular Endothelial Growth Factor Antibody, for Metastatic Renal Cancer," *N. Engl. J. Med.* 349:427-434 (2003).

Yang et al., "sFlt-1 Gene Transfected Fibroblasts: A Wound-Specific Gene Therapy Inhibits Local Cancer Recurrence," *Cancer Res.* 61:7840-7845 (2001).

Zhang et al., "Birth-Weight-for-Gestational-Age-Patterns by Race, Sex, and Parity In the United States Population," *Obstet. Gynecol.* 86:200-208 (1995).

Zhou et al., "Preeclampsia is Associated with Failure of Human Cytotrophoblasts to Mimic a Vascular Adhesion Phenotype. One Cause of Defective Endovascular Invasion in this Syndrome?" *J. Clin. Invest* 99:2152-2164 (1997).

Zhou et al., "Vascular Endothelial Growth Factor Ligands and Receptors that Regulate Human Cytotrophoblast Survival are Dysregulated in Severe Preeclampsia and Hemolysis, Elevated Liver Enzymes, and Low Platelets Syndrome," *Am. J. Pathol.* 160:1405-1423 (2002).

Del-Sorbo et al., "The Synthesis of Platelet-Activating Factor Modulates Chemotaxis of Monocytes Induced by HIV-1 Tat," *Eur. J. Immunol.* 29:1513-1521 (1999).

Gordon et al., "Phase I Safety and Pharmacokinetic Study of Recombinant Human Anti-Vascular Endothelial Growth Factor in Patients with Advanced Cancer," *J. Clin. Oncol.* 19:843-850 (2001).

Hunter et al., "Serum Levels of Vascular Endothelial Growth Factor in Preeclamptic and Normotensive Pregnancy," *Hypertension* 36:965-959 (2000).

Margolin et al., "Phase 1b Trial of Intravenous Recombinant Humanized Monoclonal Antibody to Vascular Endothelial Growth Factor in Combination with Chemotherapy in Patients with Advanced Cancer: Pharmacologic and Long-Term Safety Data," *J. Clin. Oncol.* 19:851-856 (2001).

Sugimoto et al., "Neutralization of Circulating Vascular Endothelial Growth Factor (VEGF) by Anti-VEGF Antibodies and Soluble VEGF Receptor 1 (sFlt-1) Induces Proteinuria," *J. Biol. Chem.* 278:12605-12608 (2003).

Office Action for U.S. Appl. No. 10/624,809 mailed on Jun. 30, 2006.

Office Action for U.S. Appl. No. 10/624,809 mailed on May 1, 2007.

Office Action for U.S. Appl. No. 10/771,518 mailed on Jun. 23, 2006.

Office Action for U.S. Appl. No. 10/771,518 mailed on Mar. 8, 2007.

U.S. Appl. No. 10/920,116, filed Aug. 16, 2004, Thadhani et al. (Pending Application).

U.S. Appl. No. 10/947,791, filed Sep. 23, 2004, Thadhani et al. (Pending Application).

Baker et al., "Elevated serum levels of vascular endothelial growth factor in patients with preeclampsia," *Obstet. Gynecol.* 86: 815-821 (1995).

Brockelsby et al., "VEGF via VEGF receptor-1 (Flt-1) mimics preeclamptic plasma in inhibiting uterine blood vessel relaxation in pregnancy: Implications in the pathogenesis of preeclampsia," *Lab. Invest.* 79: 1101-1111 (1999).

Davis-Smyth et al., "The second immunoglobulin-like domain of the VEGF tyrosine kinase receptor Flt-1 determines ligand binding and may initiate a signal transduction cascade," *EMBO J.* 15: 4919-4927 (1996).

Davis-Smyth et al., "Mapping the charged residues in the second immunoglobulin-like domain of the vascular endothelial growth factor/placenta growth factor receptor Flt-1 required for binding and structural stability," *J. Biol. Chem.* 273: 3216-3222 (1998).

Dvorak, "Vascular permeability factor/vascular endothelial growth factor: A critical cytokine in tumor angiogenesis and a potential target for diagnosis and therapy," *J. Clin. Oncol.* 20: 4368-4380 (2002).

Errico et al., "Identification of placenta growth factor determinants for binding and activation of Flt-1 receptor," *J. Biol. Chem.* 279: 43929-43939 (2004).

Ferrara et al., "Role of vascular endothelial growth factor in regulation of physiological angiogenesis," *Am. J. Physiol. Cell Physiol.* 280: C1358-C1366 (2001).

Ferrara et al., "The biology of VEGF and its receptors," *Nat. Med.* 9: 669-676 (2003).

Hsieh, Tsang-Tang, "Maternal serum placenta growth factor and vascular endothelial growth factor in pregnancies complicated by preeclampsia," *Am. J. Obstet. Gynecol.* 184: S70 (2001), (Abstract).

Iyer et al., "The crystal structure of human placenta growth factor-1 (PIGF-1), an angiogenic protein, at 2.0 Å resolution," *J. Biol. Chem.* 276: 12153-12161, 2001.

Keyt et al., "Identification of vascular endothelial growth factor determinants for binding KDR and Flt-1 receptors," *J. Biol. Chem.* 271:5638-5646 (1996).

Krussel et al., "Expression of mRNA for vascular endothelial growth factor transmembraneous receptors Flt1 and KDR, and the soluable receptor sflt in cycling human endometrium," *Mol. Hum. Reprod.* 5: 452-458 (1999).

Li et al., "Recombinant VEGF121 Attenuates Hypertension and Improves Kidney Damage in a Rat Model of Preeclampsia," *Hypertension* 092098 (2007).

Lyall et al., "Suppression of serum vascular endothelial growth factor immunoreactivity in normal pregnancy and in pre-eclamsia," *BJOG* 104:223-228 (1997).

Maynard et al., "Sflt-1, a circulating VEGF antagonist, is up-regulated in preeclampsia and contributes to endothelial dysfunction," *J. Am. Soc. Nephrol.* 13:SU-FC280 (2002).

Moran et al., "Glomerular Ultrafiltration in Normal and Preeclamptic Pregnancy," *J. Am. Soc. Nephrol.* 14:648-652 (2003).

Muller et al., "Vascular endothelial growth factor: crystal structure and functional mapping of the kinase domain receptor binding site," *Proc. Natl. Acad. Sci. USA* 94: 7192-7197 (1997).

Muller et al., "The crystal structure of vascular endothelial growth factor (VEGF) refined to 1.93 Å resolution: multiple copy flexibility and receptor binding," *Structure* 5: 1325-1338 (1997).

Olofsson et al., "Vascular endothelial growth factor B (VEGF-B) binds to VEGF receptor-1 and regulates plasminogen activator activity in endothelial cells," *Proc. Natl. Acad. Sci. USA* 95: 11709-11714 (1998).

Park et al., "Potentiation of vascular endothelial growth factor bioactivity, in vitro and in vivo, and high affinity binding to Flt-1 but not to Flk-1/KDR," *J. Biol. Chem.* 269: 25646-25654 (1994).

Park et al., "An elevated maternal plasma, but not amniotic fluid, soluble fms-like tyrosine kinase-1 (sFlt-1) at the time of mid-trimester genetic amniocentesis is a risk factor for preeclampsia," *Am. J. Obstet. Gynecol.* 193: 984-989 (2005).

Powers et al., "Maternal serum soluble fms-like tyrosine kinase 1 concentrations are not increased in early pregnancy and decrease more slowly postpartum in women who develop preeclampsia," *Am. J. Obstet. Gynecol.* 193: 185-191 (2005).

Reuvekamp et al., "Selective deficit of angiogenic growth factors characterises pregnancies complicated by pre-eclampsia," *BJOG* 106: 1019-1022 (1999).

Sawano et al., "Flt-1 but not KDR/Flk-1 tyrosine kinase is a receptor for placenta growth factor, which is related to vascular endothelial growth factor," *Cell Growth Differ.* 7: 213-221 (1996).

Vuorela, "Vascular endothelial growth factor, its receptors, and the Tie receptor in normal and complicated pregnancy," Department of Obstetrics and Gynaecology, Helsinki University Central Hospital, University of Helsinki, Finland (2000).

Walsh et al., "Computer modelling of the receptor-binding domains of VEGF and PIGF," *Protein Eng.* 10: 389-398 (1997).

Wiesmann et al., "Crystal structure and 1.7 Å resolution of VEGF in complex with domain 2 of the Flt-1 receptor," *Cell* 91: 695-704 (1997).

European Search Report dated May 23, 2007 (PCT/US0322892).

\* cited by examiner

Fc sFlt-1

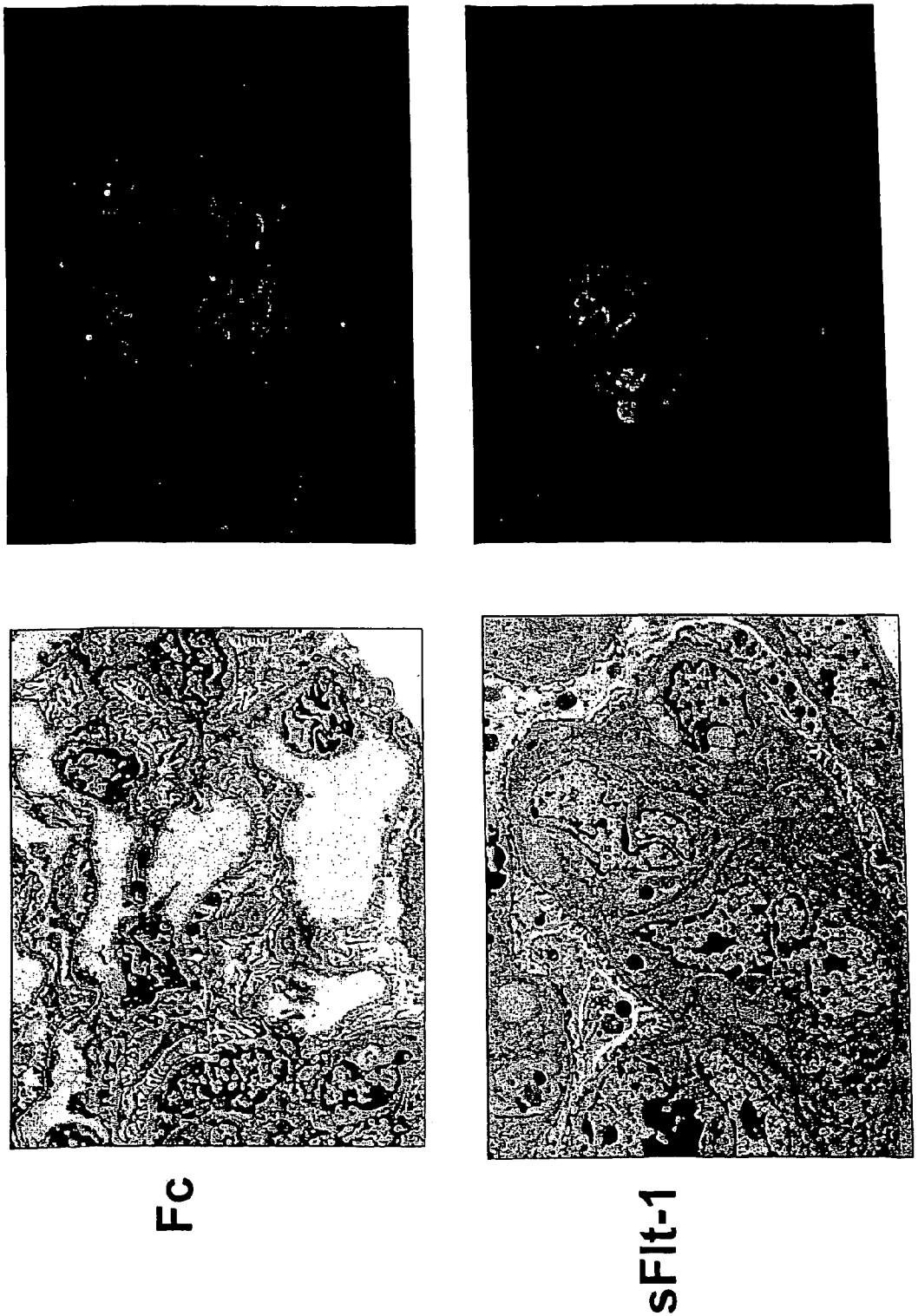

METHODS OF DIAGNOSING AND TREATING PRE-ECLAMPSIA OR ECLAMPSIA

CROSS REFERENCE TO RELATED APPLICATIONS

This application is a continuation-in-part of U.S. patent application Ser. No. 10/771,518, filed Feb. 4, 2004, which is a continuation-in-part of U.S. patent application Ser. No. 10/624,809, filed Jul. 21, 2003, which claims the benefit of U.S. Provisional Application Nos. 60/467,390 filed on May 2, 2003, 60/451,796, filed on Mar. 3, 2003, and 60/397,481, filed on Jul. 19, 2002, each of which is herein incorporated by reference in their entirety.

FIELD OF THE INVENTION

In general, this invention relates to the detection and treatment of subjects having pre-eclampsia or eclampsia.

BACKGROUND OF THE INVENTION

Pre-eclampsia is a syndrome of hypertension, edema, and proteinuria that affects 5 to 10% of pregnancies and results in substantial maternal and fetal morbidity and mortality. Pre-eclampsia accounts for at least 200,000 maternal deaths worldwide per year. The symptoms of pre-eclampsia typically appear after the $20^{th}$ week of pregnancy and are usually detected by routine ing of the woman's blood pressure and urine. However, these monitoring methods are ineffective for diagnosis of the syndrome at an early stage, which could reduce the risk to the subject or developing fetus, if an effective treatment were available.

Currently there are no known cures for pre-eclampsia. Pre-eclampsia can vary in severity from mild to life threatening. A mild form of pre-eclampsia can be treated with bed rest and frequent monitoring. For moderate to severe cases, hospitalization is recommended and blood pressure medication or anticonvulsant medications to prevent seizures are prescribed. If the condition becomes life threatening to the mother or the baby the pregnancy is terminated and the baby is delivered pre-term.

The proper development of the fetus and the placenta is mediated by several growth factors. One of these growth factors is vascular endothelial growth factor (VEGF). VEGF is an endothelial cell-specific mitogen, an angiogenic inducer, and a mediator of vascular permeability. VEGF has also been shown to be important for glomerular capillary repair. VEGF binds as a homodimer to one of two homologous membrane-spanning tyrosine kinase receptors, the fms-like tyrosine kinase (Flt-1) and the kinase domain receptor (KDR), which are differentially expressed in endothelial cells obtained from many different tissues. Flt-1, but not KDR, is highly expressed by trophoblast cells which contribute to placental formation. Placental growth factor (PlGF) is a VEGF family member that is also involved in placental development. PlGF is expressed by cytotrophoblasts and syncytiotrophoblasts and is capable of inducing proliferation, migration, and activation of endothelial cells. PlGF binds as a homodimer to the Flt-1 receptor, but not the KDR receptor. Both PlGF and VEGF contribute to the mitogenic activity and angiogenesis that are critical for the developing placenta.

A soluble form of the Flt-1 receptor (sFlt-1) was recently identified in a cultured medium of human umbilical vein endothelial cells and in vivo expression was subsequently demonstrated in placental tissue. sFlt-1 is a splice variant of the Flt-1 receptor which lacks the transmembrane and cytoplasmic domains. sFlt-1 binds to VEGF with a high affinity but does not stimulate mitogenesis of endothelial cells. sFlt-1 is believed to act as a "physiologic sink" to down-regulate VEGF signaling pathways. Regulation of sFlt-1 levels therefore works to modulate VEGF and VEGF signaling pathways. Careful regulation of VEGF and PlGF signaling pathways is critical for maintaining appropriate proliferation, migration, and angiogenesis by trophoblast cells in the developing placenta. There is a need for methods of accurately diagnosing subjects at risk for or having pre-eclampsia, particularly before the onset of the most severe symptoms. A treatment is also needed.

SUMMARY OF THE INVENTION

We have discovered a means for diagnosing and effectively treating pre-eclampsia and eclampsia.

Using gene expression analysis, we have discovered that levels of sFlt-1 are markedly elevated in placental tissue samples from pregnant women suffering from pre-eclampsia. sFlt-1 is known to antagonize VEGF and PlGF by acting as a "physiologic sink" and, in pre-eclamptic or eclamptic women, sFlt-1 may be depleting the placenta of necessary amounts of these essential angiogenic and mitogenic factors. Excess sFlt-1 may also lead to eclampsia by disrupting the endothelial cells that maintain the blood-brain barrier and/or endothelial cells lining the choroids plexus of the brain thus leading to cerebral edema and the seizures seen in eclampsia. In the present invention, compounds that increase VEGF and PlGF levels are administered to a subject to treat or prevent pre-eclampsia or eclampsia by countering the effects of elevated sFlt-1. In addition, antibodies directed to sFlt-1 are used to competitively inhibit binding of VEGF or PlGF to sFlt-1, thereby increasing the levels of free VEGF and PlGF. RNA interference and antisense nucleobase oligomers are also used to decrease the levels of sFlt-1. The present invention provides for the use and monitoring of sFlt-1, VEGF, and PlGF as detection tools for early diagnosis and management of pre-eclampsia or eclampsia, or a predisposition thereto, or a cardiovascular condition, or a predisposition thereto.

We have also discovered that PlGF levels in the urine can be used as a diagnostic tool to detect pre-eclampsia or eclampsia, or a predisposition thereto. The free form of PlGF has an average molecular weight of about 30 kDa and is small enough to be filtered by the kidney and released into the urine. PlGF, when complexed to sFlt-1, has a much greater molecular weight and would therefore not be released into the urine. When the levels of sFlt-1 are increased, sFlt-1 can complex to PlGF, thereby reducing the levels of free PlGF released into the urine. As a result, urine analysis for free PlGF levels can be used to diagnose pre-eclampsia or eclampsia or a patient at risk for having the same.

Accordingly, in one aspect, the invention features a method of diagnosing a subject as having, or having a propensity to develop, pre-eclampsia or eclampsia that includes measuring the level of free PlGF in a urine sample from the subject. This method can be used to determine absolute levels of free PlGF that are below a threshold level and are diagnostic of pre-eclampsia or eclampsia or the propensity to develop pre-eclampsia or eclampsia. The normal urinary concentration of urinary PlGF is approximately 400-800 pg/ml during mid-pregnancy. In preferred embodiments, a level of free PlGF less than 400 pg/ml, preferably less than 300, 200, 100, 50, or 10 pg/ml is diagnostic of pre-eclampsia or eclampsia or the propensity to develop pre-eclampsia or eclampsia. This method can also be used to determine relative levels of free PlGF as compared to a reference sample where a decrease (e.g., 10%, 20%, 25%, 50%, 75%, 90%, or more) in the level of free PlGF as compared to a normal reference sample is diagnostic of pre-eclampsia or eclampsia or the propensity to develop pre-eclampsia or eclampsia. In this case, the normal reference sample can be a prior sample taken from the same subject or a sample taken from a matched subject (e.g., matched for gestational age) that is pregnant but does not have pre-eclampsia or eclampsia or a propensity to develop pre-eclampsia or eclampsia. In additional preferred embodiments, the reference sample is a standard, level, or number derived from such a normal reference sample. The reference standard or level can also be a value derived from a normal subject that is matched to the sample subject by at least one of the following criteria: gestational age of the fetus, age of the mother, blood pressure prior to pregnancy, blood pressure during pregnancy, BMI of the mother, weight of the fetus, prior diagnosis of pre-eclampsia or eclampsia, and a family history of pre-eclampsia or eclampsia. In preferred embodiments, the measuring is done using an immunological assay such as an ELISA, preferably a sandwich ELISA, or a fluorescence immunoassay.

In preferred embodiments, the method also includes the steps of (a) measuring the level of at least one of sFlt-1, PlGF, and VEGF polypeptide in a sample from the subject, where the sample is a bodily fluid selected from the group consisting of urine, blood, amniotic fluid, serum, plasma, or cerebrospinal fluid, and (b) comparing the level of at least one of sFlt-1, PlGF, and VEGF from the subject to the level of the same polypeptide in a reference sample, where an increase in the level of sFlt-1 or a decrease in the level of VEGF or PlGF polypeptide from the subject sample compared to the reference sample is a diagnostic indicator of pre-eclampsia or eclampsia, or a propensity to develop pre-eclampsia or eclampsia. In preferred embodiments, sFlt-1 or sFlt-1 and PlGF are measured in a serum sample from a subject identified by a urine PlGF assay as being at risk for developing pre-eclampsia or eclampsia. Desirably, this method further includes calculating the relationship between the levels of at least one of sFlt-1, VEGF, and PlGF from step (a) above using a metric, where an alteration in the subject sample relative to the metric in the reference sample diagnoses pre-eclampsia or eclampsia or a propensity to develop pre-eclampsia or eclampsia. Preferably, the metric is a PAAI (as described above) and a PAAI value greater than 20 is a diagnostic indicator of pre-eclampsia or eclampsia. In preferred embodiments, the sFlt-1 is free, bound, or total sFlt-1, and the PlGF and VEGF are free PlGF and free VEGF.

In another aspect, the invention features a method of diagnosing a subject as having or having a propensity to develop pre-eclampsia or eclampsia that includes the following steps:
  (a) obtaining a sample of urine from the subject;
  (b) contacting the sample with a solid support, where the solid support includes an immobilized first PlGF binding agent, for a time sufficient to allow binding of the first PlGF binding agent with free PlGF present in the sample;
  (c) contacting the solid support after step (b) with a preparation of a second labeled PlGF binding agent, for a time sufficient to allow binding of the second labeled PlGF binding agent to the free PlGF bound to the first immobilized PlGF binding agent;
  (d) observing the binding of the second labeled PlGF binding agent to the immobilized PlGF binding agent bound to free PlGF at the position where the PlGF binding agent is immobilized; and
  (e) comparing the binding observed in step (d) with the binding observed using a reference sample, where the reference sample is PlGF at a known concentration; and further where a decrease in the binding observed in step (d) compared to the binding observed using a reference sample is a diagnostic indicator of pre-eclampsia or eclampsia or a propensity to develop pre-eclampsia or eclampsia.

In another related aspect, the invention features a method of diagnosing a subject as having or having a propensity to develop pre-eclampsia or eclampsia, that includes the following steps:
  (a) obtaining a urine sample from the subject;
  (b) contacting the urine sample with a solid support, wherein the solid support comprises a dehydrated labeled PlGF binding agent and an immobilized secondary agent that binds the PlGF binding agent, for a time sufficient for the sample to rehydrate the labeled PlGF binding agent and to allow binding of free PlGF in the sample to the labeled PlGF binding agent, wherein the free PlGF bound to the labeled PlGF binding agent can move (e.g., by capillary movement) to the immobilized secondary agent;
  (c) observing the binding of the free PlGF-PlGF binding agent complex to the immobilized secondary agent by detecting the presence of the label at the position where the secondary agent is immobilized; and
  (d) comparing the binding observed in step (c) with the binding observed using a reference sample, wherein the reference sample is PlGF at known concentrations ranging from 10 pg/ml-1 ng/ml.

In preferred embodiments of the above two aspects, the label is a calorimetric label (e.g., colloidal gold). In additional preferred embodiments, the agent that binds PlGF is an antibody, or purified fragment thereof, or a peptide. Desirably, the antibody or purified fragment thereof specifically binds free PlGF. The agent that binds a PlGF agent is desirably an anti-immunoglobulin antibody or fragment thereof, protein A, or protein G. In one embodiment, the reference sample is a PlGF sample at a known normal concentration and a decrease in the free PlGF in the subject sample as compared to the reference sample is diagnostic of pre-eclampsia or eclampsia or a propensity to develop pre-eclampsia or eclampsia.

In another aspect, the invention features a method of diagnosing a subject as having or having a propensity to develop pre-eclampsia or eclampsia that includes the following steps:
  (a) obtaining a urine sample from the subject;
  (b) contacting the sample with a solid support having an immobilized PlGF binding agent that is detectably labeled in a manner such that the label can distinguish between the PlGF when it is bound to free PlGF and when it is not bound to free PlGF. Preferred labels include fluorescent labels. The membrane is exposed to a urine sample obtained from the subject for a time sufficient to allow binding of the PlGF binding agent to free PlGF present in the sample. The labeled PlGF binding agent bound to the free PlGF is then measured. Such an assay can be used to determine the relative level of PlGF (e.g., as compared to the level from a reference sample or standard or level) or to determine the absolute concentration of PlGF as described above. Preferred assays for the measurement of binding include fluorescence immunoassays.

In another aspect the invention features a method of diagnosing a subject as having or having a propensity to develop pre-eclampsia or eclampsia that includes the following steps:
  (a) obtaining a urine sample from the subject;
  (b) contacting the sample with a solid support, wherein the solid support comprises an immobilized first PlGF binding agent, for a time sufficient to allow binding of the first PlGF binding agent with free PlGF present in the sample;
  (c) contacting the solid support after step (b) with a preparation of a second PlGF binding agent coupled to an enzyme, for a time sufficient to allow binding of the second PlGF binding agent to the PlGF bound to the first immobilized PlGF binding agent; and (d) adding a preparation of a substrate for the enzyme of step (c), for a time and in an amount sufficient to allow the enzyme to convert the substrate to a detectable substrate;

(e) observing the level of the detectable substrate; and (f) comparing the level observed in step (e) with the binding observed using a reference sample, wherein the reference sample is PlGF at a known concentration, wherein an alteration in the level observed in step (e) as compared to the reference sample is a diagnostic indicator of pre-eclampsia or eclampsia or a propensity to develop pre-eclampsia or eclampsia.

In one embodiment, the reference sample is a PlGF sample at a known normal concentration and a decrease in the free PlGF in the subject sample as compared to the reference sample is diagnostic of pre-eclampsia or eclampsia or a propensity to develop pre-eclampsia or eclampsia.

In preferred embodiments of the above method, the substrate is detected visually, by spectrophotometry or by chemiluminescence. In additional preferred embodiments, the enzyme is horseradish peroxidase, P-galactosidase, or alkaline phosphatase and the substrate is TMB (tetramethylbenzidine), Xgal (5-bromo-4-chloro-3-indolyl-β-D-galactopyranoside), or 1,2 dioxetane. In additional preferred embodiments, the reference sample is a sample having a normal concentration of purified PlGF and the subject sample shows a decrease (10%, 25%, 50%, 75%, 90% or more) compared to the reference sample. In preferred embodiments of this method, the PlGF binding agent is a purified anti-PlGF antibody, or fragment thereof, or a peptide. Desirably, the purified anti-PlGF antibody, or fragment thereof specifically binds free PlGF.

In preferred embodiments of any of the above diagnostic methods, the solid support is a membrane that can be supported on a dipstick structure or a lateral flow format, examples of which are described in U.S. Pat. No. 6,660,534. In additional preferred embodiments, the subject is a non-pregnant human, a pregnant human, or a post-partum human. In other embodiments of the above aspects, the subject is a non-human (e.g., a cow, a horse, a sheep, a pig, a goat, a dog, or a cat). In one embodiment, the subject is a non-pregnant human and the method is used to diagnose a propensity to develop pre-eclampsia or eclampsia. In another embodiment, the subject is a human (pregnant or non-pregnant) with a history of pre-eclampsia and the method is used to diagnose a propensity to develop pre-eclampsia or eclampsia in a subsequent pregnancy. Desirably, the measuring of levels is done on two or more occasions and a change in the levels between measurements is a diagnostic indicator of pre-eclampsia or eclampsia.

In additional preferred embodiments, the methods to detect PlGF levels in a urine sample from a subject can be combined with any of the diagnostic methods described below used to measure the level of sFlt-1, PlGF, or VEGF nucleic acid or polypeptide.

In another aspect, the invention provides a method of diagnosing a subject as having, or having a propensity to develop, pre-eclampsia or eclampsia, the method involves measuring the level of sFlt-1, VEGF, or PlGF polypeptide in a sample from the subject.

In a related aspect, the invention provides a method of diagnosing a subject as having, or having a propensity to develop, pre-eclampsia or eclampsia, by determining the levels of at least two of sFlt-1, VEGF, or PlGF polypeptide in a sample from a subject and calculating the relationship between the levels of sFlt-1 VEGF, or PlGF using a metric, where an alteration in the subject sample relative to a reference diagnoses pre-eclampsia or eclampsia in a subject. In preferred embodiments, the method also includes determining the body mass index (BMI), the gestational age (GA) of the fetus, or both and including the BMI or GA or both in the metric. In one embodiment, the metric is a pre-eclampsia anti-angiogenic index (PAAI): [sFlt-1/VEGF+PlGF], where the PAAI is used as an indicator of anti-angiogenic activity. In one embodiment, a PAAI greater than 10, more preferably greater than 20, is indicative of pre-eclampsia or eclampsia. In another embodiment, the levels of sFlt-1, VEGF, or PlGF polypeptide is determined by an immunological assay, such as an ELISA.

In various embodiments of the above aspects, the sample is a bodily fluid, such as serum or urine. In one embodiment, a level of sFlt-1 greater than 2 ng/ml is indicative of pre-eclampsia or eclampsia. In preferred embodiments of the above aspects, the level of sFlt-1 polypeptide measured is the level of free, bound, or total sFlt-1 polypeptide. In additional embodiments, the sFlt-1 polypeptide can also include sFlt-1 fragments, degradation products, or enzymatic cleavage products. In other preferred embodiments of the above aspects, the level of VEGF or PlGF is the level of free VEGF or PlGF.

In another aspect, the invention provides a method of diagnosing a subject as having, or having a propensity to develop, pre-eclampsia or eclampsia that includes measuring the level of sFlt-1, VEGF, or PlGF nucleic acid molecule in a sample from the subject and comparing it to a reference sample, where an alteration in the levels diagnoses pre-eclampsia or eclampsia in the subject, or diagnoses a propensity to develop pre-eclampsia or eclampsia.

In another aspect, the invention provides a method of diagnosing a subject as having, or having a propensity to develop, pre-eclampsia or eclampsia. This method involves determining the nucleic acid sequence of a sFlt-1, VEGF, or PlGF gene in a subject and comparing it to a reference sequence, where an alteration in the subject's nucleic acid sequence that changes the level or the biological activity of the gene product in the subject diagnoses the subject with pre-eclampsia or eclampsia, or a propensity to develop pre-eclampsia or eclampsia. In one embodiment, the alteration is a polymorphism in the nucleic acid sequence.

In various embodiments of any of the above aspects, the sample is a bodily fluid (e.g., urine, amniotic fluid, serum, plasma, or cerebrospinal fluid) of the subject in which the sFlt-1, VEGF, or PlGF is normally detectable. In additional embodiments, the sample is a tissue or a cell. Non-limiting examples include placental tissue or placental cells, endothelial cells, leukocytes, and monocytes. In other embodiments of the above aspects, the subject is a non-pregnant human, a pregnant human, or a post-partum human. In other embodiments of the above aspects, the subject is a non-human (e.g., a cow, a horse, a sheep, a pig, a goat, a dog, or a cat). In one embodiment, the subject is a non-pregnant human and the method is used to diagnose a propensity to develop pre-eclampsia or eclampsia. In other embodiments of the above aspects, at least one of the levels measured is the level of sFlt-1 (free, bound, or total). In additional embodiments, the level of sFlt-1 measured includes the level of sFlt-1 degradation products or enzymatic cleavage products. In other embodiments of the above aspects, when the level of VEGF is measured then the level of sFlt-1 or PlGF is also measured. In additional embodiments, the BMI or GA or both is also measured. In various embodiments of the above aspects, an increase in the level of sFlt-1 nucleic acid or polypeptide relative to a reference is a diagnostic indicator of pre-eclampsia or eclampsia. In other embodiments of the above aspects, a decrease in the level of free VEGF polypeptide or VEGF nucleic acid relative to a reference is a diagnostic indicator of pre-eclampsia or eclampsia. In other embodiments of the above aspects, a decrease in the level of free PlGF polypeptide or PlGF nucleic acid relative to a reference is a diagnostic indicator of pre-eclampsia or eclampsia.

In additional embodiments of the above aspects, the levels are measured on two or more occasions and a change in the levels between the measurements is a diagnostic indicator of pre-eclampsia or eclampsia. In one preferred embodiment, the level of sFlt-1 increases from the first measurement to the next measurement. In another preferred embodiment, the level of VEGF or PlGF decreases from the first measurement to the next measurement.

Any of the methods and kits described herein can be used to diagnose pre-eclampsia or eclampsia or to predict a subsequent pre-eclampsia in a previously pregnant woman or a woman with a history of pre-eclampsia.

Any of the diagnostic methods described herein can also be used to monitor pre-eclampsia or eclampsia in the subject. In preferred embodiments, the diagnostic methods are used to monitor the subject during therapy or to determine effective therapeutic dosages. In one embodiment, a decrease in the level of sFlt-1 polypeptide or nucleic acid measured during or after administering therapy relative to the value before therapy indicates an improvement in the pre-eclampsia or eclampsia. In a preferred embodiment, a level of sFlt-1 polypeptide less than 2 ng/ml indicates an improvement in the pre-eclampsia or eclampsia. In another embodiment, a therapeutic compound is administered in a dose such that the level of sFlt-1 polypeptide is less than 2 ng/ml. In another embodiment, an increase in the level of VEGF or PlGF polypeptide or nucleic acid measured during or after administering therapy relative to the value before therapy indicates an improvement in the pre-eclampsia or eclampsia. In yet another embodiment, a decrease in the PAAI value of a subject indicates an improvement in the pre-eclampsia or eclampsia. In preferred embodiments, the PAAI is less than 20, more preferably less than 10. A decrease in the PAAI can also indicate an effective dosage of a therapeutic compound. In one example, a therapeutic compound is administered in a dose such that the PAAI is less than 20. In another example, a therapeutic compound is administered in a dose such that the PAAI is less than 10. In preferred embodiments, the measuring of the levels of sFlt-1, PlGF, or VEGF is done on two or more occasions and a change in the levels between measurements is used to monitor therapy or to determine therapeutic dosages of a compound. The diagnostic methods described above that include the measurement of free PlGF in a urine sample can be used to monitor the subject during therapy or to determine effective therapeutic dosages. For example, a urine test for PlGF levels as described above can be used on a regular basis (e.g., monthly, weekly, every other day, daily, or hourly) for the duration of the therapy to monitor the subject. In one embodiment, the therapeutic compound is administered in a dose such that the PlGF concentration is greater than 200 pg/ml, 300 pg/ml, 400 pg/ml, 500 pg/ml, 600 pg/ml, 700 pg/ml or 800 pg/ml. For monitoring assays using PlGF, the reference sample will be a concentration of PlGF indicative of pre-eclampsia (less than 400 pg/ml) and an increase in the PlGF concentration as compared to the reference sample will indicate an effective dosage of a therapeutic compound.

In a related aspect, the invention provides a kit for the diagnosis of pre-eclampsia or eclampsia in a subject comprising a component useful for detecting a sFlt-1, VEGF, or PlGF polypeptide, or any combination thereof. In one embodiment, the component is an assay selected from the group consisting of an immunological assay, an enzymatic assay, and a calorimetric assay. In other embodiments of the above aspects, the kit diagnoses a propensity to develop pre-eclampsia or eclampsia in a pregnant or a non-pregnant subject. In preferred embodiments of the above aspects, the kit detects VEGF, sFlt-1, or PlGF. In other preferred embodiments of the above aspects, when the kit detects VEGF then sFlt-1 or PlGF is also detected. In additional preferred embodiments, the kit is used to detect VEGF, sFlt-1 and PlGF and to determine the PAAI of the sample.

In another aspect, the invention provides a diagnostic kit for the diagnosis of pre-eclampsia or eclampsia in a subject that includes a nucleic acid sequence, or fragment thereof, selected from the group consisting of sFlt-1, VEGF, and PlGF nucleic acid molecule, or a sequence complementary thereto, or any combination thereof. In a preferred embodiment, the kit comprises at least two probes for the detection of an sFlt-1, VEGF, or PlGF nucleic acid molecule.

The invention also provides a kit for the diagnosis of pre-eclampsia or eclampsia in a subject that includes a PlGF binding agent for detecting free PlGF in a urine sample and instructions for its used for the diagnosis of pre-eclampsia or eclampsia, or a propensity to develop pre-eclampsia or eclampsia in a subject. The kit can also include a component useful for an assay selected from the following: an immunological assay (e.g., an ELISA) an enzymatic assay or a calorimetric assay. Desirably, the kit includes any of the components needed to perform any of the diagnostic methods described above. For example, the kit desirably includes a membrane, where the PlGF binding agent or the agent that binds the PlGF binding agent is immobilized on the membrane. The membrane can be supported on a dipstick structure where the sample is deposited on the membrane by placing the dipstick structure into the sample or the membrane can be supported in a lateral flow cassette where the sample is deposited on the membrane through an opening in the cassette.

In preferred embodiments of any of the diagnostic kits described above, the diagnostic kits include a label or instructions for the intended use of the kit components and a reference sample or purified proteins to be used to establish a standard curve. In one embodiment, the diagnostic kit is labeled or includes instructions for use in the diagnosis of pre-eclampsia or eclampsia, or a propensity to develop pre-eclampsia or eclampsia in a subject. In another embodiment, the diagnostic kit is labeled or includes instructions for use in the diagnosis of a cardiovascular condition or a propensity to develop a cardiovascular condition. In yet another embodiment, the diagnostic kit is labeled or includes instructions for use in therapeutic monitoring or therapeutic dosage determination. In a preferred embodiment, the diagnostic kit includes a label or instructions for the use of the kit to determine the PAAI of the subject sample and to compare the PAAI to a reference sample value. It will be understood that the reference sample values will depend on the intended use of the kit. For example, the sample can be compared to a normal PAAI reference value or a normal PlGF value, wherein an increase in the PAAI or a decrease in the PlGF value is indicative of pre-eclampsia or eclampsia, or a propensity to develop pre-eclampsia or eclampsia. In another example, a kit used for therapeutic monitoring can have a reference PAAI value or PlGF value that is indicative of pre-eclampsia or eclampsia, wherein a decrease in the PAAI value or an increase in the PlGF value of the subject sample relative to the reference sample can be used to indicate therapeutic efficacy or effective dosages of therapeutic compounds.

In a related aspect, the invention features a device for diagnosing a subject as having or having a propensity to develop pre-eclampsia or eclampsia that includes a means for comparing the levels of at least one of sFlt-1, VEGF, and PlGF polypeptides in a sample from a subject relative to a reference sample, wherein an alteration in the levels of at least one of sFlt-1, VEGF, and PlGF diagnoses pre-eclampsia or eclampsia or a propensity to develop pre-eclampsia or eclampsia in the subject. In a preferred embodiment the device includes a means for using a metric to compare the levels as at least two of sFlt-1, VEGF, and PlGF polypeptides.

In a related aspect, the invention features a device for diagnosing a subject as having or having a propensity to develop pre-eclampsia or eclampsia that includes a component for comparing the levels of at least one of sFlt-1, VEGF, and PlGF nucleic acid molecules in a sample from a subject relative to a reference sample, wherein an alteration in the levels of at least one of sFlt-1, VEGF, and PlGF diagnoses pre-eclampsia or eclampsia or a propensity to develop pre-eclampsia or eclampsia in the subject. In a preferred embodiment the device includes a component for using a metric to compare the levels as at least two of sFlt-1, VEGF, and PlGF nucleic acid molecules.

For the purpose of the present invention, the following abbreviations and terms are defined below.

By "alteration" is meant a change (increase or decrease) in the expression levels of a gene or polypeptide as detected by standard art known methods such as those described above. As used herein, an alteration includes a 10% change in expression levels, preferably a 25% change, more preferably a 40% change, and most preferably a 50% or greater change in expression levels. "Alteration" can also indicate a change (increase or decrease) in the biological activity of any of the polypeptides of the invention (e.g., sFlt-1, VEGF, or PlGF). Examples of biological activity for PlGF or VEGF include binding to receptors as measured by immunoassays, ligand binding assays or Scatchard plot analysis, and induction of cell proliferation or migration as measured by BrdU labeling, cell counting experiments, or quantitative assays for DNA synthesis such as $^3$H-thymidine incorporation. Examples of biological activity for sFlt-1 include binding to PlGF and VEGF as measured by immunoassays, ligand binding assays, or Scatchard plot analysis. Additional examples of assays for biological activity for each of the polypeptides are described herein. As used herein, an alteration includes a 10% change in biological activity, preferably a 25% change, more preferably a 40% change, and most preferably a 50% or greater change in biological activity.

By "antisense nucleobase oligomer" is meant a nucleobase oligomer, regardless of length, that is complementary to the coding strand or mRNA of an sFlt-1 gene. By a "nucleobase oligomer" is meant a compound that includes a chain of at least eight nucleobases, preferably at least twelve, and most preferably at least sixteen bases, joined together by linkage groups. Included in this definition are natural and non-natural oligonucleotides, both modified and unmodified, as well as oligonucleotide mimetics such as Protein Nucleic Acids, locked nucleic acids, and arabinonucleic acids. Numerous nucleobases and linkage groups may be employed in the nucleobase oligomers of the invention, including those described in U.S. Patent Application Nos. 20030114412 and 20030114407, incorporated herein by reference. The nucleobase oligomer can also be targeted to the translational start and stop sites. Preferably the antisense nucleobase oligomer comprises from about 8 to 30 nucleotides. The antisense nucleobase oligomer can also contain at least 40, 60, 85, 120, or more consecutive nucleotides that are complementary to sFlt-1 mRNA or DNA, and may be as long as the full-length mRNA or gene.

By "body mass index" is meant a number, derived by using height and weight measurements, that gives a general indication of whether or not weight falls within a healthy range. The formula generally used to determine the body mass index is a person's weight in kilograms divided by a person's height in meters squared or weight $(kg)/(height (m))^2$.

By "cardiovascular condition" is meant an event or disorder of the cardiovascular system. Non-limiting examples of cardiovascular conditions include atherosclerosis, primary myocardial infarction, secondary myocardial infarction, angina pectoris (including both stable and unstable angina), congestive heart failure, sudden cardiac death, cerebral infarction, restenosis, syncope, ischemia, reperfusion injury, vascular occlusion, carotid obstructive disease, transient ischemic attack, and the like.

By "compound" is meant any small molecule chemical compound, antibody, nucleic acid molecule, or polypeptide, or fragments thereof.

By "chimeric antibody" is meant a polypeptide comprising at least the antigen-binding portion of an antibody molecule linked to at least part of another protein (typically an immunoglobulin constant domain).

By "double-stranded RNA (dsRNA)" is meant a ribonucleic acid molecule comprised of both a sense and an anti-sense strand. dsRNAs are typically used to mediate RNA interference.

By "expression" is meant the detection of a gene or polypeptide by standard art known methods. For example, polypeptide expression is often detected by western blotting, DNA expression is often detected by Southern blotting or polymerase chain reaction (PCR), and RNA expression is often detected by northern blotting, PCR, or RNAse protection assays.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "gestational age" is meant a reference to the age of the fetus, counting from the first day of the mother's last menstrual period usually referred to in weeks.

By a "history of pre-eclampsia or eclampsia" is meant a previous diagnosis of pre-eclampsia or eclampsia or pregnancy induced hypertension in the subject themselves or in a related family member.

By "homologous" is meant any gene or protein sequence that bears at least 30% homology, more preferably 40%, 50%, 60%, 70%, 80%, and most preferably 90% or more homology to a known gene or protein sequence over the length of the comparison sequence. A "homologous" protein can also have at least one biological activity of the comparison protein. For polypeptides, the length of comparison sequences will generally be at least 16 amino acids, preferably at least 20 amino acids, more preferably at least 25 amino acids, and most preferably 35 amino acids or more. For nucleic acids, the length of comparison sequences will generally be at least 50 nucleotides, preferably at least 60 nucleotides, more preferably at least 75 nucleotides, and most preferably at least 110 nucleotides. "Homology" can also refer to a substantial similarity between an epitope used to generate antibodies and the protein or fragment thereof to which the antibodies are directed. In this case, homology refers to a similarity sufficient to elicit the production of antibodies that can specifically recognize the protein at issue.

By "humanized antibody" is meant an immunoglobulin amino acid sequence variant or fragment thereof that is capable of binding to a predetermined antigen. Ordinarily, the antibody will contain both the light chain as well as at least the variable domain of a heavy chain. The antibody also may include the CH1, hinge, CH2, CH3, or CH4 regions of the heavy chain. The humanized antibody comprises a framework region (FR) having substantially the amino acid sequence of a human immunoglobulin and a complementarity determining region (CDR) having substantially the amino acid sequence of a non-human immunoglobulin (the "import" sequences).

Generally, a humanized antibody has one or more amino acid residues introduced into it from a source that is non-human. In general, the humanized antibody will comprise substantially all of at least one, and typically two, variable domains (Fab, Fab', F(ab')$_2$, Fabc, Fv) in which all or substantially all of the CDR regions correspond to those of a non-human immunoglobulin and all or substantially all of the FR regions are those of a human immunoglobulin consensus sequence. The humanized antibody optimally will comprise at least a portion of an immunoglobulin constant region (Fc), typically that of a human immunoglobulin. By "complementarity determining region (CDR)" is meant the three hypervariable sequences in the variable regions within each of the immunoglobulin light and heavy chains. By "framework region (FR)" is meant the sequences of amino acids located on either side of the three hypervariable sequences (CDR) of the immunoglobulin light and heavy chains.

The FR and CDR regions of the humanized antibody need not correspond precisely to the parental sequences, e.g., the import CDR or the consensus FR may be mutagenized by substitution, insertion or deletion of at least one residue so that the CDR or FR residue at that site does not correspond to either the consensus or the import antibody. Such mutations, however, will not be extensive. Usually, at least 75%, preferably 90%, and most preferably at least 95% of the humanized antibody residues will correspond to those of the parental FR and CDR sequences.

By "hybridize" is meant pair to form a double-stranded molecule between complementary polynucleotide sequences, or portions thereof, under various conditions of stringency. (See, e.g., Wahl and Berger (1987) *Methods Enzymol.* 152:399; Kimmel, *Methods Enzymol.* 152:507, 1987.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196:180, 1977); Grunstein and Hogness (*Proc. Natl. Acad. Sci.*, USA 72: 3961, 1975); Ausubel et al. (*Current Protocols in Molecular Biology*, Wiley Interscience, New York, 2001); Berger and Kimmel (*Guide to Molecular Cloning Techniques*, 1987, Academic Press, New York); and Sambrook et al., *Molecular Cloning: A Laboratory Manual*, Cold Spring Harbor Laboratory Press, New York.

By "intrauterine growth retardation (IUGR)" is meant a syndrome resulting in a birth weight which is less that 10 percent of the predicted fetal weight for the gestational age of the fetus. The current World Health Organization criterion for low birth weight is a weight less than 2,500 gm (5 lbs. 8 oz.) or below the 10$^{th}$ percentile for gestational age according to U.S. tables of birth weight for gestational age by race, parity, and infant sex (Zhang and Bowes, *Obstet. Gynecol.* 86:200-208, 1995). These low birth weight babies are also referred to as "small for gestational age (SGA)". Pre-eclampsia is a condition known to be associated with IUGR or SGA.

By "metric" is meant a measure. A metric may be used, for example, to compare the levels of a polypeptide or nucleic acid molecule of interest. Exemplary metrics include, but are not limited to, mathematical formulas or algorithms, such as ratios. The metric to be used is that which best discriminates between levels of sFlt-1, VEGF, or PlGF in a subject having pre-eclampsia or eclampsia and a normal control subject. Depending on the metric that is used, the diagnostic indicator of eclampsia or pre-eclampsia may be significantly above or below a reference value (e.g., from a control subject not having pre-eclampsia or eclampsia).

sFlt-1 level is measured by measuring the amount of free, bound (i.e., bound to growth factor), or total sFlt-1 (bound +free). VEGF or PlGF levels are determined by measuring the amount of free PlGF or free VEGF (i.e., not bound to sFlt-1). One exemplary metric is [sFlt-1/(VEGF+PlGF)], also referred to as the pre-eclampsia anti-angiogenic index (PAAI).

By "operably linked" is meant that a gene and a regulatory sequence(s) are connected in such a way as to permit gene expression when the appropriate molecules (e.g., transcriptional activator proteins) are bound to the regulatory sequence(s).

By "pharmaceutically acceptable carrier" is meant a carrier that is physiologically acceptable to the treated mammal while retaining the therapeutic properties of the compound with which it is administered. One exemplary pharmaceutically acceptable carrier substance is physiological saline. Other physiologically acceptable carriers and their formulations are known to one skilled in the art and described, for example, in Remington's Pharmaceutical Sciences, ($20^{th}$ edition), ed. A. Gennaro, 2000, Lippincott, Williams & Wilkins, Philadelphia, Pa.

By "placental growth factor (PlGF)" is meant a mammalian growth factor that is homologous to the protein defined by GenBank accession number P49763 and that has PlGF biological activity. PlGF is a glycosylated homodimer belonging to the VEGF family and can be found in two distinct isoforms through alternative splicing mechanisms. PlGF is expressed by cyto- and syncytiotrophoblasts in the placenta and PlGF biological activities include induction of proliferation, migration, and activation of endothelial cells, particularly trophoblast cells.

By "polymorphism" is meant a genetic variation, mutation, deletion or addition in an sFlt-1, PlGF, or VEGF nucleic acid molecule that is indicative of a predisposition to develop the conditions. Such polymorphisms are known to the skilled artisan and are described by Parry et al. (*Eur. J. Immunogenet.* 26:321-3, 1999). A polymorphism may be present in the promoter sequence, an open reading frame, intronic sequence, or untranslated 3' region of an sFlt-1 gene.

By "pre-eclampsia" is meant the multi-system disorder that is characterized by hypertension with proteinuria or edema, or both, glomerular dysfunction, brain edema, liver edema, or coagulation abnormalities due to pregnancy or the influence of a recent pregnancy. Pre-eclampsia generally occurs after the $20^{th}$ week of gestation. Pre-eclampsia is generally defined as some combination of the following symptoms: (1) a systolic blood pressure (BP)>140 mmHg and a diastolic BP>90 mmHg after 20 weeks gestation (generally measured on two occasions, 4-168 hours apart), (2) new onset proteinuria (1+ by dipstik on urinanaysis, >300 mg of protein in a 24-hour urine collection, or a single random urine sample having a protein/creatinine ratio>0.3), and (3) resolution of hypertension and proteinuria by 12 weeks postpartum. Severe pre-eclampsia is generally defined as (1) a diastolic BP>110 mmHg (generally measured on two occasions, 4-168 hours apart) or (2) proteinuria characterized by a measurement of 3.5 g or more protein in a 24-hour urine collection or two random urine specimens with at least 3+ protein by dipstick. In pre-eclampsia, hypertension and proteinuria generally occur within seven days of each other. In severe pre-eclampsia, severe hypertension, severe proteinuria and HELLP syndrome (hemolysis, elevated liver enzymes, low platelets) or eclampsia can occur simultaneously or only one symptom at a time. Occasionally, severe pre-eclampsia can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral edema and cerebral hemorrhage). The etiology of the seizures is thought to be secondary to the development of cerebral edema and focal spasm of small blood vessels in the kidney.

By "pre-eclampsia anti-angiogenesis index (PAAI)" is meant the ratio of sFlt-1/JVEGF+PlGF used as an indicator of anti-angiogenic activity. A PAAI greater than 10, more preferably greater than 20, is considered to be indicative of pre-eclampsia or risk of pre-eclampsia.

By "protein" or "polypeptide" or "polypeptide fragment" is meant any chain of more than two amino acids, regardless of post-translational modification (e.g., glycosylation or phosphorylation), constituting all or part of a naturally occurring polypeptide or peptide, or constituting a non-naturally occurring polypeptide or peptide.

By "reduce or inhibit" is meant the ability to cause an overall decrease preferably of 20% or greater, more preferably of 50% or greater, and most preferably of 75% or greater, in the level of protein or nucleic acid, detected by the aforementioned assays (see "expression"). In embodiments that relate to the use of antisense nucleobase oligomers or RNA interference to reduce or inhibit the levels of protein or nucleic acid, the % reduction or inhibition is determined by comparing the levels in the treated sample to the levels in a sample not treated with antisense nucleobase oligomers or dsRNA.

By "reference sample" is meant a sample taken from a subject prior to the time of the test sample, a pregnant subject not having pre-eclampsia or eclampsia, a subject that is pregnant but the sample was taken early in pregnancy (e.g., in the first or second trimester or before the detection of pre-eclampsia or eclampsia), a subject that is pregnant but does not have pre-eclampsia or eclampsia and has no history of pre-eclampsia or eclampsia, or a subject that is not pregnant. A reference sample can also be a purified polypeptide (e.g., PlGF, VEGF, or sFlt-1) at a concentration known to be a normal concentration not diagnostic of pre-eclampsia or eclampsia. For example, urinary PlGF concentrations during normal pregnancy may range from 400-800 pg/ml, whereas those with active preeclampsia may be below 200 pg/ml during mid-gestation. A level of urinary PlGF below 400 pg/ml or below 200 pg/ml is indicative of pre-eclampsia or a propensity to develop preeclampsia. A "reference sample" can also be a reference standard or level. By "reference standard or level" is meant a value or number derived from a reference sample. The reference standard or level can also be a value or number derived from a normal subject that is matched to the sample subject by at least one of the following criteria: gestational age of the fetus, maternal age, maternal blood pressure prior to pregnancy, maternal blood pressure during pregnancy, BMI of the mother, weight of the fetus, prior diagnosis of pre-eclampsia or eclampsia, and a family history of pre-eclampsia or eclampsia. A reference value can also be used which is determined based on the values of a particular polypeptide in a reference sample.

By "small interfering RNAs (siRNAs)" is meant an isolated dsRNA molecule, preferably greater than 10 nucleotides in length, more preferably greater than 15 nucleotides in length, and most preferably greater than 19 nucleotides in length that is used to identify the target gene or mRNA to be degraded. A range of 19-25 nucleotides is the most preferred size for siRNAs. siRNAs can also include short hairpin RNAs in which both strands of an siRNA duplex are included within a single RNA molecule. siRNA includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides. Such alterations can include the addition of non-nucleotide material, such as to the end(s) of the 21 to 23 nt RNA or internally (at one or more nucleotides of the RNA). In a preferred embodiment, the RNA molecules contain a 3'hydroxyl group.

Nucleotides in the RNA molecules of the present invention can also comprise non-standard nucleotides, including non-naturally occurring nucleotides or deoxyribonucleotides. Collectively, all such altered RNAs are referred to as analogs of RNA. siRNAs of the present invention need only be sufficiently similar to natural RNA that it has the ability to mediate RNA interference (RNAi). As used herein, RNAi refers to the ATP-dependent targeted cleavage and degradation of a specific mRNA molecule through the introduction of small interfering RNAs or dsRNAs into a cell or an organism. As used herein "mediate RNAi" refers to the ability to distinguish or identify which RNAs are to be degraded.

By "soluble Flt-1 (sFlt-1)" (also known as sVEGF-R 1) is meant the soluble form of the Flt-1 receptor, that is homologous to the protein defined by GenBank accession number U01134, and that has sFlt-1 biological activity. The biological activity of an sFlt-1 polypeptide may be assayed using any standard method, for example, by assaying sFlt-1 binding to VEGF. sFlt-1 lacks the transmembrane domain and the cytoplasmic tyrosine kinase domain of the Flt-1 receptor. sFlt-1 can bind to VEGF and PlGF with high affinity, but it cannot induce proliferation or angiogenesis and is therefore functionally different from the Flt-1 and KDR receptors. sFlt-1 was initially purified from human umbilical endothelial cells and later shown to be produced by trophoblast cells in vivo. As used herein, sFlt-1 includes any sFlt-1 family member or isoform. In additional embodiments, sFlt-1 can also mean degradation products or fragments that result from enzymatic cleavage of the Flt-1 receptor and that maintain sFlt-1 biological activity. In one example, specific metalloproteinases released from the placenta may cleave the extracellular domain of Flt-1 receptor to release the N-terminal portion of Flt-1 into circulation.

By "specifically binds" is meant a compound or antibody which recognizes and binds a polypeptide of the invention but that does not substantially recognize and bind other molecules in a sample, for example, a biological sample, which naturally includes a polypeptide of the invention. In one example, an antibody that specifically binds sFlt-1 does not bind Flt-1.

By "subject" is meant a mammal, including, but not limited to, a human or non-human mammal, such as a bovine, equine, canine, ovine, or feline. Included in this definition are pregnant, post-partum, and non-pregnant mammals.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein. Preferably, the amino acid sequence is at least 70%, more preferably at least about 80%, and most preferably at least about 90% homologous to another amino acid sequence. Methods to determine identity are available in publicly available computer programs. Computer program methods to determine identity between two sequences include, but are not limited to, the GCG program package (Devereux et al., *Nucleic Acids Research* 12:387, 1984), BLASTP, BLASTN, and FASTA (Altschul et al., *J. Mol. Biol.* 215:403 (1990). The well-known Smith Waterman algorithm may also be used to determine identity. The BLAST program is publicly available from NCBI and other sources (*BLAST Manual*, Altschul, et al., NCBI NLM NIH, Bethesda, Md. 20894; BLAST 2.0 at http://www.ncbi.nlm.nih.gov/blast/). These software programs match similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "symptoms of pre-eclampsia" is meant any of the following: (1) a systolic blood pressure (BP)>140 mmHg and a diastolic BP>90 mmHg after 20 weeks gestation, (2) new onset proteinuria (1+by dipstik on urinanaysis, >300 mg of protein in a 24 hour urine collection, or random urine protein/creatinine ratio>0.3), and (3) resolution of hypertension and proteinuria by 12 weeks postpartum. The symptoms of pre-eclampsia can also include renal dysfunction and glomerular endotheliosis or hypertrophy. By "symptoms of eclampsia" is meant the development of any of the following symptoms due to pregnancy or the influence of a recent pregnancy: seizures, coma, thrombocytopenia, liver edema, pulmonary edema, and cerebral edema.

By "therapeutic amount" is meant an amount that when administered to a patient suffering from pre-eclampsia or eclampsia is sufficient to cause a qualitative or quantitative reduction in the symptoms of pre-eclampsia or eclampsia as described herein. A "therapeutic amount" can also mean an amount that when administered to a patient suffering from pre-eclampsia or eclampsia is sufficient to cause a reduction in the expression levels of sFlt-1 or an increase in the expression levels of VEGF or PlGF as measured by the assays described herein.

By "treating" is meant administering a compound or a pharmaceutical composition for prophylactic and/or therapeutic purposes. To "treat disease" or use for "therapeutic treatment" refers to administering treatment to a subject already suffering from a disease to improve the subject's condition. Preferably, the subject is diagnosed as suffering from pre-eclampsia or eclampsia based on identification of any of the characteristic symptoms described below or the use of the diagnostic methods described herein. To "prevent disease" refers to prophylactic treatment of a subject who is not yet ill, but who is susceptible to, or otherwise at risk of, developing a particular disease. Preferably a subject is determined to be at risk of developing pre-eclampsia or eclampsia using the diagnostic methods described herein. Thus, in the claims and embodiments, treating is the administration to a mammal either for therapeutic or prophylactic purposes.

By "trophoblast" is meant the mesectodermal cell layer covering the blastocyst that erodes the uterine mucosa and through which the embryo receives nourishment from the mother; the cells contribute to the formation of the placenta.

By "vascular endothelial growth factor (VEGF)" is meant a mammalian growth factor that is homologous to the growth factor defined in U.S. Pat. Nos. 5,332,671; 5,240,848; 5,194,596; and Charnock-Jones et al. (*Biol. Reproduction,* 48:1120-1128, 1993), and has VEGF biological activity. VEGF exists as a glycosylated homodimer and includes at least four different alternatively spliced isoforms. The biological activity of native VEGF includes the promotion of selective growth of vascular endothelial cells or umbilical vein endothelial cells and induction of angiogenesis. As used herein, VEGF includes any VEGF family member or isoform (e.g. VEGF-A, VEGF-B, VEGF-C, VEGF-D, VEGF-E, VEGF189, VEGF165, or VEGF 121). Preferably, VEGF is the VEGF121 or VEGF165 isoform (Tischer et al., *J. Biol. Chem.* 266, 11947-11954, 1991; Neufed et al. *Cancer Metastasis* 15:153-158, 1996), which is described in U.S. Pat. Nos. 6,447,768; 5,219,739; and 5,194,596, hereby incorporated by reference. Also included are mutant forms of VEGF such as the KDR-selective VEGF and Flt-selective VEGF described in Gille et al. (*J. Biol. Chem.* 276:3222-3230, 2001). As used herein VEGF also includes any modified forms of VEGF such as those described in LeCouter et al. (*Science* 299:890-893, 2003). Although human VEGF is preferred, the invention is not limited to human forms and can include other animal forms of VEGF (e.g. mouse, rat, dog, or chicken).

By "vector" is meant a DNA molecule, usually derived from a plasmid or bacteriophage, into which fragments of DNA may be inserted or cloned. A recombinant vector will contain one or more unique restriction sites, and may be capable of autonomous replication in a defined host or vehicle organism such that the cloned sequence is reproducible. A vector contains a promoter operably linked to a gene or coding region such that, upon transfection into a recipient cell, an RNA is expressed.

Other features and advantages of the invention will be apparent from the following description of the preferred embodiments thereof, and from the claims.

BRIEF DESCRIPTION OF THE DRAWINGS

FIG. 1A shows mRNA expression of placental sFlt-1 from three patients with pre-eclampsia (P1, P2, P3) and three normotensive term pregnancies (N1, N2, N3) as determined by northern blot analysis. The higher band (7.5 kb) is the full length flt-1 mRNA and the lower, more abundant band (3.4 kb) is the alternatively spliced sFlt-1 mRNA. GAPDH is included as a control and the arrowhead indicates 28S RNA. Patients P1 and P2 had severe pre-eclampsia, whereas patient P3 had mild pre-eclampsia. FIG. 1B is a graph showing sFlt-1 levels in serum from patients with mild pre-eclampsia (mild PE), patients with severe pre-eclampsia (severe PE), and normotensive pregnant women at term (normal). sFlt-1 levels were measured by an ELISA performed for sFlt-1 using a commercially available kit (R & D Systems, Minneapolis, Minn.). Patients with pre-term deliveries for other reasons (pre-term) were included as additional controls to rule out gestational age specific changes. The number of patients tested is shown in parenthesis in the X axis. Samples were collected prior to delivery (t=0) and 48 hours after delivery (t=48). FIG. 1C is a graph showing anti-angiogenesis index ratios (PAAI=sFlt-1/(VEGF+PlGF)) ratios at the time of delivery (t=0) as determined by ELISA for all the patients described in FIG. 1B.

FIGS. 2A, 2B, and 2C show assays performed using serum from a normal patient, while FIGS. 2D, 2E, and 2F show assays performed using serum from a patient with pre-eclampsia. In FIG. 2A, t=0 (10% serum from a normal pregnant woman at term); in FIG. 2B, t=48 (10% serum from normal pregnant woman 48 hours after delivery); in FIG. 2C, t=0+exogenous sFlt-1 (10 ng/ml); in FIG. 2D, t=0 (10% serum from pre-eclamptic woman prior to delivery); in FIG. 2E, t=48 (10% serum from pre-eclamptic woman 48 hours after delivery); and in FIG. 2F, t=0+exogenous VEGF(10 ng/ml)+PlGF (10 ng/ml). The tube assay was quantitated and the mean tube length +/− SEM is shown in pixels at the bottom of each panel.

FIG. 3A shows that the increase in relaxation responses of rat renal arterioles to sFlt-1 (S), VEGF (V), PlGF (P) was measured at three different doses. V+ and P+ represent vasodilatory responses of the individual reagents in the presence of sFlt-1 at 100 ng/ml. All experiments were done in 6 different dissected rat renal microvessels and data is shown as mean +/− SEM. The * represents statistical significance with $p<0.01$ as compared to individual reagents alone. FIG. 3B shows the increase in relaxation responses at physiological doses: VEGF 100 pg/ml (V), PlGF 500 pg/ml (P), sFlt-1 10 ng/ml (S), VEGF (100 pg/ml)+PlGF 500 pg/ml (V+P) or VEGF (100 pg/ml)+PlGF 500 pg/ml+sFlt-1 10 ng/ml (V+P+S). All experiments were done in 6 different dissected rat renal microvessels and data is shown as mean +/−SEM. The * represents statistical significance with $p<0.05$ as compared with V+P.

FIGS. 4A and 4B are images showing sFlt-1 induction of glomerular endotheliosis. FIG. 4A is photomicrograph showing hematoxylin and eosin (H & E) staining in a capillary occlusion in the sFlt-1 treated animals with enlarged glomeruli and swollen cytoplasm as compared to controls. "Glomerular endotheliosis" with bubbly cytoplasm is shown in the sFlt-1 treated animals on periodic acid schiff (PAS) stain. All light microscopy pictures were taken at 60×, original magnification. FIG. 4B is an electron micrograph of sFlt-1 treated glomeruli that confirms cytoplasmic swelling of the endocapillary cells. The immunofluorescence (IF) for fibrin pictures were taken at 40× and the EM pictures were taken at 2400×, original magnification. All figures were reproduced at identical magnifications.

FIG. 5A is a graph showing the mean serum concentrations in pg/ml for normotensive controls (lighter line with open triangles), cases before pre-eclampsia (filled circles), and cases after pre-eclampsia -"endpoint" specimens-(filled squares) within 4-5 week gestational age windows prior to onset of labor. Brackets indicate standard error of the mean. Asterisks indicate significant differences with respect to control specimens within the same gestational age window after logarithmic transformation: $*p<0.05$, $p<0.01$, $*p<0.001$. FIG. 5B is a graph showing the mean serum concentrations of sFlt1 in pg/ml for cases before and after the onset of pre-eclampsia within intervals of weeks before pre-eclampsia. PE indicates the arithmetic mean of 43 endpoint specimens (obtained on or following onset of pre-eclampsia). Mean gestational age (days) is indicated in parentheses below each time interval. The horizontal line indicates the level in the endpoint specimens. The vertical lines demarcate the period ≦5 weeks before pre-eclampsia. FIG. 5C is a graph showing the mean serum concentrations of sFlt-1 in pg/ml by gestational age windows for normotensive controls and cases before pre-eclampsia, after excluding specimens obtained within 5 weeks of onset of pre-eclampsia. There are no significant differences.

FIG. 6A is a graph showing PlGF levels in all specimens obtained before labor and delivery. Brackets indicate standard error of the mean. Asterisks indicate significant differences with respect to control specimens within the same interval after logarithmic transformation: $p<0.01$, $*p<0.001$. FIG. 6B is a graph showing the mean serum concentrations of PlGF in pg/ml for cases before and after onset of pre-eclampsia within intervals of weeks before pre-eclampsia. PE indicates the arithmetic mean of 43 endpoint specimens (obtained on or following onset of pre-eclampsia). Mean gestational age (days) is indicated in parentheses below each time interval. The horizontal line indicates the level in the endpoint specimens. The vertical lines demarcate the period ≦5 weeks before pre-eclampsia.

FIG. 6C is a graph showing the mean serum concentrations of PlGF in pg/ml by gestational age windows for normotensive controls and cases onset of pre-eclampsia.

FIG. 7A is a graph showing the arithmetic mean serum concentrations of sFlt-1 (black bars) and PlGF (white bars) at 23-32 weeks of gestation in controls and cases (before onset of clinical disease) with mild pre-eclampsia, severe pre-eclampsia, pre-eclampsia with onset <37 weeks, pre-eclampsia with a small for gestational age (SGA) infant, and pre-eclampsia with onset <34 weeks. Numbers of specimens are recorded below each column pair. Adjustment for gestational age and body mass index resulted in minor changes with no affect on level of significance. FIG. 7B is a graph showing the arithmetic mean serum concentrations of sFlt-1 (black bars) and PlGF (white bars) at 33-41 weeks of gestation in controls and cases (before onset of clinical disease) with mild pre-eclampsia, severe pre-eclampsia, pre-eclampsia with onset <37 weeks, and pre-eclampsia with an SGA infant. Numbers of specimens are recorded below each column pair. Adjustment for gestational age and body mass index resulted in minor changes.

FIG. 9A is a graph showing the mean PlGF concentrations before and after the onset of clinical pre-eclampsia according to gestational age. I bars represent standard errors. FIG. 9B is a graph showing the mean PlGF expressed as pg per mg creatinine before and after the onset of clinical pre-eclampsia. I bars represent standard errors. FIG. 9C is a graph showing the mean PlGF concentrations before and after the onset of clinical pre-eclampsia, using only first morning urine specimens. I bars represent standard errors. FIG. 9D is a graph showing the mean PlGF concentrations before and after the onset of clinical pre-eclampsia, using only random urine specimens. I bars represent standard errors.

FIG. 12A shows urinary PlGF concentrations. FIG. 12B shows serum ratios of sFlt1 to PlGF.

DETAILED DESCRIPTION

Figure 1:
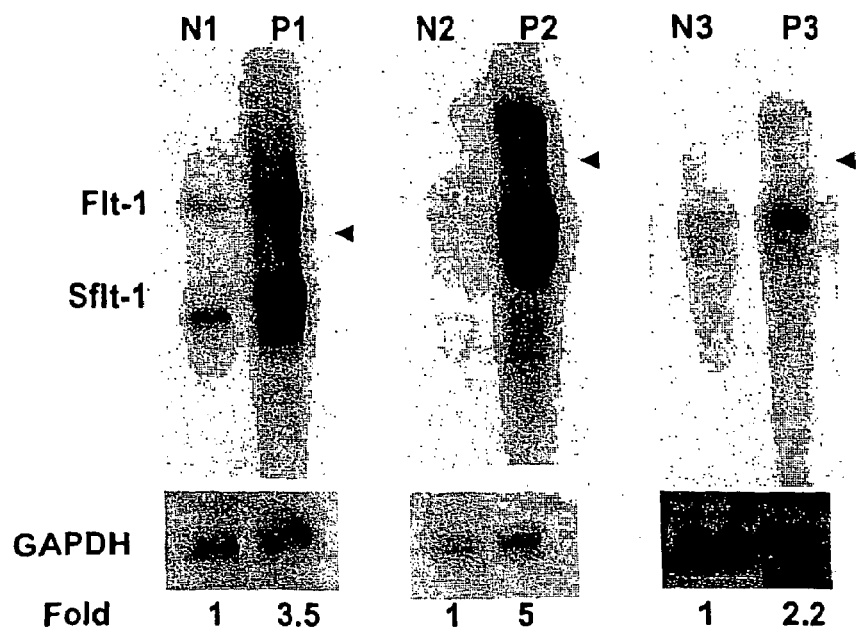
FIG. 1 is an autoradiogram depicting sFlt-1 mRNA and protein expression levels in pre-eclampsia.
Figure 1:
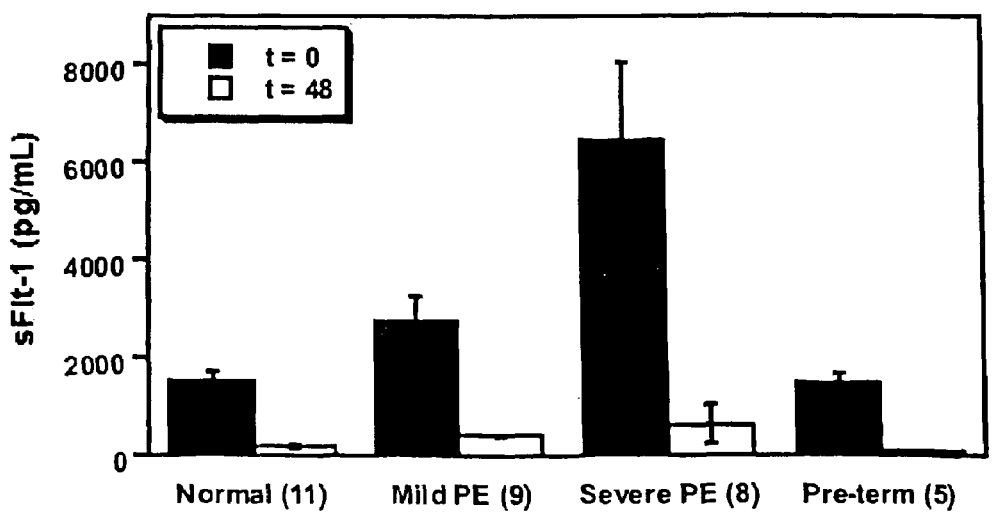
Figure 1:
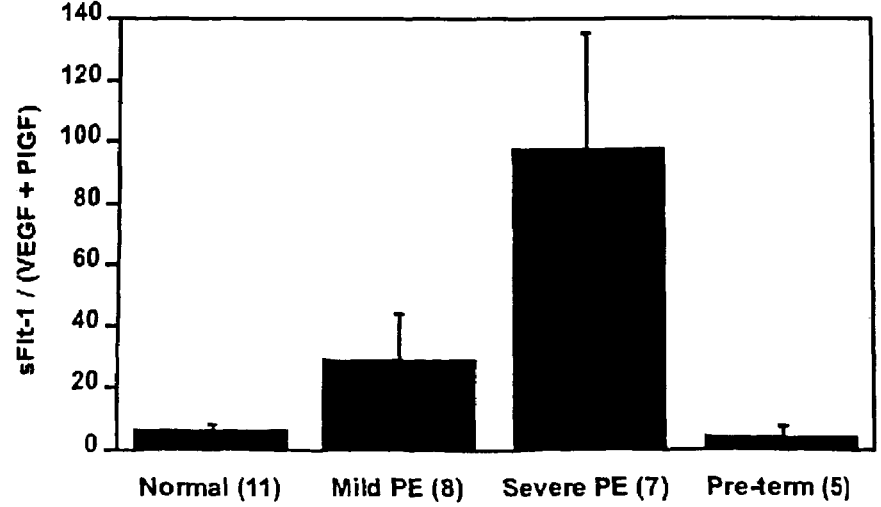

We have discovered that sFlt-1 levels are elevated in blood serum samples taken from pre-eclamptic women. sFlt-1 binds to VEGF and PlGF with high affinity and blocks the mitogenic and angiogenic activity of these growth factors. Thus, sFlt-1 is an excellent diagnostic marker for pre-eclampsia and VEGF and PlGF may be used to treat pre-eclampsia. Furthermore, we have discovered therapeutic agents that interfere with sFlt-1 binding to purified VEGF or PlGF, or agents that increase levels of biologically active VEGF or PlGF, can be used to treat or prevent pre-eclampsia or eclampsia in a subject. Such agents include, but are not limited to, antibodies to sFlt-1, oligonucleotides for antisense or RNAi that reduce levels of sFlt-1, compounds that increase the levels of VEGF or PlGF, and small molecules that bind sFlt-1 and block the growth factor binding site. The invention also features methods for measuring levels of growth factors; the methods can be used as diagnostic tools for early detection of pre-eclampsia or an increased risk of developing pre-eclampsia or eclampsia.

While the detailed description presented herein refers specifically to sFlt-1, VEGF, or PlGF, it will be clear to one skilled in the art that the detailed description can also apply to sFlt-1, VEGF, or PlGF family members, isoforms, and/or variants, and to growth factors shown to bind sFlt-1. The following examples are for the purposes of illustrating the invention, and should not be construed as limiting.

EXAMPLE 1

Increased Levels of sFlt-1 mRNA and Protein in Pregnant Women With Pre-Eclampsia In an attempt to identify novel secreted factors playing a pathologic role in pre-eclampsia, we performed gene expression profiling of placental tissue from women with and without pre-eclampsia using Affymetrix U95A microarray chips. We found that the gene for sFlt-1 was upregulated in women with pre-eclampsia.

In order to confirm the upregulation of sFlt-1 in pre-eclampsia, we performed Northern blots to analyze the placental sFlt-1 mRNA levels (FIG. 1A) and ELISA assays to measure serum protein levels of sFlt-1 (FIG. 1B) in pre-eclamptic pregnant women as compared with normotensive pregnant women. Pre-eclampsia was defined as (1) a systolic blood pressure (BP)>140 mmHg and a diastolic BP>90 mmHg after 20 weeks gestation, (2) new onset proteinuria (1+by dipstik on urinanalysis, >300 mg of protein in a 24 hour urine collection, or random urine protein/creatinine ratio >0.3, and (3) resolution of hypertension and proteinuria by 12 weeks post-partum. Patients with underlying hypertension, proteinuria, or renal disease were excluded. Patients were divided into mild and severe pre-eclampsia based on the presence or absence of nephritic range proteinuria (>3 g of protein on a 24 hour urine collection or urine protein/creatinine ratio greater than 3.0). The mean urine protein/creatinine ratios in the mild pre-eclampsia group were 0.94+/−0.2 and in the severe pre-eclampsia group were 7.8 +/−2.1. The mean gestational ages of the various groups were as follows: normal 38.8+/−0.2 weeks, mild pre-eclampsia 34+/−1.2 weeks, severe pre-eclampsia 31.3 +/−0.6 weeks, and pre-term 29.5+/−2.0 weeks. Placental samples were obtained immediately after delivery. Four random samples were taken from each placenta, placed in RNAlater stabilization solution (Ambion, Austin, Tex.) and stored at −70' C. RNA isolation was performed using Qiagen RNAeasy Maxi Kit (Qiagen, Valencia, Calif.).

We detected an increase in both placental sFlt-1 mRNA and maternal serum sFlt-1 protein in pre-eclamptic pregnant women as compared to normotensive pregnant women. The average serum level of sFlt-1 was almost four times higher in the severe pre-eclampsia patients as compared to normal control pregnant women. To exclude the possibility that this effect was due to the earlier gestational age of the pre-eclamptic cases, we also measured sFlt-1 levels in gestationally matched normotensive women delivering pre-maturely for other reasons (gestational ages 23-36 weeks), and we found no significant difference in this group compared with normotensive term pregnancies. The probes used for northern blots were obtained by PCR and included a 500 bp fragment in the coding region from pUC 118 human flt-1 cDNA, and a GAPDH cDNA that was used as normalization control.

In normal pregnancy there is a balance between pro- and anti-angiogenic factors secreted by the placenta that is necessary for adequate placental development. We hypothesized that in pre-eclampsia, increased production of sFlt-1 and decreased production of VEGF and PlGF shifts the balance in favor of anti-angiogenesis. To address the net anti-angiogenic activity we measured VEGF and PlGF serum levels and found that PlGF and VEGF serum levels were lower in patients with pre-eclampsia as compared to normal control patients (mean PlGF, 235.3+/−45.3 pg/ml versus 464+/−116.6 pg/ml) as has been described (Tidwell et al., Am. J. Obstet. Gynecol., 184: 1267-1272, 2001). When we incorporated sFlt-1, VEGF and PlGF levels into an anti-angiogenic index, or PAAI, as an indicator of net anti-angiogenic activity, we found that we could clearly separate the pre-eclamptic from the normal patients and that the PAAI seemed to correlate with severity of the pre-eclampsia (FIG. 1C). This PAAI can be used as a diagnostic tool for the detection of pre-eclampsia in pregnant women.

EXAMPLE 2

Serum from Women with Pre-Eclampsia Inhibits Angiogenesis in an In Vitro Endothelial Tube Assay We hypothesized that excess circulating sFlt-1 in patients with pre-eclampsia causes endothelial dysfunction and leads to an anti-angiogenic state. To address this, we used an endothelial tube assay as an in vitro model of angiogenesis. Growth factor reduced Matrigel (7 mg/mL, Collaborative Biomedical Products, Bedford, Mass.) was placed in wells (100 µl/well) of a pre-chilled 48-well cell culture plate and incubated at 37° C. for 25-30 minutes to allow polymerization. Human umbilical vein endothelial cells (30,000+in 300 µl of endothelial basal medium with no serum, Clonetics, Walkersville, Md.) at passages 3-5 were treated with 10% patient serum, plated onto the Matrigel coated wells, and incubated at 37° C. for 12-16 hours. Tube formation was then assessed through an inverted phase contrast microscope at 4× (Nikon Corporation, Tokyo, Japan) and quantitatively analyzed (tube area and total length) using the Simple PCI imaging analysis software.

Figure 2:
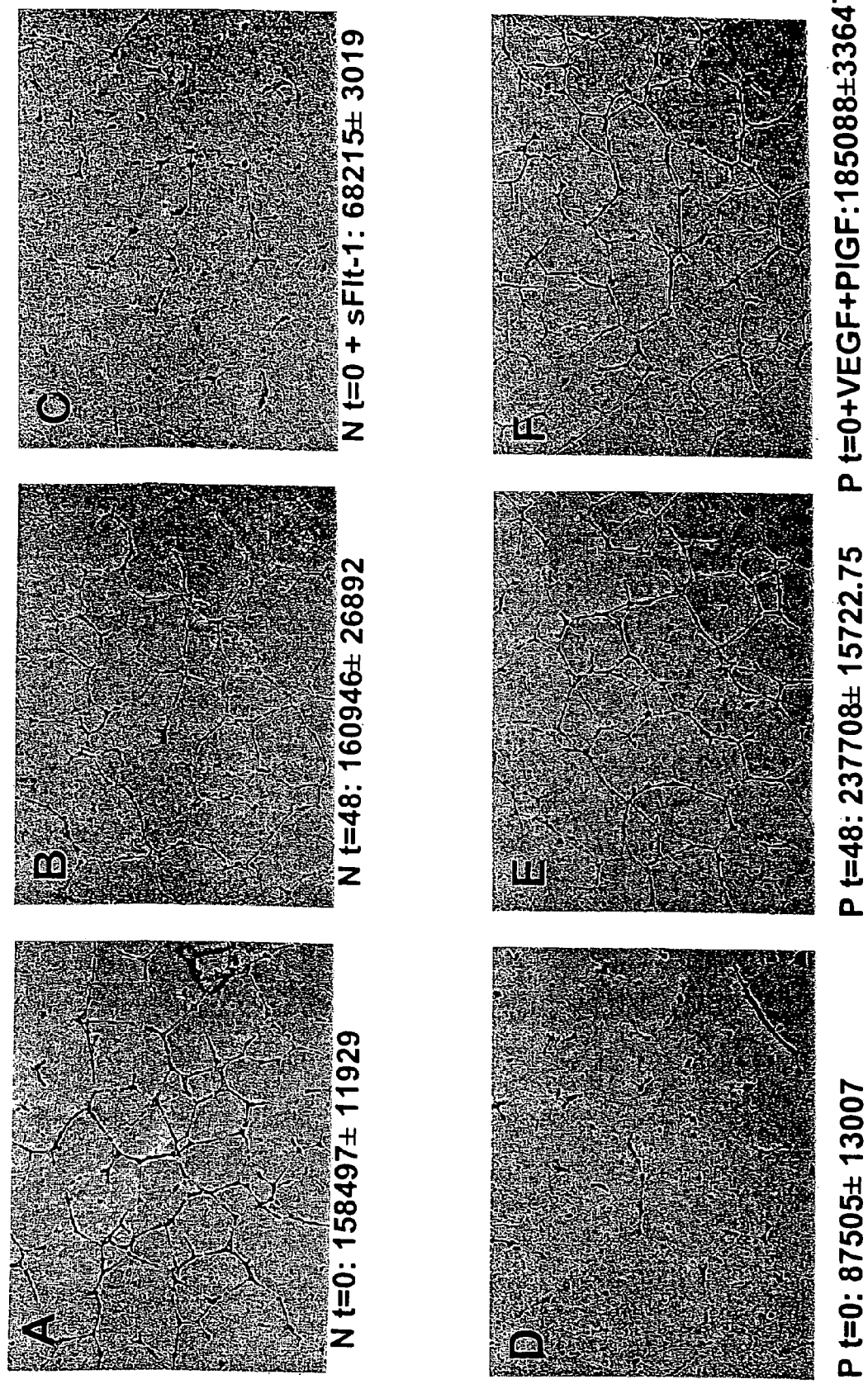
FIGS. 2A-2F are photomicrographs showing the anti-angiogenic effect of excess sFlt-1 in pre-eclampsia. Endothelial tube assays were performed using serum from four normal pregnant controls and four patients with pre-eclampsia. A representative experiment from one normal control and one patient with pre-eclampsia is shown.

The conditions of the tube formation assay were adjusted such that normal human umbilical vein endothelial cells form tubes only in the presence of exogenous growth factors such as VEGF. Under these conditions, we found that while serum from normotensive women induced endothelial cells to form regular tube-like structures, serum from women with pre-eclampsia inhibited tube formation (FIG. 2). Notably, by 48 hours post-partum this anti-angiogenic effect had disappeared suggesting that the inhibition of tubes noted with the serum from pre-eclampsia patients was probably due to a circulating factor released by the placenta. When sFlt-1 was added to normotensive serum at doses similar to those found in patients with pre-eclampsia, tube formation did not occur, mimicking the effects seen with the serum from pre-eclamptic women. When exogenous VEGF and PlGF were added to the assay using pre-eclamptic serum, tube formation was restored (FIG. 2). Recombinant human VEGF, human PlGF, and human Flt-1Fc were used for these assays. These results suggested that the anti-angiogenic properties of pre-eclamptic serum were due to the antagonism of VEGF and PlGF by endogenous sFlt-1. These results also suggested that addition of purified VEGF and/or PlGF can reverse or mitigate the pre-eclamptic condition and can be used therapeutically.

EXAMPLE 3 sFlt-1 Inhibits VEGF and PlGF Induced Vasodilation of Renal Microvessels

The causative role of sFlt-1 in vasoconstriction was determined using an in vitro microvascular reactivity experiment. Microvascular reactivity experiments were done as described previously using rat renal microvessels (Sato et al., J. Surg. Res., 90:138-143, 2000). Kidney artery microvessels (70-1701 m internal diameter) were dissected from rat kidneys using a 10× to 60× dissecting microscope (Olympus Optical, Tokyo, Japan). Microvessels were placed in an isolated microvessel chamber, cannulated with dual glass micropipettes measuring 30-60 µm in diameter, and secured with a 10-0 nylon monofilament suture (Ethicon, Somerville, N.J.). Oxygenated (95% oxygen and 5% carbon dioxide) Krebs' buffer solution warmed to 37° C. was continuously circulated through the vessel chamber and a reservoir containing a total of 100 ml of the solution. The vessels were pressurized to 40 mmHg in a no-flow state using a burette manometer filled with a Krebs' buffer solution. With an inverted microscope (40× to 200×; Olympus CK2, Olympus Optical) connected to video camera, the vessel image was projected onto a black-and-white television monitor. An electronic dimension analyzer (Living System Instrumentation, Burlington, Vt.) was used to measure the internal lumen diameter. Measurements were recorded with a strip-chart recorder (Graphtec, Irvine, Calif.). Vessels were allowed to bathe in the microvessel chamber for at least 30 minutes prior to any intervention. In all experimental groups, the relaxation responses of kidney microvessels were examined after pre-contraction of the microvessels with U46619 (thromboxane agonist) to 40-60% of their baseline diameter at a distending pressure of 40 mmHg. Once the steady-state tone was reached, the responses to various reagents such as VEGF, PlGF, and sFlt-1 were examined. Recombinant rat VEGF, mouse PlGF, and mouse Flt-1 Fc were used for these assays. All drugs were applied extraluminally. Measurements were made when the response had stabilized (usually 2-3 minutes after the drug was administered). One to four interventions were performed on each vessel. The vessels were washed with a Krebs' buffer solution and allowed to equilibrate in a drug-free Krebs' buffer solution for 20-30 minutes between interventions.

Figure 3:
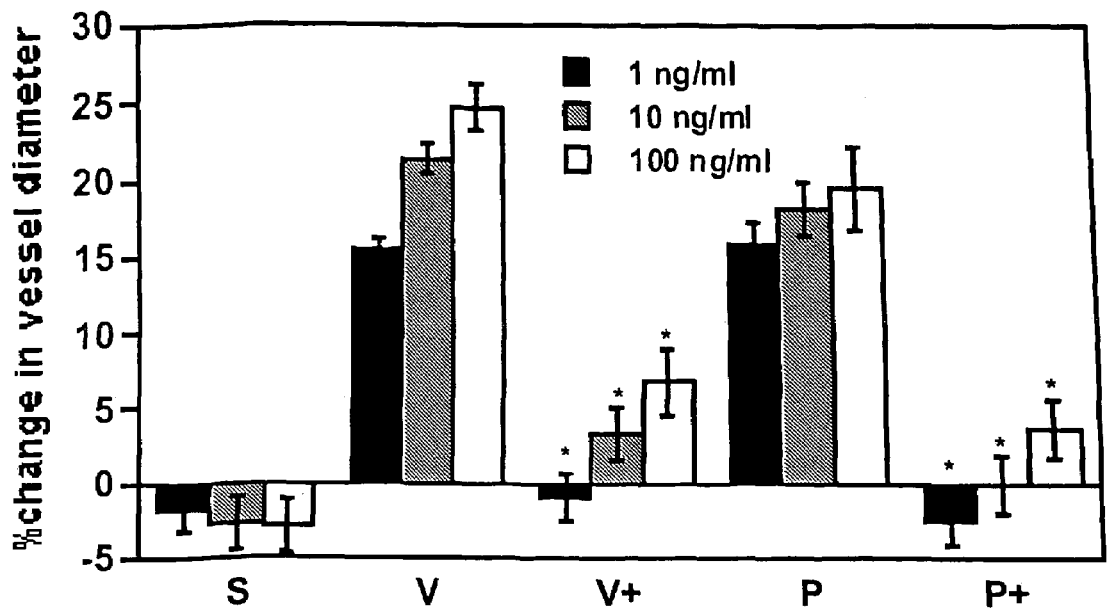
FIGS. 3A and 3B are graphs showing that inhibition of VEGF and PlGF induced vasodilation of renal microvessels by sFlt-1.
Figure 3:
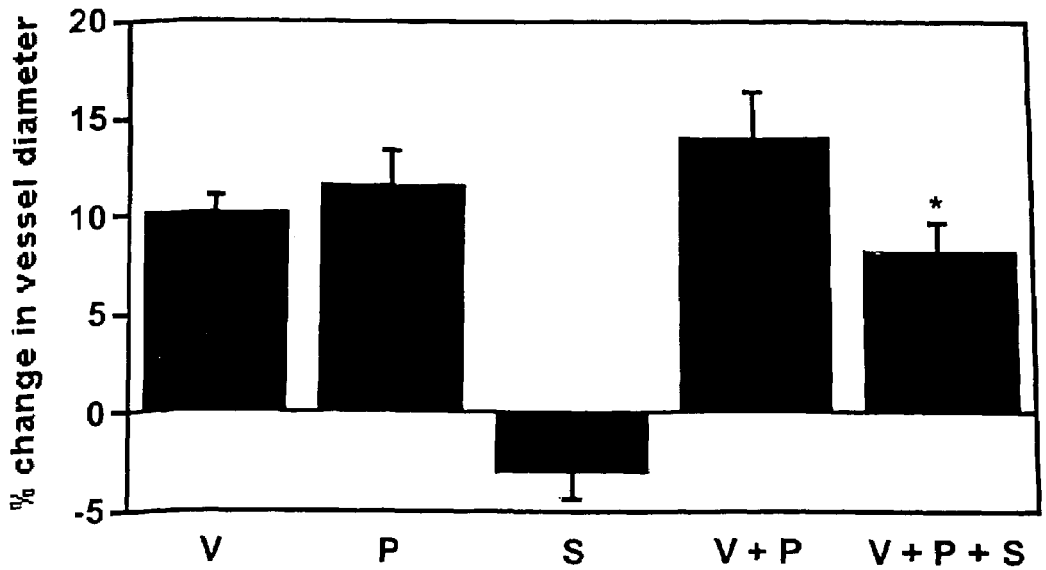

We found that sFlt-1 alone did not cause significant vasoconstriction, however it blocked the dose responsive increase in vasodilation induced by VEGF or PlGF (FIG. 3A). Furthermore, we found that VEGF and PlGF, at physiological levels seen in pregnancy, induced significant dose dependent arteriolar relaxation, and that this effect was blocked by the addition of 10 ng/ml sFlt-1, a concentration observed in severely pre-eclamptic women (FIG. 3B). This result suggested that circulating sFlt-1 in patients with pre-eclampsia may oppose vasorelaxation, thus contributing to hypertension. These results support the conclusion that sFlt-1 is responsible for many of the clinical and pathological symptoms of pre-eclampsia, including hypertension. Inhibition of sFlt-1, through the use of directed antibodies, for example, could reverse the effects of the protein in pre-eclamptic women and such sFlt-1 inhibitors could potentially be used as a therapeutic agent.

EXAMPLE 4

Effects of sFlt-1 in an Animal Model of Pre-Eclampsia

Based on the above results, we hypothesized that the addition of exogenous sFlt-1 would produce hypertension and proteinuria in an animal model. Adenovirus expressing sFlt-1 has been shown to produce sustained systemic sFlt-1 levels associated with significant anti-tumor activity (Kuo et al., *Proc. Natl. Acad. Sci. USA*, 98:4605-4610, 2001). This recombinant adenovirus encoding murine sFlt-1 was injected into the tail vein of pregnant Sprague-Dawley rats on day 8-9 of pregnancy. Adenovirus encoding murine Fc and sFlk1-Fc (fusion protein of mouse VEGF receptor 1 Flk1 ectodomain and Fc protein) in equivalent doses were used as controls. Flk1 has been shown to bind to VEGF, but not PlGF. Hence, sFlk-1 Fc was chosen as a control to help discriminate between the anti-VEGF and the anti-PlGF activity of sFlt1.

Both pregnant and non-pregnant Sprague-Dawley rats were injected with $1\times10^9$ pfu of Ad Fc, Ad sFlt-1, or Ad sFlk-1 Fc by tail vein injections. These adenoviruses have been described previously (Kuo et al., supra) and were generated at the Harvard Vector Core Laboratory. Pregnant rats were injected with the adenoviruses at day 8-9 of pregnancy (early second trimester) and blood pressure was measured at day 16-17 of pregnancy (early third trimester). In non-pregnant animals, BPs were measured at day 8 after injection of the adenoviruses. BPs were measured in the rats after anesthesia with pentobarbital sodium (60 mg/kg, i.p.). The carotid artery was isolated and cannulated with a 3-Fr high-fidelity microtip catheter connected to a pressure transducer (Millar Instruments, Houston, Tex.). The Millar Mikro-Tip catheter was advanced into the artery to record blood pressure. Blood pressure and heart rate were recorded in by chart-strip recorder (model 56-1x40-006158, Gould Instrument Systems, Cleveland, Ohio) and averaged over a 10-minute period. Blood, tissue, and urine samples were then obtained before euthanasia. Urinary albumin was measured by standard dipstick and quantitated by competitive enzyme-linked immunoassay (ELISA) as has been described elsewhere (Cohen et al., *Kidney Intl.*, 45:1673-1679, 1994). Urinary creatinine was measured by a picric acid colorimetric procedure kit (Sigma, St. Louis, Mo.). We measured intrarterial blood pressures in the early third trimester of the pregnancy to mimic the natural pathology of pre-eclampsia. These experiments were also performed in non-pregnant female Sprague-Dawley rats to determine if the effects of sFlt-1 is direct or indirect through its effects on the placenta. Systemic levels of sFlt-1 on the day of blood pressure measurement were confirmed by Western blot analysis to be in the range of 25-350 ng/mL in the various sFlt-1 treated animals on the day of BP measurements. Blood pressure and proteinuria in the different experimental groups is shown in Table 1.

TABLE 1

Blood Pressure and Proteinuria in Rats

| | N | MAP (mmHg) | U alb:cr ratio |
|---|---|---|---|
| Fc (P) | 5 | 75.6 ± 11.1 | 62 ± 21 |
| sFlt-1 (P) | 4 | 109.0 ± 19.3* | 6923 ± 658* |
| sFlk-1Fc (P) | 4 | 72.8 ± 14.7 | 50 ± 32 |
| Fc (NP) | 5 | 89.3 ± 5.7 | 138 ± 78 |
| sFlt-1 (NP) | 6 | 117.9 ± 12.9* | 12947 ± 2776* |
| sFlk-1Fc (NP) | 4 | 137.3 ± 2.3* | 2269 ± 669* |

Pregnant (P) and nonpregnant (NP) rats were administered adenovirus expressing Fc (control), sFlt-1, or sFlk-1Fc protein.
Mean arterial blood pressure (MAP = diastolic + ⅓ pulse pressure in mmHg) ± S.E.M and urine albumin:Cr ratio (mg of albumin per gram of creatinine) ± S.E.M were measured eight days later, corresponding to the early third trimester in the pregnant rats.
N = the number of animals in each experimental group.
The * represents statistical significance with $p < 0.01$ when compared with the control group (Fc).

Figure 4A:
Figure 4A:
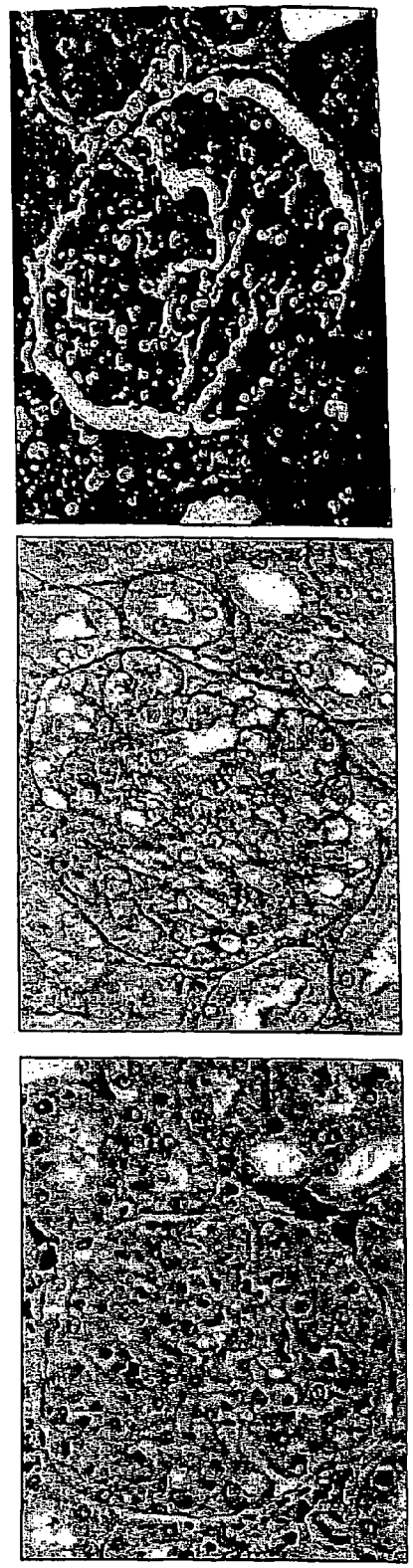

Pregnant rats treated with sFlt-1 had significant hypertension and nephrotic range albuminuria compared with Fc controls. Nonpregnant rats administered sFlt1 also developed hypertension and proteinuria. Notably, the sFlk-Fc treated nonpregnant rats developed hypertension and proteinuria, whereas the sFlk-Fc treated pregnant rats did not. In pregnancy, therefore, the antagonism of VEGF alone is insufficient to produce pre-eclampsia, possibly due to the presence of high levels of PlGF. In the nonpregnant state, where PlGF is virtually absent, antagonism of VEGF alone is sufficient to disrupt the pro/anti-angiogenic balance and produce renal pathologies similar to those associated with pre-eclampsia. Various staining techniques were used to examine the renal lesion that was observed in all sFlt-1 treated rats (FIG. 4). Harvested kidneys from the rats were fixed in Bouin's solution, sectioned and stained with H&E and PAS stains. For electron microscopy, renal tissue was fixed in glutaraldehyde, embedded in araldite-epon mixture, and ultrathin kidney sections (1 μm) were cut, stained with Toluene blue and assessed using a Zeiss EM 10 at various magnifications. Immunofluorescence for fibrin deposits within the glomeruli was done using polyclonal anti-fibrin antibody (ICN, Switzerland). Global and diffuse glomerular endotheliosis was the renal lesion universally observed in the sFlt-1 treated rats. We detected glomerular enlargement with occlusion of the capillary loops by swelling and hypertrophy of endocapillary cells. Numerous apparent protein resorption droplets were seen in the glomerular epithelial cells. No segmental glomerulosclerosis was observed. Isolated "double contours" and focal deposition of fibrin within the glomeruli were seen. This finding of fibrin deposition in the absence of significant mesangial interposition is similar to what has been described as typical of the pre-partum stage of the human disease (Kincaid-Smith, *Am. J. Kidney Dis.*, 17:144-148, 1991).

Immunofluorescence for fibrin showed foci of fibrin deposition within the glomeruli of sFlt-1 treated animals but not Fc treated animals. The sFlk1 treated nonpregnant rats developed the same lesion. In fact, when sFlk 1 was used at the same levels as sFlt-1, the renal damage was more severe in the non-pregnant rats, as there are fewer circulating pro-angiogenic molecules for the sFlt-1 to antagonize. These results suggested that elevated levels of sFlt-1 may be responsible for the glomerular endotheliosis associated with pre-eclampsia, but that this effect was independent of the placenta since glomerular changes were detected in nonpregnant as well as pregnant rats. These results also suggested that antagonism of both VEGF and PlGF is important in the pathology of pre-eclampsia as hypertension and proteinuria occurred in sFlk-1 treated non-pregnant mice but not in sFlk-1 treated pregnant mice where PlGF levels are high.

The animal model created herein can be used as an experimental model to test novel therapeutic compounds. Both the efficacy of potential therapeutic compounds and the pharmacology and toxicity can be studied using this animal model.

EXAMPLE 5

Effects of sFlt-1 in an Animal Model of Eclampsia

Pregnant rats in their early second trimester of pregnancy are injected with exogenous sFlt-1. The rats are then monitored and tested during their early third trimester for the development of eclampsia. Tests used for detection of eclampsia can include MRI of the rat brains for the development of edema, EEG of the rat brain for the development of seizures, and histology of the rat brains to determine if endothelial damage has occurred along the blood-brain barrier and choroids-plexus using specific endothelial markers.

The animal model created herein can be used as an experimental model to test novel therapeutic compounds. Both the efficacy of potential therapeutic compounds and the pharmacology and toxicity can be studied using this animal model.

EXAMPLE 6

PlGF/Creatinine Ratio in Urine is Diagnostic of Pre-Eclampsia

Urine samples were obtained from 10 women at 16 weeks gestation (five normals, four mild preeclamptics, and one severe pre-eclamptic). These samples were provided by Dr. Ravi Thadhani at Massachusetts General Hospital. The average urinary free PlGF/creatinine ratios (pg PlGF per mg of creatinine) for the normal pregnant women were 78+/−10.7 and for the four mild pre-eclamptics were 33+/−5.0 and for the one severe preeclamptic patient was 17. Thus, an alteration in the ratio of PlGF to creatinine in urine is useful as a diagnostic indicator for pre-eclampsia in a patient.

EXAMPLE 7

Urinary PlGF Levels Measure in Control and Pre-Eclamptic Pregnant Women

Urinary PlGF was measured in control pregnant women and pre-eclamptic women using archived urine specimens from the CPEP trial (see Example 8) in collaboration with Dr. Richard Levine at the NIH (Table 2). The table below shows significant decreases in urinary PlGF in patients who later developed pre-eclampsia during mid-pregnancy (22-30 weeks) and late pregnancy (>30 weeks), but not in early pregnancy (<20 weeks). All urine specimens were obtained prior to clinical symptoms of pre-eclampsia.

TABLE 2

Urinary PlGF levels in pg/ml in pre-eclamptic versus control pregnant patients.

|  | Control (n = 118) | PE (n = 120) |
| --- | --- | --- |
| Early pregnancy | 39.80 | 42.28 |
| Mid pregnancy | 193.11 | 98.66 (p < 0.0001) |
| Late pregnancy | 107.82 | 62.05 (p = 0.0213) |

EXAMPLE 8 sFlt-1 and PlGF Protein Levels as a Diagnostic Indicator of Pre-Eclampsia and Eclampsia in Women For this study we used archived samples from the Calcium for Pre-eclampsia Prevention trial in order to analyze the gestational patterns of circulating sFlt-1, free PlGF, and free VEGF in normotensive and pre-eclamptic pregnancies in collaboration with Dr. Richard Levine at the NIH. Calcium for Pre-eclampsia Prevention, or CPEP, was a randomized, double-blind clinical trial conducted during 1992-1995 to evaluate the effects of daily supplementation with 2 grams elemental calcium or placebo on the incidence and severity of pre-eclampsia (Levine et al., *N. Engl. J. Med.* 337:69-76, 1997; Levine et al., *Control Clin. Trials* 17:442-469, 1996). Healthy nulliparous women with singleton pregnancies were enrolled between 13 and 21 weeks gestation at five participating U.S. medical centers and followed until 24 hours postpartum using a common protocol and identical data collection forms. At enrollment, all CPEP participants had blood pressure <135/85 mm Hg, and none had renal dysfunction or proteinuria. Gestational age was determined by ultrasound examination. Serum specimens were obtained from participants prior to enrollment in the trial (13-21 weeks), at 26-29 weeks, at 36 weeks if still pregnant, and when hypertension or proteinuria were noted. "Endpoint specimens" (active PE) were specimens obtained at or after onset of pre-eclampsia symptoms and signs, but before labor and delivery as described elsewhere (Levine et al., 1996, supra). Archived blood samples from the CPEP trial were obtained through collaboration with Dr. Richard Levine at the NIH.

Participants

We selected subjects having complete outcome information, serum samples obtained at <22 weeks, and a liveborn male infant. Of 4,589 CPEP participants, we excluded 253 lost to follow-up, 21 whose pregnancy had terminated prior to 20 weeks, 13 missing maternal or perinatal outcome data, 4 without smoking history, 9 with hypertension not verified by chart review teams, and 32 others with stillbirths, leaving 4,257 women with adequate information and live births. Among these 2,156 had male infants. After excluding one woman whose infant had a chromosomal abnormality, 381 with gestational hypertension, and 43 without a baseline serum specimen, 1,731 women remained. Of these, 175 developed pre-eclampsia and 1,556 remained normotensive throughout pregnancy.

Since calcium supplementation had no effect on the risk and severity of pre-eclampsia and was unrelated to concentrations of pro- and anti-angiogenic molecules, cases and controls were chosen without regard to CPEP treatment. For each pre-eclampsia case one normotensive control was selected, matched for enrollment site, gestational age at collection of the first serum specimen (within one week), and freezer storage time at −70° C. (within 12 months). 120 matched pairs ("cases" and "controls") were randomly chosen for analysis of all 657 serum specimens obtained before labor (Table 3, below). Mean gestational age at collection of the first serum specimen was 112.8 and 113.6 days in cases and controls, respectively; mean duration of freezer storage was 9.35 and 9.39 years.

TABLE 3

Characteristics of cases and controls at CPEP enrollment and of their newborn infants

| Characteristic | Cases (n = 120) | Controls (n = 118) |
|---|---|---|
| Age (yr) | 20.8 ± 4.5 | 20.0 ± 3.4 |
| Body mass index | 27.3 ± 6.8 | 25.0 ± 6.1** |
| Systolic blood pressure (mm Hg) | 109.0 ± 9.0 | 106.0 ± 9.0† |
| Diastolic blood pressure (mm Hg) | 62.0 ± 8.0 | 59.0 ± 7.0‡ |
| Gestational age at delivery (wks) | 38.1 ± 2.6 | 38.9 ± 2.5* |
| Current smoker [n (%)] | 9 (7.5) | 13 (11.0) |
| Ever married [n (%)] | 25 (20.8) | 22 (18.6) |
| Race/ethnicity* | | |
| White, non-Hispanic [n (%)] | 24 (20.0) | 33 (28.0) |
| White, Hispanic [n (%)] | 21 (17.5) | 14 (11.9) |
| African-American [n (%)] | 69 (57.5) | 68 (57.6) |
| Other, unknown [n (%)] | 6 (5.0) | 3 (2.5) |
| Birthweight (g) | 3100 ± 796 | 3247 596 |
| Delivery <37 wks [n (%)] | 26 (21.7) | 9 (7.6)§ |
| Small for gestational age (<10th percentile) [n (%)] | 18 (15.0) | 4 (3.4)§ |

Mean ± standard deviation unless indicated
P = 0.03
**P = 0.007
†P = 0.001
‡P = 0.006
§P = 0.002
*race or ethnic group was self-reported.

For this study, hypertension was defined as a diastolic blood pressure of at least 90 mm Hg on two occasions 4-168 hours apart. Severe hypertension was defined as a diastolic blood pressure of at least 110 mm Hg on two occasions 4-168 hours apart, or one occasion if the woman had received antihypertensive therapy. Proteinuria was defined as 300 mg or more protein in a 24-hour urine collection, two random urine specimens 4-168 hours apart containing at least 1+ protein by dipstick, a single urine sample with a protein/creatinine ratio at least 0.35, or a single random urine specimen containing at least 2+ protein by dipstick. Severe proteinuria was diagnosed by a 24-hour urine collection sample containing at least 3.5 g protein or by two random urine specimens with at least 3+ protein by dipstick. Pre-eclampsia was defined as hypertension and proteinuria occurring within 7 days of each other; severe pre-eclampsia was defined as pre-eclampsia with severe hypertension, severe proteinuria, HELLP syndrome (hemolysis, elevated liver enzymes, low platelets), or eclampsia. The onset of pre-eclampsia was the time of detection of the first elevated blood pressure or proteinuria in the urine sample leading to the diagnosis of pre-eclampsia.

Small for gestational age (SGA) was defined as birth weight lower than the $10^{th}$ percentile for gestational age according to US tables of birth weight for gestational age by race, parity, and infant sex (Zhang and Bowes 1995, supra).

Procedures

Assays were performed at the Beth Israel Deaconess Medical Center by laboratory personnel who were blinded to patients' diagnoses and other relevant clinical information. Specimens were randomly ordered for analysis. Enzyme-linked immunosorbent assays (ELISA) for human sFlt-1, free PlGF, and free VEGF were performed according to the manufacturer's instructions, using kits purchased from R&D Systems (Minneapolis, Minn.). Aliquots of serum samples which had been stored at −70° C., were thawed to room temperature, diluted with BSA/Tris-buffered saline, and incubated for 2 hours in a 96-well plate pre-coated with a capture antibody directed against sFlt-1, PlGF, or VEGF. The wells were then washed three times, incubated 20 minutes with a substrate solution containing hydrogen peroxide and tetramethylbenzidine, and the reaction quenched with 2N sulfuric acid. Optical density was determined at 450 nm (wavelength correction 550 nm). All assays were performed in duplicate. Protein concentrations were calculated using a standard curve derived from known concentrations of the respective recombinant proteins. If the difference between duplicates exceeded 25%, the assay was repeated and initial results discarded. The assays had sensitivities of 5, 7, and 5 pg/ml for sFlt 1, PlGF, and VEGF, respectively, with inter- and intra-assay coefficients of variation of 7.6% and 3.3% for sFlt 1, 11.2% and 5.4% for PlGF, and 7.3% and 5.4% for VEGF.

Statistical Analysis

Chi-square and t tests were used in analyses of maternal or infant characteristics to compare categorical or continuous variables, respectively. Although arithmetic mean values of concentrations are given in text and figures, statistical testing was performed after logarithmic transformation unless noted otherwise. Adjustment was performed using logistic regression on logarithmically transformed concentrations.

Results

Of the 120 cases, 80 developed mild and 40 severe pre-eclampsia, including 3 with HELLP syndrome and 3 with eclampsia. Case patients were shorter than control patients, had a higher body mass index, and higher baseline blood pressure (Table 2). In addition, larger proportions of case patients had pregnancies complicated by pre-term delivery or small-for-gestational age (SGA) infants. Case patients contributed an average of 2.9 serum specimens to the study; controls, 2.6 specimens.

We first confirmed that sFlt-1, PlGF, and VEGF were altered in patients with pre-eclampsia at the time of active disease as compared to gestationally matched controls from this CPEP study group. Specimens drawn at the time of established clinical pre-eclampsia (endpoint specimens) had dramatically increased sFlt-1 levels, decreased PlGF levels, and decreased VEGF levels compared to controls with gestational ages (4382 vs. 1643 pg/ml sFlt1, p<0.0001; 137 vs. 669 pg/ml PlGF, p<0.0001; and 6.41 vs. 13.86 pg/ml VEGF, p=0.06) for cases and controls, respectively, in 23 gestational-age matched pairs) similar to prior published reports (Maynard et al., *J. Clin. Invest.* 111:649-658, 2003).

Figure 5A:
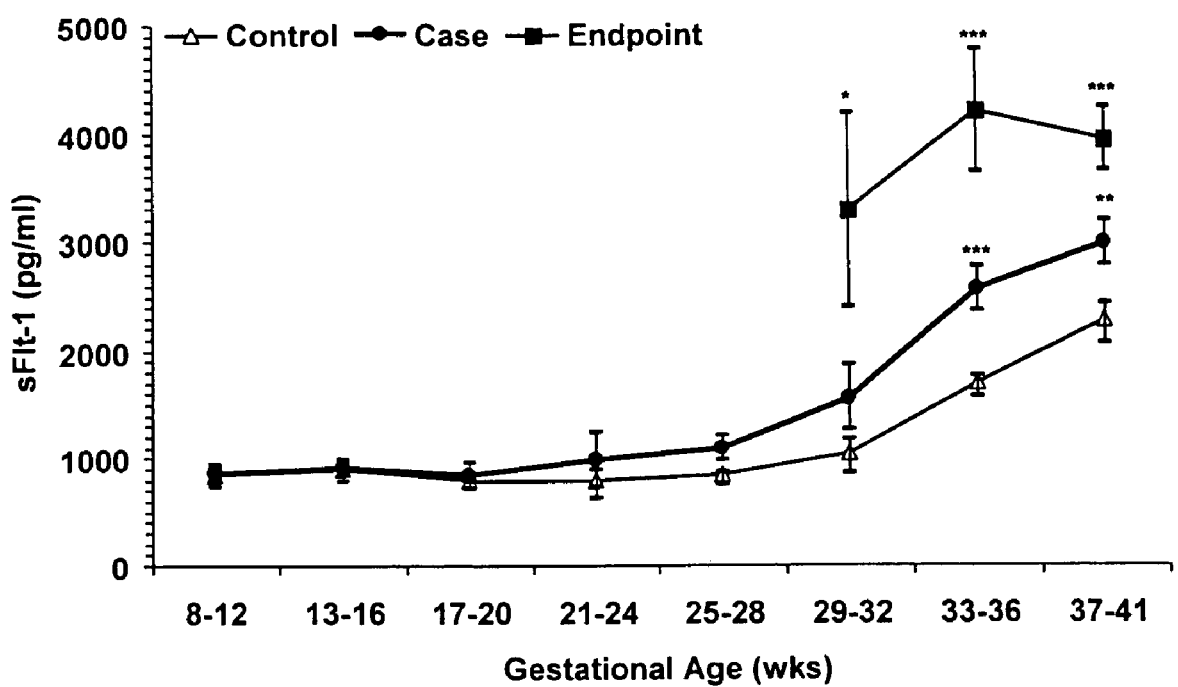
FIGS. 5A-5C are graphs showing sFlt-1 levels measured before and after the onset of pre-eclampsia by gestational age.
Figure 5B:
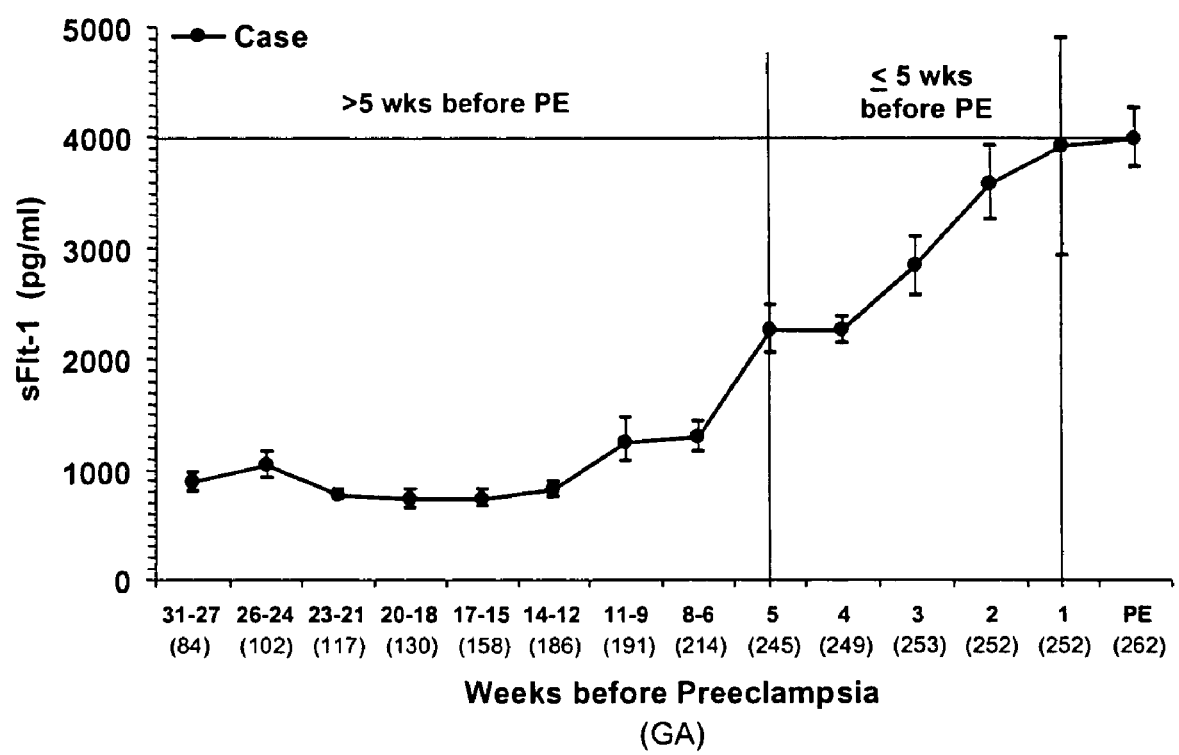
Figure 5C:
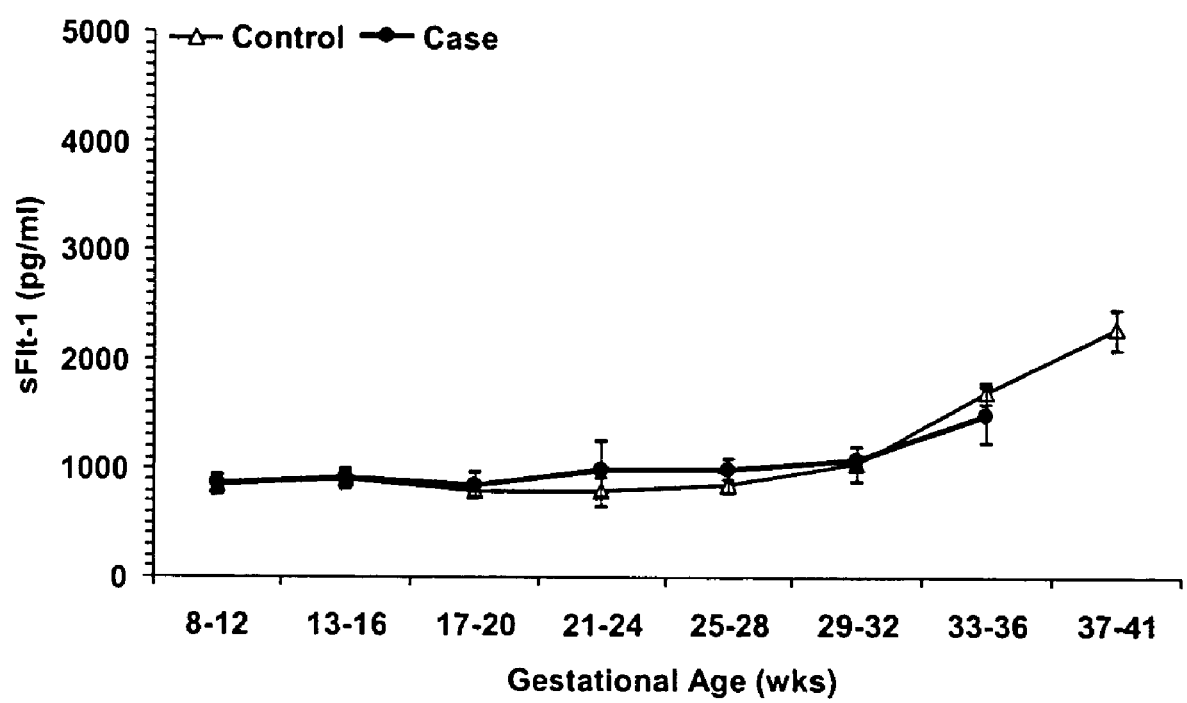

In order to evaluate the gestational pattern of sFlt-1, PlGF and VEGF levels, we measured circulating concentrations of sFlt-1, PlGF, and VEGF from serum specimens obtained from case patients and control patients within various gestational age windows. The gestational pattern of sFlt-1 protein for 120 pre-eclamptic and 120 control women is shown in FIG. 5A. sFlt-1 levels in control patients remained constant until 33-36 weeks, when they rose by approximately 145 pg/ml per week until labor and delivery. Among case patients before clinical symptoms, sFlt-1 appeared to begin to rise at 21-24 weeks, with a steeper rise and a statistically significant difference from controls at 29-32 weeks (FIG. 5A). Overall, differences between case and control patients measured before the onset of clinical symptoms were 17% (p<0.05) at mid-gestation. The end-point specimens were significantly elevated as compared to specimens drawn prior to the disease. In order to evaluate the mechanisms of sFlt-1 rise prior to the onset of clinical disease, we plotted sFlt-1 concentrations on all pre-eclamptics by weeks prior to the onset of pre-eclampsia (FIG. 5B). Mean sFlt-1 concentrations in specimens from case patients were plotted by completed weeks before onset of pre-eclampsia. Beginning at 5 weeks prior to pre-eclampsia, sFlt-1 concentrations rose substantially until 1 week prior to the onset of disease when they approached the concentrations observed in endpoint specimens. The increases in sFlt-1 at 4, 3, 2, and 1 week(s) before pre-eclampsia occurred with little change in mean gestational age and cannot be explained by late third trimester increases with advancing gestational age. From 8-6 to 5 weeks before pre-eclampsia sFlt-1 increased 962 pg/ml, while mean gestational age rose 31 days. About one-third of this increase in sFlt-1 cannot be attributed to advancing gestation. When sFlt-1 was graphed by gestational age in controls and in cases after removing specimens obtained ≦5 weeks before onset of pre-eclampsia, no substantial differences were observed (FIG. 5C). These data suggest that the higher sFlt-1 concentration in case patients prior to onset of pre-eclampsia is due to acute rises in sFlt-1 within the 5 weeks before onset of clinical disease.

Figure 6A:
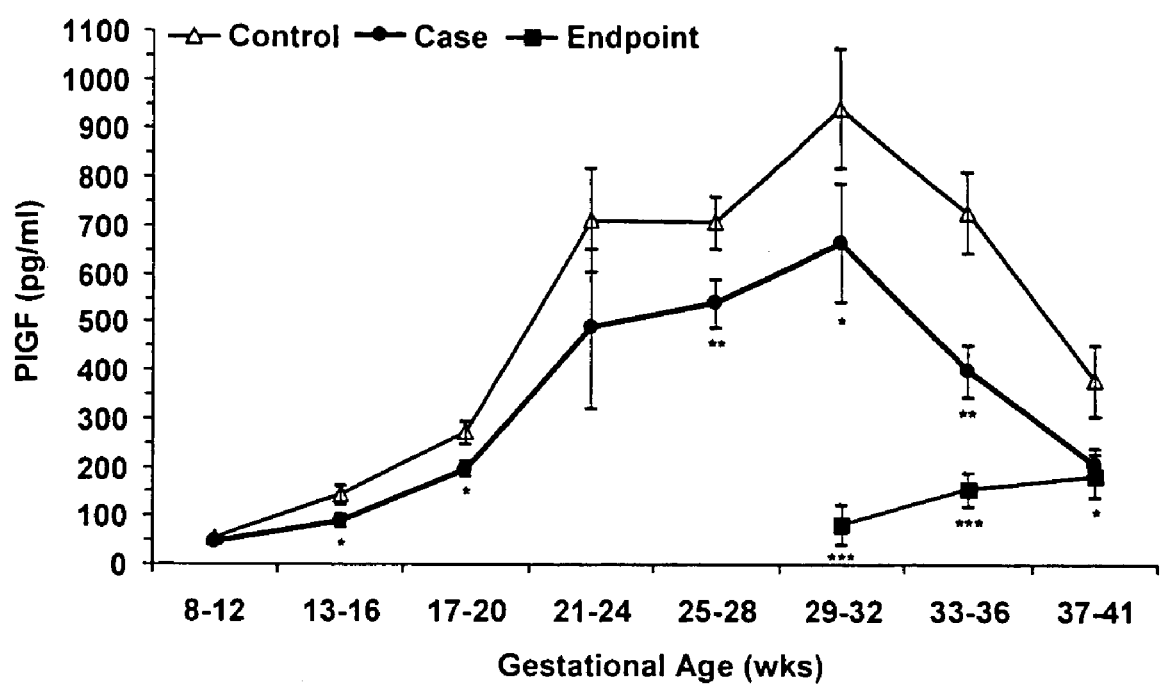
FIGS. 6A-6C are graphs showing the levels of PlGF before and after pre-eclampsia by gestational age.
Figure 6B:
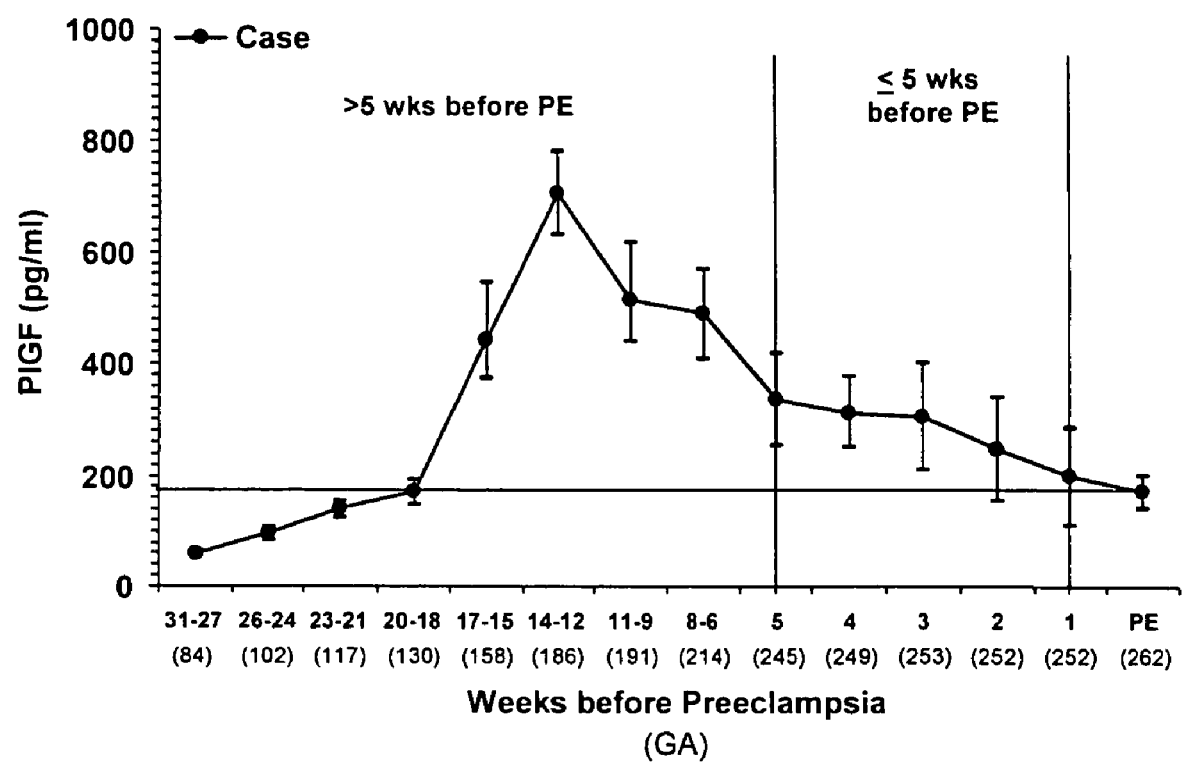
Figure 6C:
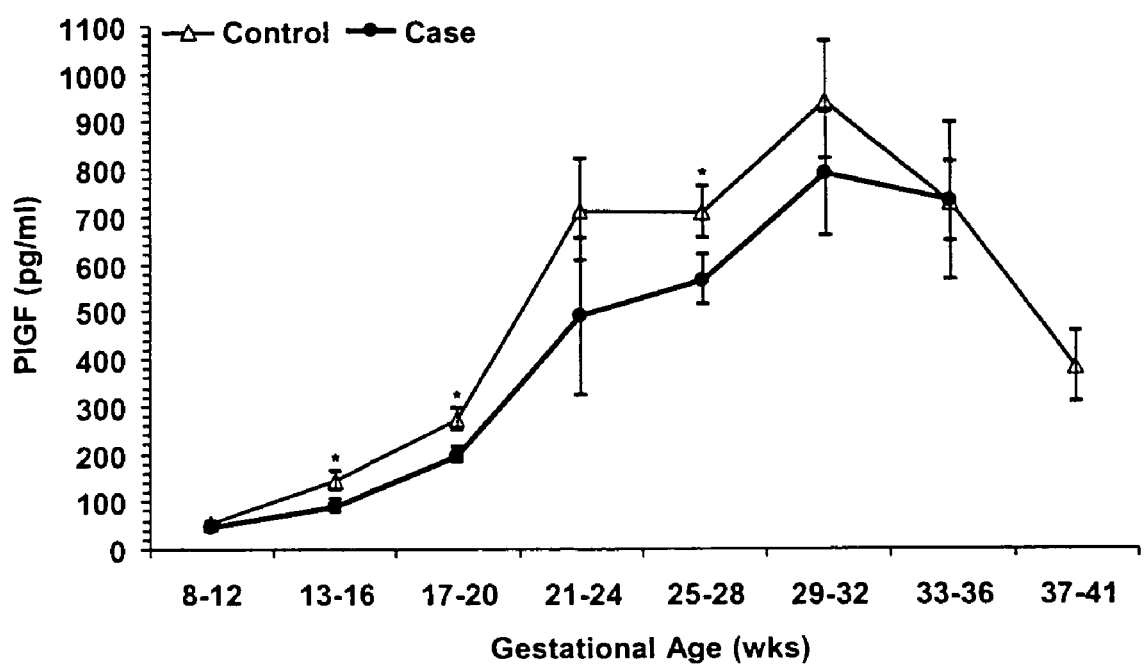

We then plotted the gestational pattern of PlGF protein in the same patient group as shown in FIG. 6A. Control PlGF protein concentrations rose during the first two trimesters, peaked at 29-32 weeks, and fell during late gestation. Among case patients, prior to pre-eclampsia, PlGF protein concentrations followed a similar gestational pattern, but were significantly lower than controls from 13-16 weeks. Overall, differences in PlGF between cases patients and controls measured before the onset of clinical symptoms were 35% ($p<0.0001$) at mid-gestation. PlGF levels in cases prior to onset of pre-eclampsia is depicted by weeks before pre-eclampsia (FIG. 6B), and by gestational age after removing specimens <5 weeks before pre-eclampsia (FIG. 6C). By 1 week prior to onset of pre-eclampsia, concentrations approached those observed after onset of pre-eclampsia (FIG. 6B). Compared to controls, PlGF levels from case patients were moderately reduced remote from delivery, with more substantial reductions at 5 and 3 weeks before delivery. Concentrations from control patients remained high from 17-15 through 3 weeks before delivery, then fell dramatically. The graph showing PlGF levels excluding specimens obtained ≦5 weeks before pre-eclampsia indicates a smaller decrease in cases relative to controls at 29-32 weeks of gestation and none at all in specimens obtained from case patients at 33-36 weeks (FIG. 6C). This suggests that the fall in PlGF concentrations in the weeks prior to the disease was responsible for the dramatically low levels of PlGF noted at the onset of disease (or end point specimens shown in FIG. 6A).

VEGF concentrations throughout pregnancy were very low and similar in controls and cases before pre-eclampsia, except for a significant decrease in case patients at 37-41 weeks. Mean VEGF concentrations at 23-32 weeks in cases excluding specimens obtained 5 weeks before pre-eclampsia did not differ significantly from controls (11.6 vs. 12.8 pg/ml), whereas concentrations in cases including specimens ≦5 weeks before delivery did (5.1 vs. 12.8 pg/ml, $p<0.01$). At 33-41 weeks case VEGF concentrations >5 or ≦5 weeks before pre-eclampsia were higher and lower than controls, respectively (11.2 pg/ml and 8.3 vs. 9.7 pg/ml), although these differences were not significant.

Figure 7:
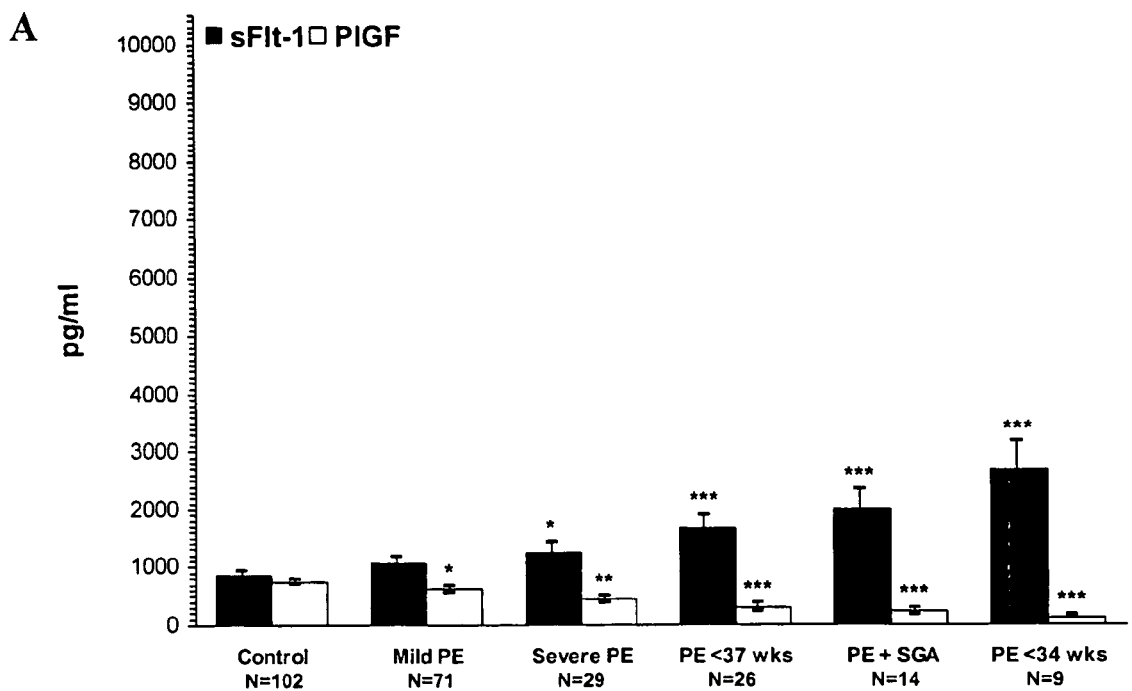
FIGS. 7A and 7B are graphs showing sFlt-1 and PlGF levels by pre-eclampsia status and severity.
Figure 7:
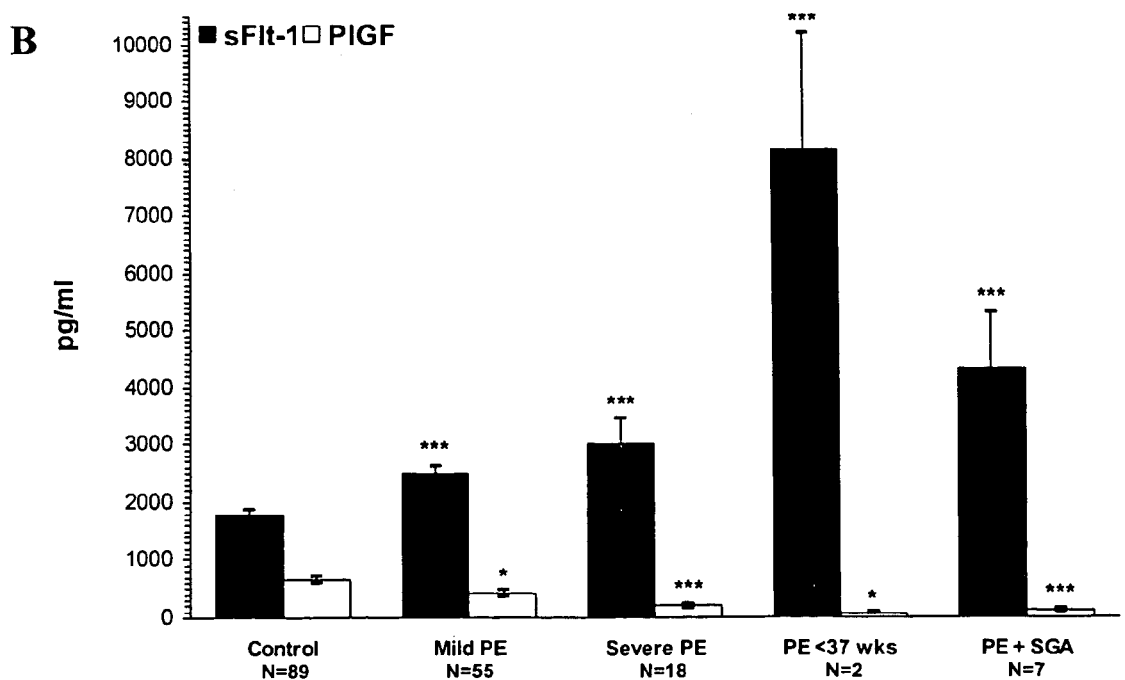

FIG. 7 depicts sFlt-1 and PlGF at 23-32 weeks (FIG. 7A) and 33-41 weeks (FIG. 7B) by pre-eclampsia status and severity. The graphs show that sFlt-1 increases and PlGF decreases before onset of pre-eclampsia were associated with disease severity, time of onset, and the presence of an SGA infant. At 23-32 weeks, sFlt-1 and PlGF in case patients with an SGA infant before onset of pre-eclampsia were significantly higher or lower, respectively, than corresponding concentrations in control patients with an SGA infant. Moreover, in comparison to control patients who delivered pre-term, case patients with pre-term delivery had higher sFlt-1 and significantly lower PlGF.

To determine whether concentrations of sFlt-1 or PlGF prior to clinical signs of pre-eclampsia were associated with the risk of this condition, we calculated odds ratios for pre-eclampsia for each quartile of control values of sFlt-1 and PlGF, as compared to the lowest or highest quartile, respectively (Table 4). We also examined the pre-eclampsia risk of the extreme quartiles with respect to all other quartiles, as follows. For specimens obtained in the second- and early third-trimester, the lowest quartile of PlGF was associated with an increased risk of preterm (<37 weeks gestation) pre-eclampsia (OR 7.4, 95% CI 1.8 to 30.2 for 13-20 week specimens; OR 7.9, 95% CI 2.9 to 21.5 for 21-32 week specimens). A level of PlGF in the lowest quartile, however, was not a significant predictor of term (≧37 weeks) pre-eclampsia. For sFlt-1, associations with pre-eclampsia were observed only closer to disease onset. An sFlt-1 level in the highest quartile between 21 to 32 weeks gestation (but not earlier) predicted preterm pre-eclampsia (OR 5.1, 95 percent CI 2.0 to 13.0), and a level in the highest quartile between 33 and 41 weeks (but not earlier) predicted term pre-eclampsia (OR 6.0, 95 percent CI 2.9 to 12.5). This is consistent with FIG. 5B, which shows that elevation of sFlt-1 occurs largely within 5 weeks of onset of clinical disease. The lowest quartile of VEGF was not predictive of pre-eclampsia.

TABLE 4

Odds Ratios (OR) for Pre-eclampsia at <37 and ≧37 Weeks Prior to Clinical Signs by Quartiles of Total sFlt-1 and Free PlGF in Controls at 13-20, 21-32, and 33-41 Weeks Gestation

| sFlt-1 (pg/ml) | Controls N | PE < 37 wks N OR* | | PE ≧ 37 wks N OR* | | PlGF (pg/ml) | Controls N | PE < 37 wks N OR* | | PE ≧ 37 wks N OR* | |
|---|---|---|---|---|---|---|---|---|---|---|---|
| | | | | | | 13-20 wks | | | | | |
| Q4: >1047 | 25 | 6 | 1.3 (0.4-5.0) | 20 | 1.5 (0.6-3.7) | Q4: >307 | 25 | 4 | 1.0 Referent | 4 | 1.0 Referent |
| Q3: >698-1047 | 25 | 8 | 2.2 (0.6-7.8) | 23 | 1.9 (0.8-4.5) | Q3: >160-307 | 25 | 2 | 0.6 (0.1-3.5) | 22 | 5.6 (1.7-19.0) |

TABLE 4-continued

Odds Ratios (OR) for Pre-eclampsia at <37 and ≧37 Weeks Prior to Clinical Signs by Quartiles of Total sFlt-1 and Free PlGF in Controls at 13-20, 21-32, and 33-41 Weeks Gestation

| | | | | | | | | | | |
|---|---|---|---|---|---|---|---|---|---|---|
| Q2: >531-698 | 25 | 4 | 0.5 (0.1-2.3) | 16 | 1.1 (0.4-2.7) | Q2: >87-160 | 25 | 6 | 1.9 (0.4-8.2) | 26 | 6.4 (1.9-22.1) |
| Q1: ≦531 | 25 | 6 | 1.0 Referent | 16 | 1.0 Referent | Q1: ≦87 | 25 | 12 | 9.6 (1.6-57.6) | 23 | 6.7 (1.6-27.5) |

21-32 wks

| | | | | | | | | | | |
|---|---|---|---|---|---|---|---|---|---|---|
| Q4: >1131 | 25 | 16 | 4.7 (1.3-16.6) | 18 | 1.7 (0.7-4.4) | Q4: >1021 | 25 | 1 | 1.0 Referent | 14 | 1.0 Referent |
| Q3: >743-1131 | 26 | 5 | 1.4 (0.3-6.0) | 21 | 1.7 (0.7-4.2) | Q3: >677-1021 | 26 | 1 | 1.1 (0.1-18.2) | 19 | 1.2 (0.5-3.1) |
| Q2: >512-743 | 25 | 1 | 0.3 (0.0-2.8) | 21 | 1.9 (0.8-4.7) | Q2: >363-677 | 25 | 5 | 5.3 (0.6-49.3) | 20 | 1.3 (0.5-3.2) |
| Q1: ≦512 | 26 | 4 | 1.0 Referent | 14 | 1.0 Referent | Q1: ≦363 | 26 | 19 | 19.6 (2.3-163.8) | 21 | 1.2 (0.5-3.1) |

| sFlt-1 (pg/ml) | Controls N | PE < 37 wks | PE ≧ 37 wks | PlGF (pg/ml) | Controls N | PE < 37 wks | PE ≧ 37 wks |
|---|---|---|---|---|---|---|---|

33-41 wks

| | | | | | | | |
|---|---|---|---|---|---|---|---|
| Q4: >2191 | 22 | 44 | 7.5 (2.6-21.8) | Q4: >948 | 22 | 6 | 1.0 Referent |
| Q3: >1633-2191 | 22 | 12 | 1.7 (0.5-5.5) | Q3: >377-948 | 22 | 18 | 2.7 (0.9-8.3) |
| Q2: >1287-1633 | 22 | 7 | 1.0 (0.3-3.3) | Q2: >175-377 | 22 | 19 | 2.8 (0.9-8.5) |
| Q1: ≦1287 | 23 | 8 | 1.0 Referent | Q1: ≦175 | 23 | 28 | 4.1 (1.4-12.2) |

*Odds ratio adjusted for gestational age and body mass index (with 95% CI). OR with 95% CI > 1.0 in bold type. Case specimens were obtained prior to clinical signs of pre-eclampsia.

These results demonstrate that sFlt-1 levels begin to rise dramatically about 5 weeks before the onset of pre-eclampsia symptoms. Parallel with the rise in sFlt-1, free PlGF and free VEGF levels fall, suggesting that the decrease in PlGF and VEGF may be due at least partially to antagonism by sFlt-1 and not due to a decrease in placental production of PlGF and VEGF. Three pre-eclampsia subgroups—severe pre-eclampsia, early onset of disease, and SGA infants—had higher sFlt-1 and lower PlGF concentrations at 23-32 weeks and at 33-41 weeks than controls or women with mild pre-eclampsia. We have also demonstrated a small but significant decrease in free PlGF beginning early in the second trimester among women destined to develop pre-eclampsia. These results demonstrate that a decrease in PlGF levels may be a useful predictor of early onset pre-eclampsia.

We describe here for the first time the gestational pattern of sFlt-1 in normal pregnancy, observing relatively stable levels throughout gestation followed by a steady increase beginning at 33-36 weeks. This rise corresponds to the late gestational fall in PlGF observed in normal pregnancy by others (Torry et al., *J. Soc. Gynecol. Invest.* 10:178-188, 1998; Taylor et al., *Am. J. Obstet. Gynecol.* 188:177-182, 2003) and in the results described herein. The temporal association, together with the knowledge that sFlt-1 interferes with PlGF ELISA measurement (Maynard et al., supra) suggests that the fall in free PlGF levels during late gestation may be due to the rise in sFlt-1 levels. During first and second trimesters, when placental growth is needed to keep pace with increasing fetal demands, PlGF concentrations are high and sFlt-1 concentrations are low, creating a relatively pro-angiogenic state. Later in gestation, when placental vascular growth may need to be tempered and halted, there is a rise in the anti-angiogenic sFlt-1 and resulting decrease in PlGF. In women with pre-eclampsia, the sFlt-1 rise begins earlier in gestation, approximately five weeks before symptom onset, at about 29-32 weeks gestation on average. Thus, in pre-eclampsia, the anti-angiogenic "brakes" may be applied too soon and too strongly, resulting in an exaggeration of a normal physiologic process which arrests placental growth. It seems clear that the pathologic placental changes that characterize pre-eclampsia occur early in gestation (10-14 weeks), well before the dramatic rise in sFlt-1. The resulting placental ischemia itself may enhance sFlt-1 production, ultimately triggering a burst in sFlt-1.

In addition to the large differences seen in the five weeks prior to the development of clinical symptoms, women destined to develop pre-eclampsia had small, but statistically significant, decreases in free PlGF as early as 13-16 weeks gestation. This fall in PlGF generally was not accompanied by a reciprocal increase in sFlt-1 levels. However, there was a tendency towards slightly higher sFlt-1 levels in cases during the first trimester though it was not statistically significant (For example at the 17-20 week window, average sFlt-1 levels in cases were 865.77 pg/ml vs. 795.25 in controls). This decrease in PlGF levels early on in gestation might reflect a smaller placental production of PlGF in pregnancies compromised by conditions such as pre-eclampsia or SGA. Importantly, in patients with pre-eclampsia complicated by SGA, we found a statistically significant increase in both sFlt-1 elevation and PlGF fall prior to the disease presentation. It is also possible that there is no change in placental production of PlGF in pre-eclamptics and that elevation of local sFlt-1 levels in the placenta may contribute to the decrease in circulating free PlGF. This is supported by the finding that placental PlGF, measured by immunohistochemistry, is not altered in pre-eclampsia (Zhou et al., *Am. J. Pathol.* 160:1405-1423, 2002).

In summary, we have shown that sFlt-1 starts rising in pre-eclampsia at least 5 weeks before the onset of clinical disease which is accompanied by decreases in circulating free PlGF and free VEGF. Decreased PlGF during the first trimester may serve as a predictor of pre-eclampsia and elevated sFlt-1 may serve as a predictor of proximity to clinical disease. This data in conjunction with the animal work described above demonstrating sFlt-1 alone induces pre-eclampsia like symptoms in rodents suggests a probable etiological role for sFlt-1 in the pathogenesis of pre-eclampsia. Our limited data on SGA infants and preterm delivery in controls, as compared to case patients, suggest that the increased alterations in protein levels observed in pre-eclamptic pregnancies with an SGA infant are more substantial than a difference due only to intrauterine growth restriction or pre-term delivery in the absence of pre-eclampsia.

Figure 8:
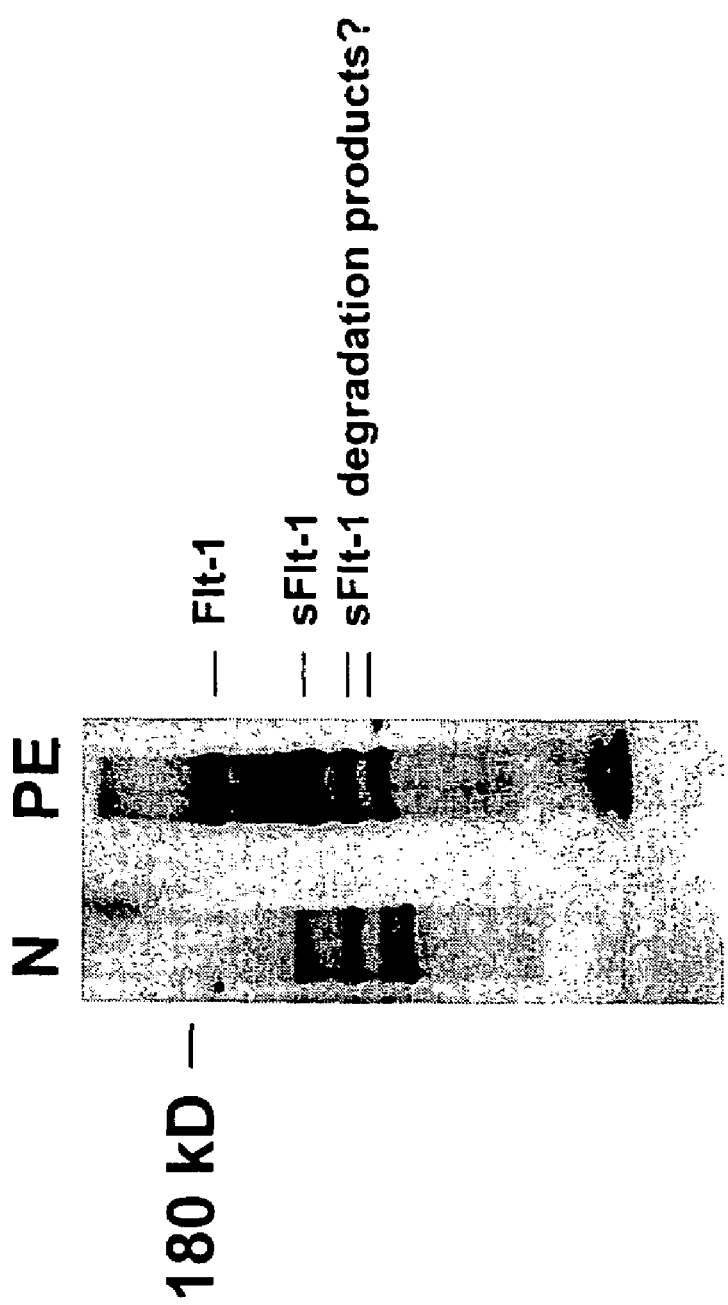
FIG. 8 is an autoradiogram showing the expression of flt, sFlt-1, and related variants or fragments in PBMCs isolated from normal and preeclamptic patients. Protein lysates were analyzed by western blots using an antibody that recognizes the N-terminus of Flt-1 protein.

EXAMPLE 9 sFlt-1 Protein and Protein Fragments Detected in Monocytes from Normal and Preeclamptic Patients Peripheral blood mononuclear cells, rich in monocytes, were isolated from normal and pre-eclamptic patients and used to measure the leves of sFlt-1 and sFlt-1 fragments. Protein extracts were prepared from the PBMCs and Flt-1/sFlt-1 levels were analyzed by Western blots using an antibody that recognizes the N-terminus of Flt-1 protein (a region common to both proteins). The results of this experiment showed increased Flt-1 and sFlt-1 levels in the monocytes from pre-eclamptic patients (FIG. 8). In addition several bands were detected that had a faster migration than full-length sFlt-1. These faster migrating bands may be degradation products, alternatively spliced isoforms, enzymatic cleavage products, or other forms of sFlt-1.

EXAMPLE 10 sFlt-1 Protein Levels as a Diagnostic Indicator of Cardiovascular Conditions in Women with a History of Pre-Eclampsia Women with a history of pre-eclampsia have been shown to have a propensity to develop cardiovascular conditions (see for example Kestenbaum et al., *Am. J. Kidney Dis.* 42:982-989, 2003). Given our discovery of the use of s-Flt-1 as a diagnostic indicator of pre-eclampsia or eclampsia or a predisposition to pre-eclampsia or eclampsia, a study was performed to determine if sFlt-1 could also be used as a diagnostic indicator of a propensity to develop cardiovascular conditions or events in women who have a history of pre-eclampsia. The results of this study are shown in Table 5.

We examined 29 normotensive women with a history of pre-eclampsia and 32 normotensive women with previous normal pregnancies at 18.0±9.7 months postpartum in the General Clinical Research Centers at the Massachusetts Institute of Technology in collaboration with Dr. Ravi Thadhani at the Massachussetts General Hospital. Since pre-eclampsia often presents near term and other disorders can lead to pre-term delivery, to prevent misclassification of pregnancy outcome, all normotensive women had delivered at term (>38 weeks). Women with current pregnancy, diabetes or a history of gestational diabetes, chronic hypertension, proteinuria or serum creatinine >1.0 mg/dL were excluded. After providing written informed consent, subjects underwent a history and physical examination and a urine pregnancy test. Blood was collected on the morning after an overnight fast for measurement of free VEGF and sFlt-1. Samples were processed immediately, stored at −80° C. for no longer than 18 months and were thawed only for the current study. Commercial assay ELISA kits were used for sFlt-1 and free VEGF (R&D systems, Minnesota USA). The intra- and inter-assay co-efficent of variance (CVs) for sFlt-1 and VEGF were 3.5 and 5.6, and 8.1 and 10.9, respectively. All samples were run in duplicate by technicians blinded to pregnancy outcome.

Univariate comparisons between the pregnancy outcome groups were performed using two-sample t tests, Wilcoxon rank sum test or Fisher exact test as appropriate. Logistic regression was used to calculate odds ratios for having had prior pre-eclampsia given levels of postpartum markers, and to adjust for potential confounding.

TABLE 5

Postpartum sFlt-1 data according to pregnancy outcome.

| | Pre-eclampsia N = 29 | Normotensive N = 32 | P |
|---|---|---|---|
| Age (years) | 33.7 ± 5.8 | 30.7 ± 7.1 | 0.08 |
| Race (% Caucasian) | 86 | 84 | 0.6 |
| Months postpartum | 18.0 ± 10 | 18.0 ± 10 | 1.0 |
| Body mass index (kg/m$^2$) | 29.2 ± 7.8 | 25.0 ± 5.8 | 0.02 |
| Systolic blood pressure (mmHg) | 111 ± 10 | 105 ± 8 | 0.01 |
| Diastolic blood pressure (mmHg) | 73 ± 10 | 68 ± 7 | 0.04 |
| Mean arterial blood pressure (mmHg)* | 86 ± 10 | 81 ± 7 | 0.01 |
| Oral or subcutaneous contraception (%) | 31 | 34 | 0.8 |
| Fasting glucose (mg/dL) | 81 ± 7 | 80 ± 6 | 0.5 |
| Soluble fms-like tyrosine kinase (pg/ml) | 41.6 ± 6.7 | 30.4 ± 10.2 | <0.01 |

Continuous variables are reported as mean ± standard deviation or median (interquartile range) as appropriate.

These results indicate that women with a history of pre-eclampsia during pregnancies showed elevated levels of sFlt-1 for an extended period of time after the pregnancy. Given that statistical analysis has shown that women with a history of pre-eclampsia or eclampsia have a predisposition to develop cardiovascular conditions, these results provide support for the use of sFlt-1 post-partum levels as a diagnostic indicator of a cardiovascular condition or a propensity to develop a cardiovascular condition.

EXAMPLE 11

Urine PlGF Levels as a Diagnostic Indicator of Pre-Eclampsia

In situations where obtaining serum measurements of VEGF, sFLT-1, and PlGF are not optimal, an alternative and less invasive screening method may be to measure these proteins in urine. While sFlt1 is too large a molecule (110 kDa) to be filtered into the urine in the absence of proteinuria, PlGF and VEGF, much smaller proteins (~30 kDa and 45 kDa respectively), are readily filtered. Unlike urinary PlGF, which is derived entirely from circulating blood, the major sources of urinary VEGF are cells of the kidney itself: glomerular podocytes and tubular cells. Thus, urinary VEGF is unlikely to reflect the circulating angiogenic state. We used archived urine samples to test the hypothesis that urinary PlGF is reduced well before the onset of hypertension and proteinuria and predicts pre-eclampsia.

Participants and Specimens

Serum and urine specimens were requested from participants of the CPEP clinical trial (see Example 8) before enrollment in the trial, at 26-29 weeks of gestation, at 36 weeks if they were still pregnant, and when hypertension or proteinuria was noted. Both first morning and 24-hour urine specimens were requested; if neither was available, a random or "spot" urine specimen was collected. 24-hour urines were requested from patients suspected of pre-eclampsia. "End-point specimens" referred to those obtained at or after the onset (defined below) of signs of pre-eclampsia, but before labor and delivery.

For the present study, we selected women with complete outcome information, serum samples obtained at less than 22 weeks of gestation, and a live-born male infant. This group had previously been selected for a study of fetal DNA and pre-eclampsia, in which fetal and maternal DNA were differentiated through the amplification of a gene on the Y chromosome. Analysis of previous work revealed no significant differences in maternal serum sFlt1 or PLGF concentrations according to infant gender.

Since calcium supplementation had no effect on the risk or severity of pre-eclampsia (Levine et al., supra) or on the concentrations of angiogenic factors in serum (Levine et al., N. Engl. J. Med. 350:672-683, 2004) or urine, women were chosen without regard to whether they had received calcium supplementation or placebo. For each woman with pre-eclampsia, one normotensive control was selected, matched according to enrollment site, gestational age at the collection of the first serum specimen, and storage time of the samples at −70° C. A total of 120 matched pairs were randomly chosen for analysis of all serum and urine specimens obtained before labor. If a woman had more than one urine specimen obtained on the same day, we selected one specimen, preferring first morning to random urine and random to 24-hour urine. We identified 348 urine specimens from 120 pre-eclampsia cases and 318 from 118 normotensive controls. Two normotensive controls from the serum study had no eligible urine specimens and were excluded from further analyses.

We examined separately urine samples obtained at 21-32 weeks of gestation from controls and cases with onset of pre-eclampsia before term (<37 weeks) for which a serum specimen from the same woman had been collected within 3 days. There were a total of 89 urine-serum specimen pairs from 20 cases of preterm pre-eclampsia and 69 normotensive controls.

Pre-eclampsia was defined as described above. The time of onset of pre-eclampsia (the end-point) was defined as the time of the first elevated blood-pressure or urine protein measurement leading to the diagnosis of pre-eclampsia. A small-for-gestational-age infant was defined as an infant whose birth weight was below the $10^{th}$ percentile according to U.S. tables of birth weight for gestational age that accounted for race, parity, and infant gender.

Procedures

Assays were performed by personnel who were unaware of pregnancy outcomes. Specimens were randomly ordered for analysis. Enzyme-linked immunosorbent assays (ELISAs) for sFlt, free PlGF, and free VEGF were performed in duplicate, as previously described, with the use of commercial kits (R&D Systems, Minn.). The minimal detectable doses in the assays for sFlt1, PlGF, and VEGF were 5, 7, and 5 pg per milliliter, respectively, with inter-assay and intra-assay coefficients of variation of 7.6 and 3.3 percent, respectively, for sFlt1; 10.9 and 5.6 percent, for PlGF; and 7.3 and 5.4 percent, for VEGF. Urinary creatinine was measured using a commercially available picric acid calorimetric assay (Metra creatinine assay kit, Quidel Corp., CA).

Statistical Analysis

The chi-square test was used for comparison of categorical variables; and the t-test, for comparison of continuous variables. Although arithmetic mean concentrations are reported in the text and figures, statistical testing was conducted after logarithmic transformation, using the SAS/PROC GENMOD procedure (SAS v8.0, Cary, N.C.) in crude and adjusted analyses to account for subjects with varying numbers of specimens. Odds ratios were adjusted using logistic-regression analysis.

Results

Of the 120 women with pre-eclampsia, 80 had mild and 40 had severe disease. Compared with controls, women with pre-eclampsia had greater body-mass index, higher blood pressure at enrollment in the CPEP trial, and larger proportions of their current pregnancies complicated by preterm delivery or resulting in small-for-gestational-age infants. Patient and infant characteristics have been described previously and are briefly summarized in Table 3.

Differences in Urinary PlGF after Onset of Pre-eclampsia

We first ascertained that urinary levels of PlGF were altered in women after development of clinical pre-eclampsia. Among 22 pairs of women with pre-eclampsia and gestational-age matched controls, end-point specimens had lower levels of PlGF than specimens from controls (mean PLGF level, 32 vs. 234 pg/ml, P<0.001; and 50 vs 227 pg per mg creatinine, P<0.001).

Gestational Changes in Urinary PlGF

Figure 9A:
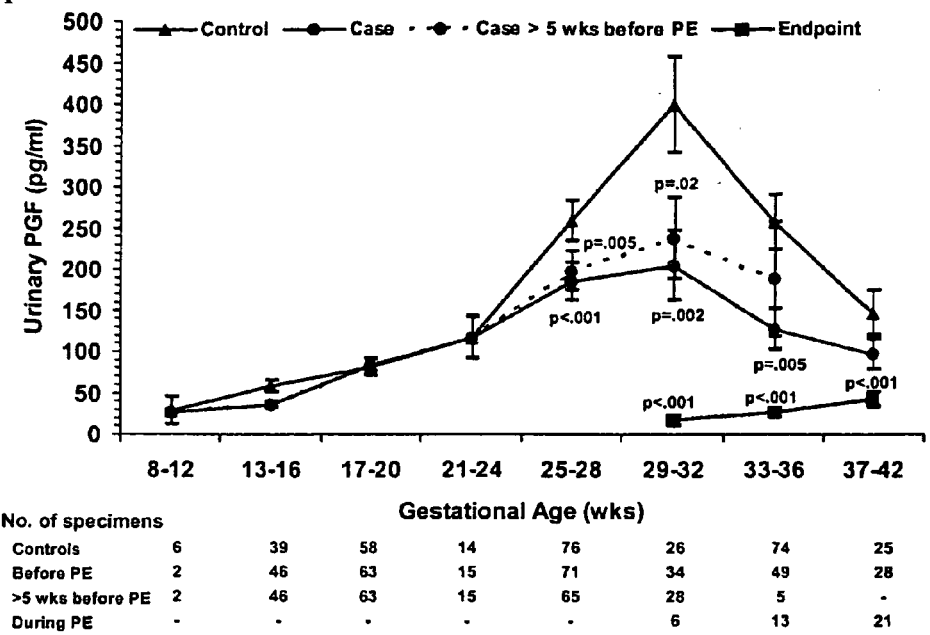
FIGS. 9A to 9D are graphs showing the concentration of urinary PlGF by intervals of gestational age.
Figure 9B:
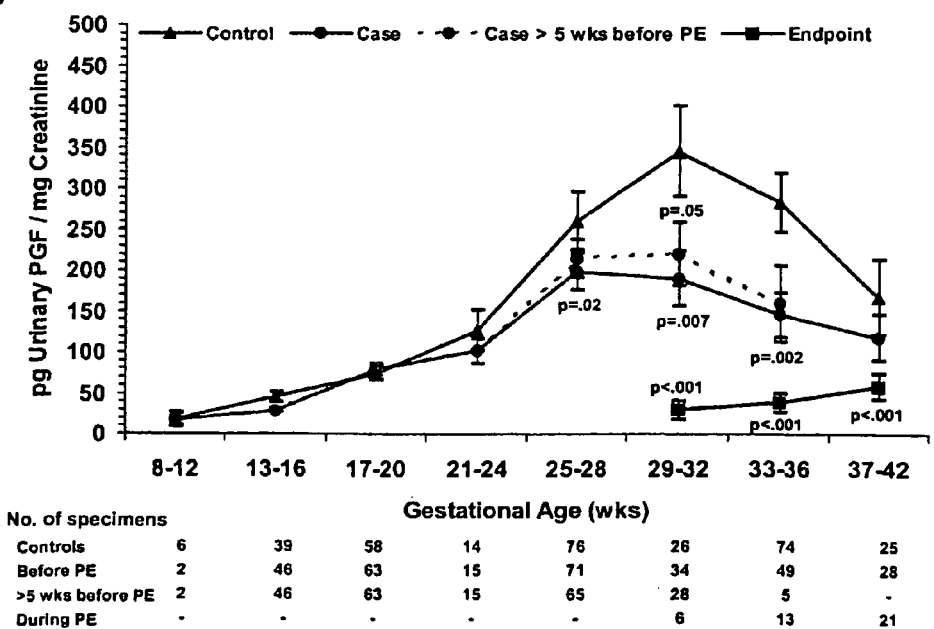

To evaluate gestational patterns, we performed cross-sectional analyses of urine obtained within gestational-age intervals of four to five weeks, with PlGF levels expressed as concentrations (FIG. 9A) or as pg per mg creatinine (FIG. 9B). The P values in FIG. 9A are for the comparisons, after logarithmic transformation, with specimens from controls obtained during the same gestational-age interval and accounting for subjects with varying numbers of specimens. The differences, after logarithmic transformation, between the specimens obtained at 29-36 weeks from women who already had clinical pre-eclampsia and those obtained at 29-36 weeks from women in whom pre-eclampsia later developed were also significant (P<0.001 for the comparison at 29-32 weeks, P<0.001 for the comparison at 33-36 weeks, and P=0.003 for the comparison at 37-42 weeks). Note that PlGF concentrations before onset of pre-eclampsia do not include endpoint specimens obtained after appearance of hypertension or proteinuria. FIG. 9A also shows the mean serum concentrations of PlGF for the women who subsequently develop pre-eclampsia after excluding specimens obtained within 5 weeks before onset of pre-eclampsia (broken red line). The graph in FIG. 9B shows that the differences, after logarithmic transformation, between the specimens obtained at 29-36 weeks from women who already had clinical pre-eclampsia and those obtained at 29-36 weeks from women in whom pre-eclampsia later developed were also significant (P=0.004 for the comparison at 29-32 weeks, P<0.001 for the comparison at 33-36 weeks, and P=0.02 for the comparison at 37-42 weeks).

Figure 9C:
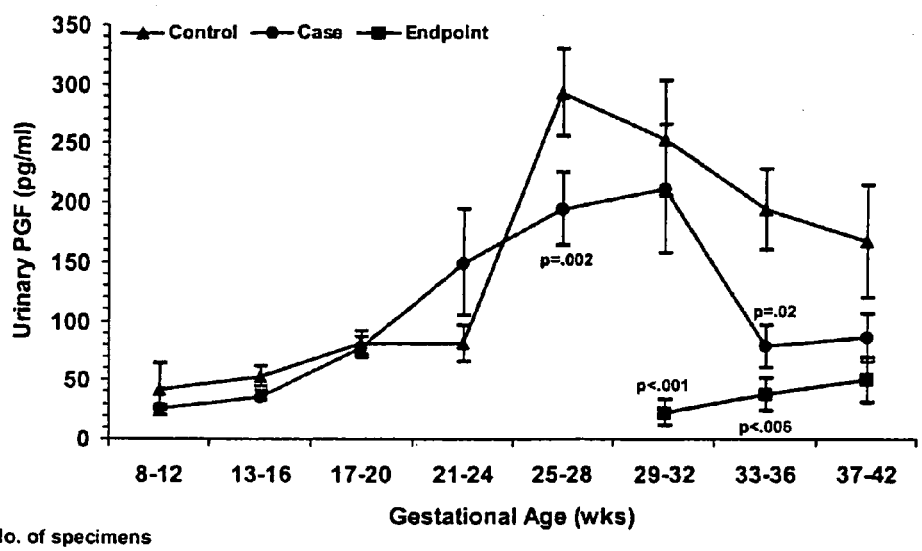
Figure 9D:
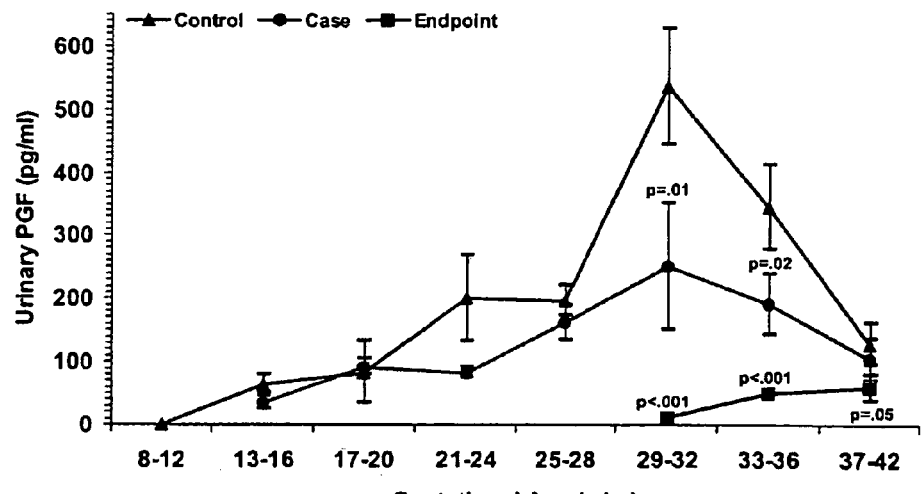

The PlGF levels in controls increased during the first two trimesters with a more rapid increase after 21-24 weeks, reaching a peak at 29-32 weeks, and decreasing thereafter. The levels in women who subsequently developed pre-eclampsia followed a similar pattern, but were significantly lower at 25-28, 29-32, and 33-36 weeks. When specimens obtained within 5 weeks before the onset of pre-eclampsia were excluded, the differences in the preceding gestational age intervals between the controls and women who later had pre-eclampsia were less pronounced. Among women with specimens obtained in the same gestational-age interval, those who already had clinical pre-eclampsia had significantly lower concentrations at 29-32, 33-36, and 37-42 weeks than those who developed pre-eclampsia later. Similar gestational age patterns among controls and cases before and after onset of clinical pre-eclampsia were observed when restricting the analysis of specimens either to first morning (FIG. 9C) or random (FIG. 9D) urines.

Relationship of Urinary PlGF to Severity of Pre-eclampsia

Figure 10:
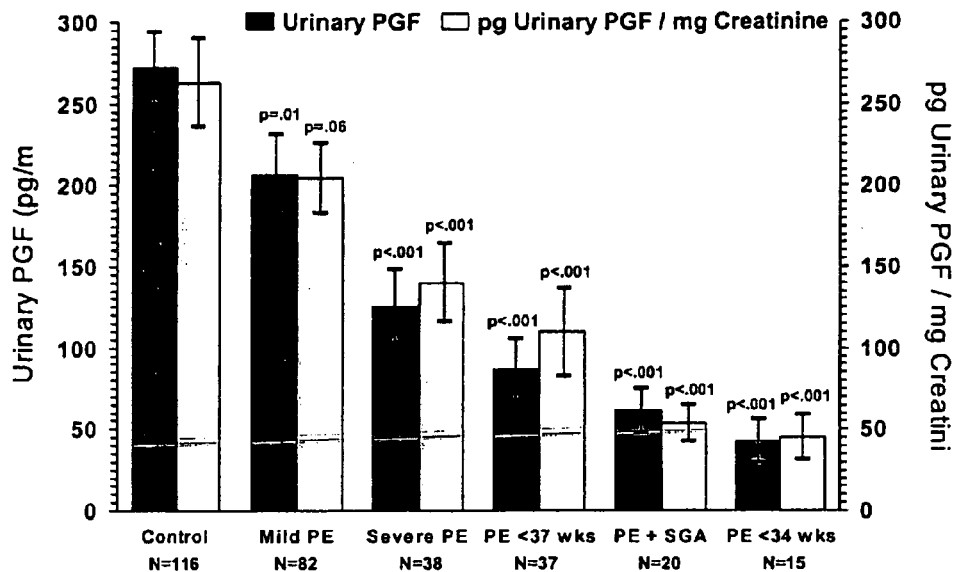
FIG. 10 is a graph showing the mean concentrations of PlGF according to pre-eclampsia status and severity, before and after normalization for creatinine. PlGF concentrations and pg per mg creatinine are shown at 21-32 weeks of gestation in controls and in women who later had clinical pre-eclampsia (PE) according to whether they had mild pre-eclampsia, severe pre-eclampsia, pre-eclampsia with an onset at less than 37 weeks of gestation, pre-eclampsia and a small-for-gestational-age infant (SGA), or pre-eclampsia with an onset at less than 34 weeks of gestation. Specimens from women in whom pre-eclampsia developed were obtained before the onset of clinical disease. The P values given are for the comparisons with the specimens from the controls. I bars represent SEs.

Before the onset of pre-eclampsia, there were particularly large differences between the levels of urinary PlGF in controls and those in women who later had pre-eclampsia with onset before 37 weeks or who had pre-eclampsia and a small-for-gestational-age infant. FIG. 10 shows PlGF concentrations and PlGF expressed as pg per mg creatinine between 21-32 weeks of gestation.

Alterations in urinary PlGF levels were also more pronounced in women who subsequently developed pre-eclampsia before term (<37 weeks of gestation) than in women who had an onset of pre-eclampsia at term (≧37 weeks) (at 21-32 weeks: PlGF concentration, 87 pg/ml in women with pre-eclampsia before term vs. 223 pg/ml in women with pre-eclampsia at term, P<0.001; at 33-42 weeks: PlGF concentration, 22 pg/ml in women with pre-eclampsia before term vs. 118 pg/ml in women with pre-eclampsia at term, P<0.001). Results were similar when using PlGF expressed as pg per mg creatinine or after adjusting PlGF concentrations for creatinine, gestational age at specimen collection, storage time, body mass index, and maternal age. Furthermore, PlGF levels in specimens obtained before onset of pre-eclampsia from women who later had pre-eclampsia and a small-for-gestational-age infant were lower than in women who later had pre-eclampsia, but whose infants were not small-for-gestational-age (at 21-32 weeks: PlGF concentration, 62 vs. 205 pg/ml, P=0.002; at 33-42 weeks: PlGF concentration, 42 vs. 123 pg/ml, P=0.06).

Odds Ratios for Pre-eclampsia Associated with Urinary PlGF

To determine the risk of pre-eclampsia according to urinary PlGF in specimens obtained before the onset of clinical signs, we divided PlGF values into quartiles based on the distribution in controls and calculated adjusted odds ratios for pre-eclampsia in each quartile, as compared to the highest quartile (Table 6) or to all other quartiles (described below).

TABLE 6

Odds Ratios for Pre-eclampsia at Less Than 37 Weeks of Gestation and at 37 Weeks or More of Gestation According to Quartile* of Urinary PlGF

| PlGF | No. of Control Specimens | PE < 37 wk No. spec. | PE < 37 wk OR (95% C.I.)** | PE ≦ 37 wks No. spec. | PE ≦ 37 wks OR (95% C.I.)** |
|---|---|---|---|---|---|
| 13-20 wks | | | | | |
| Q1: ≦29 pg/ml | 25 | 6 | 0.6 (0.2-2.4) | 19 | 0.9 (0.3-2.3) |
| Q2: 29-59 pg/ml | 24 | 12 | 1.3 (0.4-4.3) | 25 | 1.4 (0.6-3.3) |
| Q3: 59-88 pg/ml | 24 | 5 | 0.7 (0.2-2.7) | 19 | 1.1 (0.5-2.8) |
| Q4: >88 pg/ml | 24 | 6 | 1.0 | 17 | 1.0 |
| 21-32 wks | | | | | |
| Q1: ≦118 pg/ml | 29 | 30 | 31.3 (5.6-174.7) | 33 | 2.2 (1.0-5.1) |
| Q2: 118-230 pg/ml | 29 | 4 | 2.6 (0.4-16.8) | 21 | 1.3 (0.6-3.0) |
| Q3: 230-309 pg/ml | 29 | 1 | 0.6 (0.1-7.6) | 11 | 0.7 (0.3-1.7) |
| Q4: >309 pg/ml | 29 | 2 | 1.0 | 18 | 1.0 |
| 33-41 wks | | | | | |
| Q1: ≦55 pg/ml | 25 | 2 | N/A | 31 | 4.2 (1.4-12.5) |
| Q2: 55-113 pg/ml | 25 | 0 | N/A | 21 | 2.5 (0.8-7.7) |
| Q3: 113-318 pg/ml | 25 | 0 | N/A | 17 | 2.1 (0.7-6.5) |
| Q4: >318 pg/ml | 24 | 0 | N/A | 6 | 1.0 |
| pg PlGF/mg Creatinine | | | | | |
| 13-20 wks | | | | | |
| Q1: ≦26 pg/mg | 25 | 8 | 0.5 (0.1-2.2) | 21 | 0.9 (0.3-2.5) |
| Q2: 26-52 pg/mg | 24 | 9 | 0.7 (0.2-3.0) | 25 | 1.3 (0.5-3.2) |
| Q3: 52-78 pg/mg | 24 | 5 | 0.4 (0.1-1.8) | 15 | 0.8 (0.3-2.2) |
| Q4: >78 pg/mg | 24 | 7 | 1.0 | 19 | 1.0 |
| 21-32 wks | | | | | |
| Q1: ≦120 pg/mg | 29 | 29 | 15.4 (3.7-64.3) | 33 | 2.6 (1.1-6.3) |
| Q2: 120-180 pg/mg | 29 | 2 | 0.9 (0.1-6.1) | 13 | 1.0 (0.4-2.6) |
| Q3: 180-323 pg/mg | 29 | 3 | 0.9 (0.2-5.1) | 22 | 1.7 (0.7-4.0) |
| Q4: >323 pg/mg | 29 | 3 | 1.0 | 15 | 1.0 |
| 33-41 wks | | | | | |
| Q1: ≦69 pg/mg | 24 | 2 | N/A | 34 | 2.6 (1.0-6.6) |
| Q2: 69-153 pg/mg | 25 | 0 | N/A | 23 | 1.7 (0.6-4.5) |
| Q3: 153-268 pg/mg | 25 | 0 | N/A | 8 | 0.6 (0.2-1.8) |
| Q4: >268 pg/mg | 24 | 0 | N/A | 10 | 1.0 |

Quartiles were determined on the basis of control specimens
Odds ratios were adjusted for gestational age at specimen collection, specimen storage time, maternal age and body mass index (with 95% Confidence Intervals). The reference category was the highest quartile: Q4.
Specimens from cases were all obtained before onset of clinical signs of pre-eclampsia.

Among specimens obtained at 21-32 weeks of gestation the lowest quartile of PlGF was associated with a greatly increased risk of preterm pre-eclampsia and a small increased risk of pre-eclampsia at term. For preterm pre-eclampsia, after adjustment for gestational age at specimen collection, storage time, body mass index, and age, using PlGF concentration the odds ratio for the lowest quartile vs. all others was 22.5, 95% confidence interval, 7.4-67.8; and using pg PlGF per mg creatinine the odds ratio was 16.4, 95% confidence interval, 5.9-45.5. After restricting specimens to first morning urines, adjusted odds ratios were 39.5 with 95% confidence interval, 6.5-240.8; and 20.4 with 95% confidence interval, 4.5-92.3, for PlGF concentration and PlGF per mg creatinine, respectively. Using random urine specimens, adjusted odds ratios were 13.5 with 95% confidence interval, 2.3-79.8; and 11.1 with 95% confidence interval, 2.0-61.3, respectively. For term pre-eclampsia, after adjustment for the factors noted above and using all urine specimens, odds ratios were 2.2 with 95% confidence interval, 1.2-4.3; and 2.1, 95% confidence interval, 1.1-4.1, respectively. For specimens obtained at 13 to 20 weeks of gestation, the lowest quartile of PlGF was neither associated with an increased risk of preterm, nor of term pre-eclampsia. However, the lowest quartile of PlGF was associated with an increased risk of term pre-eclampsia vs. all other quartiles in specimens obtained at 33-42 weeks of gestation: adjusted odds ratio 2.3 with 95% confidence interval, 1.2-4.5, for pg PlGF per mg creatinine.

When we performed the same analyses in specimens obtained at 21-32 weeks of gestation for women who developed pre-eclampsia complicated by a small-for-gestational-age infant, we found that the estimates were unstable (adjusted OR 405, 95% confidence interval, 27-5983, for pg PlGF per mg creatinine). This was because there were only 20 such women, all of whom were in the lowest (N=19) or next lowest (N=1) quartiles of urinary PlGF. Nevertheless, the data indicate that low urinary PlGF is associated with a substantial increase in risk for pre-eclampsia with a small-for-gestational-age infant.

Gestational Changes in Urinary PlGF within Individual Women

Figure 11:
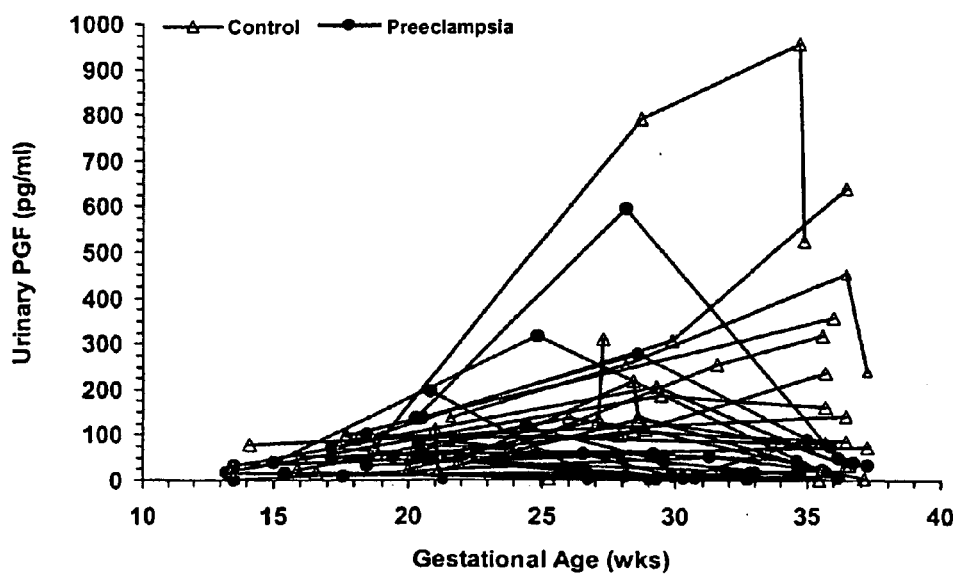
FIG. 11 is a graph showing a longitudinal plot of placental growth factor concentrations within individual women by gestational age.

FIG. 11 depicts longitudinally the changes in PlGF concentration within 13 patients with preterm pre-eclampsia (pre-eclampsia <37 weeks) and 13 controls with gestational-age matched specimens. All 13 women who developed pre-eclampsia before 37 weeks of gestation were selected who had at least a baseline urine, a urine obtained within 21-32 weeks of gestation, and an end-point urine, which might also serve as the 21-32 week specimen. Each case was matched to a control with the same or greater number of specimens obtained at similar gestational ages. One control had very low urinary PlGF per mg creatinine throughout pregnancy: 17, 5, and 0 pg/ml at 116, 177, and 248 days of gestation, respectively. This woman had a single episode of 1+proteinuria and a single diastolic blood pressure of 90 mm Hg recorded 2 hours before delivery on day 266 of gestation. Patients with preterm pre-eclampsia had lower levels of PlGF usually throughout gestation, whereas controls tended to have levels which increased with advancing gestation and fell near term.

Relationship of Urinary PlGF to Proximity to Pre-eclampsia

Urinary concentrations of PlGF in specimens obtained at 21-32 weeks of gestation and within five weeks before the onset of pre-eclampsia were lower (43 pg/ml) than in specimens obtained more than five weeks before clinical disease (196 pg/ml, P<0.001). In specimens obtained at 33-42 weeks of gestation concentrations were 110 pg/ml vs. 187 pg/ml, respectively (P=0.05). There was little difference when PlGF was normalized for creatinine.

Figure 12A:
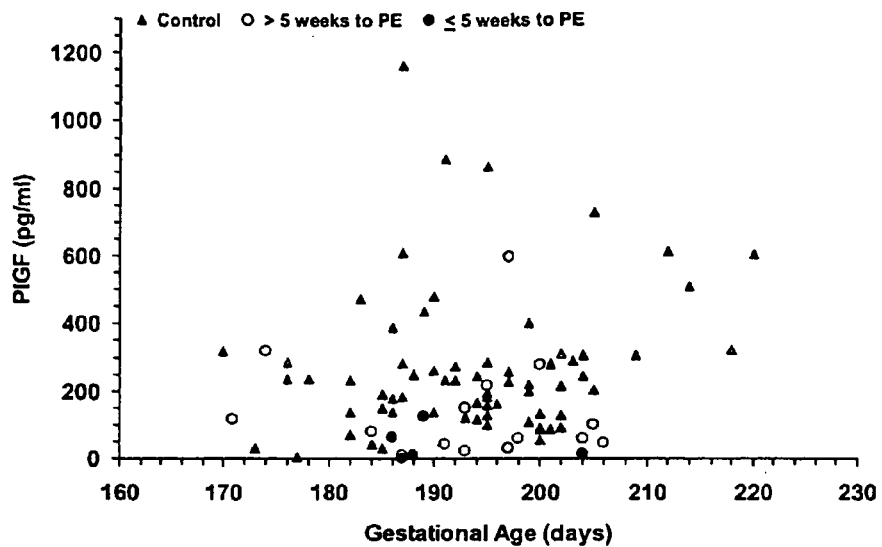
FIGS. 12A and 12B are graphs showing scatter plots of urinary PlGF concentrations and ratios of sFlt-1 to PlGF in serum at 21-32 weeks by days of gestation. Values were obtained from paired urine and serum specimens obtained from 20 women before development of pre-eclampsia at less than 37 weeks of gestation and from 69 normotensive controls.
Figure 12B:
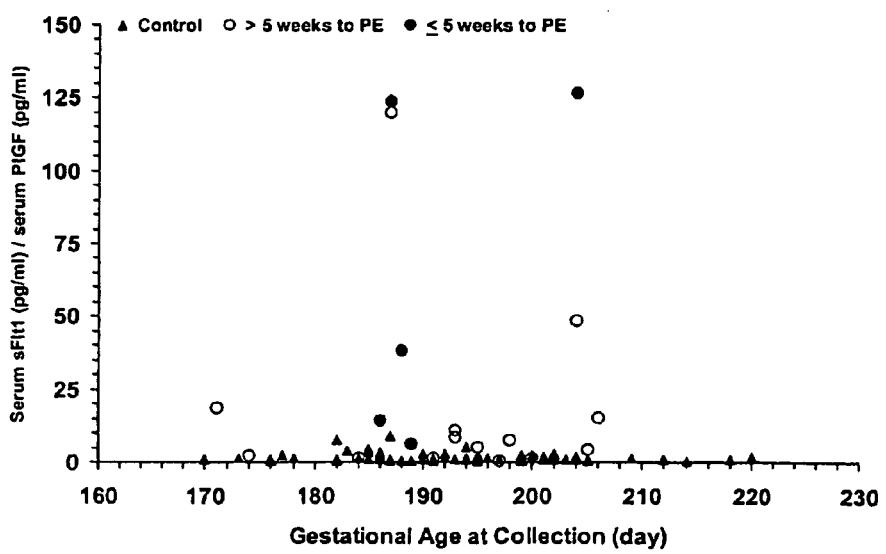

FIG. 12A is a scatter plot of urinary PlGF concentrations at 21-32 weeks from 69 controls and 20 cases who subsequently developed pre-eclampsia before term (<37 weeks). Women who developed pre-eclampsia before term had lower urinary PlGF concentrations than normotensive controls. Concentrations were lowest (i.e., less than 150 pg/ml) in specimens obtained within five weeks before the onset of clinical disease. However, a number of control specimens also had low urinary PlGF. In order to distinguish these specimens from specimens obtained within five weeks prior to pre-eclampsia, we examined serum measurements of the ratio of sFlt1 to PlGF. The ratio accounts for both the increased sFlt1 and decreased PlGF observed before onset of pre-eclampsia. A scatter plot of the ratios of sFlt1 to PlGF concentrations in paired sera is given in FIG. 12B. Ratios are elevated (>5) in all specimens obtained within five weeks before the onset of pre-eclampsia and exceed almost all control values.

Urinary sFlt1 and Urinary VEGF in Pre-Eclampsia

We randomly selected 22 cases and 22 controls for analysis of urinary sFlt1 and VEGF within 21-32 weeks of gestation before onset of clinical pre-eclampsia. In 16 of 22 case specimens (73%) and 19 of 22 control specimens (86%) urinary sFlt1 was undetectable. In contrast, urinary VEGF was detected in all specimens, but was not significantly altered in cases before or after the onset of hypertension and proteinuria (before: 272 vs. 248 pg/ml in the groups of 22 randomly selected cases and controls, respectively, P=0.56; after: 167 vs. 103 pg/ml in 22 gestational-age matched cases and controls, respectively, P=0.61).

Conclusions

In this study of 120 women with pre-eclampsia and 118 normotensive controls, urinary concentrations of PlGF were significantly lower beginning at 25-28 weeks of gestation among the women who subsequently developed pre-eclampsia. Differences between the two groups became more pronounced at 29-36 weeks. We have previously shown that serum free PlGF was lower in cases than controls beginning at 13-16 weeks of gestation, becoming even lower after 25 weeks of gestation. As with serum measurements, in the current study urinary PlGF at 21-32 weeks of gestation was significantly decreased in those who developed pre-eclampsia before 37 weeks or complicated by a small-for-gestational-age infant and within 5 weeks of the onset of clinical signs. Furthermore, among women in the lowest quartile of urinary PlGF concentrations (<118 pg/ml) at 21-32 weeks of gestation, the risk of developing pre-eclampsia before 37 weeks of gestation or complicated by a small-for-gestational-age infant was markedly elevated. The risk was high, irrespective of adjustment for urinary creatinine concentrations, and evident even in random urines. The association was, however, stronger with first morning specimens, which are likely to be more concentrated. Thus, urinary PlGF was especially useful for identifying the patients who would benefit most from early diagnosis. We have also demonstrated that a strategy of following urine measurement of PlGF with serum measurements of sFlt1 and PlGF in selected patients may minimize false positives from urine testing.

Urinary VEGF concentrations were reported recently to be modestly elevated in 37 women with severe pre-eclampsia, compared to 32 with uncomplicated pregnancy. We found non-significant elevations of urinary VEGF before and after the onset of pre-eclampsia, consistent with our hypothesis that urinary VEGF reflects primarily local renal VEGF production. Since urinary VEGF originates almost entirely from renal podocyte and tubular cells, it has not been exposed to circulating sFlt1, which is too large a molecule to filter freely through an intact glomerulus. Therefore, while reduced urinary PlGF in women with pre-eclampsia likely reflects reduced circulating free PlGF, the result of binding to excess circulating sFlt1, levels of urinary VEGF do not reflect the angiogenic imbalance in the blood.

The identification of angiogenic proteins which appear to mediate the maternal syndrome of pre-eclampsia may present specific targets for therapeutic intervention to restore the appropriate angiogenic balance (Maynard et al., supra). Prevention and treatment are especially needed for women with early onset pre-eclampsia or pre-eclampsia complicated by a small-for-gestational-age infant. However, such women must first be identified before the onset of clinical disease. These data demonstrate that a reliable and valid dipstick assay can be developed and used to screen all women for low urinary PlGF concentrations. As a follow-up for those women identified with low levels of urinary PlGF, serial serum measurements of sFlt1 and PlGF could then be used to identify more precisely individuals at high risk.

EXAMPLE 12

Ancillary Study Demonstrating Urinary PlGF During Mid-Pregnancy is a Specific Predictor of Pre-Eclampsia We performed an ancillary study to ascertain whether urinary PlGF at 21-32 weeks of gestation might differ between women with male or female infants and to determine if concentrations of urinary PlGF might be lower than normal in women with gestational hypertension and in women who remained normotensive during pregnancy, but delivered a small-for-gestational-age (SGA) infant. Among the 4256 women in the CPEP trial with adequate data who delivered a liveborn infant not known to have a chromosomal abnormality, we excluded 239 with term preeclampsia ($\geq$37 weeks). Of the 4017 women remaining, 3303 had at least one urine specimen obtained within 21-32 weeks of gestation before onset of labor or delivery and before onset of preeclampsia or gestational hypertension. Among these women we randomly selected 120 whose pregnancy was normotensive and whose infant was not SGA, 60 with normotensive pregnancy who delivered an SGA infant, 60 with gestational hypertension, and 59 with preterm (<37 weeks) preeclampsia. In each group we chose half the women to have delivered male infants and half, female infants, except for the group with preterm preeclampsia. In this group we selected 30 with male infants, but could find only 29 with female infants. PlGF was analyzed in all urine specimens obtained at 21-32 weeks gestation.

Preeclampsia, Gestational Hypertension, Small-for-Gestational-Age, and Institutional Review Board Preeclampsia was defined as a newly elevated diastolic blood pressure of at least 90 mm Hg and proteinuria of at least 1+ (30 mg per deciliter) on dipstick testing, each on two occasions 4 to 168 hours apart. Severe preeclampsia was defined as the HELLP syndrome (hemolysis, elevated liver-enzyme levels, and a low platelet count), eclampsia, or preeclampsia with either severe hypertension (diastolic blood pressure >110 mm Hg) or severe proteinuria (urinary protein excretion $\geq$3.5 g per 24 hours or findings of $\geq$3+[300 mg per deciliter] on dipstick testing). Gestational hypertension was hypertension as defined above in the absence of proteinuria. Detailed definitions have been published (Levine et al., N. Engl. J. Med. 337:69-76 (1997) and Levine et al., Control Clin. Trials 17:442-469 (1996)). The time of onset of preeclampsia was defined as the time of the first elevated blood-pressure or urine protein measurement leading to the diagnosis of preeclampsia. Similarly the onset of gestational hypertension was the time of the first elevated blood-pressure which led to the diagnosis. A small-for-gestational-age infant was an infant whose birth weight was below the $10^{th}$ percentile according to U.S. tables of birth weight for gestational age that accounted for race, parity, and infant gender (Zhang et al., Obstet. Gynecol. 86:200-208 (1995)). Because the study used data and specimens that could not be linked to identifiable women, the office of Human Subjects Research of the National Institutes of Health granted it an exemption from the requirement for review and approval by the institutional review board.

Procedures

Assays were performed by personnel who were unaware of pregnancy outcomes. Specimens were randomly ordered for analysis. Enzyme-linked immunosorbent assays (ELISAs) for sFlt1, free PlGF, and free VEGF were performed in duplicate, as previously described, with the use of commercial kits (R&D Systems, MN). (Maynard et al., supra) The minimal detectable doses in the assays for sFlt1, PlGF, and VEGF were 5, 7, and 5 pg per milliliter, respectively, with inter-assay and intra-assay coefficients of variation of 7.6 and 3.3 percent, respectively, for sFlt1; 10.9 and 5.6 percent, for PlGF; and 7.3 and 5.4 percent, for VEGF. The ELISA kits for sFlt1, VEGF and PlGF were validated for use in urine specimens with 96%, 98% and 99% recovery from spiked urine samples, respectively. Urinary creatinine was measured using a commercially available picric acid colorimetric assay (Metra creatinine assay kit, Quidel Corp., CA).

Statistical Analysis

The chi-square test was used for comparison of categorical variables; and the t-test, for comparison of continuous variables. Although arithmetic mean concentrations are reported in the text and figures, statistical testing was conducted within each time interval individually after logarithmic transformation, using the generalized estimating equations (GEE) method (SAS/PROC GENMOD procedure, SAS v8.0, Cary, N.C.) in crude and adjusted analyses to account for subjects with varying numbers of specimens. Odds ratios were adjusted with the use of logistic-regression analysis. Since matching was complete only for analyses of the earliest serum specimen in the entire study population, matching was not accounted for in the statistical analyses.

Results

In order to test further the hypothesis that decreased urinary PlGF is specific for early onset preeclampsia, we performed a second study in which we analyzed urine specimens obtained at 21-32 weeks from women with other obstetrical conditions which may share similarities of pathogenesis. We compared women with gestational hypertension and women who remained normotensive during pregnancy, but delivered an SGA infant, to normotensive women whose infant was not SGA (controls) and to women with preeclampsia before 37 weeks. The clinical characteristics of the women in this study and of their newborn infants are summarized in Table 7. The characteristics of women with preeclampsia and their infants were similar to those reported for such women in the main study.

TABLE 7

Characteristics of women in the ancillary study at CPEP enrollment and of their newborn infants

| Characteristic | Normotensive Without SGA (n = 120) | Normotensive With SGA (n = 60) | Gestational Hypertension (n = 60) | PE < 37 Wks (n = 59) |
|---|---|---|---|---|
| Age (yr) | 21.8 ± 4.6 | 21.3 ± 4.9 | 22.2 ± 5.3 | 21.1 ± 4.7 |
| Body mass index | 25.8 ± 6.1 | 22.8 ± 3.6*** | 28.3 ± 7.4* | 27.6 ± 6.9 |
| Systolic blood pressure (mm Hg) | 106 ± 9 | 106 ± 8 | 108 ± 9 | 111 ± 8† |
| Diastolic blood pressure (mm Hg) | 60 ± 7 | 60 ± 8 | 62 ± 9 | 65 ± 7*** |
| Gestational age at delivery (wks) | 39.0 ± 1.8 | 38.7 ± 1.4 | 39.6 ± 1.7 | 34.6 ± 2.3*** |
| Current smoker [n (%)] | 15 (12.5) | 13 (21.7) | 3 (5.0) | 4 (6.8) |
| Ever married [n (%)] | 34 (28.3) | 16 (26.7) | 15 (25.4) | 16 (27.1) |
| Race/ethnicity$^\phi$ | | | | |
| White, non-Hispanic [n (%)] | 46 (38.3) | 20 (33.3) | 20 (33.3) | 16 (27.1) |
| White, Hispanic [n (%)] | 16 (13.3) | 16 (26.7) | 6 (10.0) | 10 (17.0) |
| African-American [n (%)] | 55 (45.8) | 24 (40.0) | 33 (55.0) | 30 (50.9) |
| Other, unknown [n (%)] | 3 (2.5) | 0 (0.0) | 1 (1.7) | 3 (5.1) |
| Birthweight (g) | 3273 ± 456 | 2538 ± 278*** | 3437 ± 559** | 2193 ± 726*** |
| Delivery <37 wks [n (%)] | 13 (10.8) | 6 (10.0) | 3 (5.0) | 50 (84.8)*** |
| Small for gestational age (<10$^{th}$ percentile) [n (%)] | 0 (0.0) | 60 (100.0)*** | 2 (3.3) | 18 (30.5)*** |

Mean ± standard deviation unless indicated
P-values for the difference with "Normotensive without SGA"
*P = 0.02
**P = 0.04
***P < 0.001
†P = 0.001
$^\phi$Race or ethnicity was self-reported.

Compared to normotensive women whose infants were not SGA, women with gestational hypertension had greater body-mass index and infants of greater birthweight; and normotensive women with an SGA infant, lower body-mass index and infants of lower birthweight. Normotensive women with SGA infants were most likely and women with hypertensive disorders of pregnancy, least likely to have smoked during pregnancy.

Figure 13:
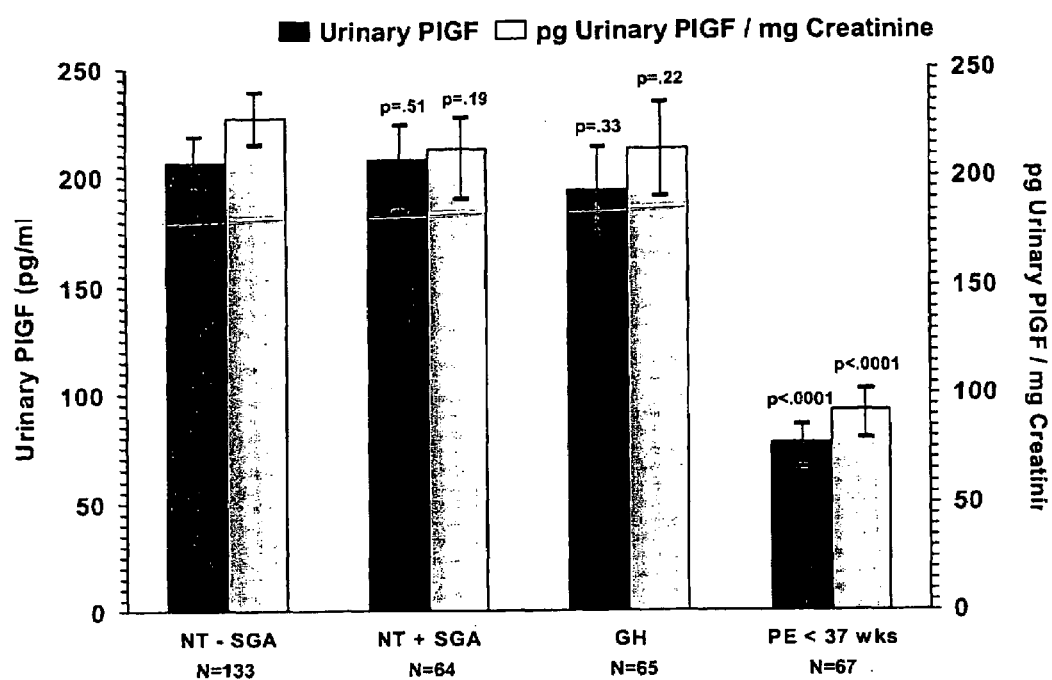
FIG. 13 is a graph showing the mean urinary concentrations of placental growth factor (PlGF) in normotensive women with infants not born small-for-gestational-age (SGA), normotensive women with SGA infants, women with gestational hypertension, and women in whom preeclampsia developed before 37 weeks of gestation. Urinary PlGF concentrations in pg/ml and in pg per mg creatinine are shown at 21-32 weeks of gestation in normotensive women whose infants were not born small-for-gestational age (NT-SGA), normotensive women with SGA infants (NT+SGA), women who subsequently developed gestational hypertension (GH), and women who subsequently developed preeclampsia before 37 weeks of gestation (PE<37 wks). Specimens from women in whom gestational hypertension or preeclampsia developed were obtained before the onset of clinical disease. The mean gestational age at specimen collection was similar in all groups. N indicates number of specimens. The P values given are for the comparisons with the specimens from the controls (NT-SGA). I bars represent SEs.

FIG. 13 depicts urinary PlGF at 21-32 weeks of gestation expressed as concentrations (pg/ml) and as pg per mg creatinine. PlGF levels in women who remained normotensive during pregnancy, but delivered an SGA infant, did not differ from those of normotensive controls whose infant was not born SGA. Similarly, levels in subjects with gestational hypertension did not differ from those of normotensive controls. However, levels of urinary PlGF in patients who developed preeclampsia before 37 weeks of gestation—collected on average 42 days prior to clinical disease—were much lower than controls (77 vs. 206 pg/ml, p<0.0001). Within each group PlGF concentrations among women who delivered male or female infants did not differ significantly.

Conclusions

Urinary PlGF was much lower at 21-32 weeks of gestation in women who developed preeclampsia before 37 weeks than in women who developed gestational hypertension or delivered a small-for-gestational-age infant, two obstetrical conditions with similarities to preeclampsia. Thus, a low urinary PlGF concentration at this stage of pregnancy can likely distinguish preeclampsia from gestational hypertension and intrauterine growth retardation.

Diagnostics

The present invention features diagnostic assays for the detection of pre-eclampsia, eclampsia, or the propensity to develop such conditions. Levels of VEGF, PlGF, or sFlt-1, either free or total levels, are measured in a subject sample and used as an indicator of pre-eclampsia, eclampsia, or the propensity to develop such conditions.

In one embodiment, a metric is used to determine whether a relationship between levels of at least two of the proteins is indicative of pre-eclampsia or eclampsia. Standard methods may be used to measure levels of VEGF, PlGF, or sFlt-1 polypeptide in any bodily fluid, including, but not limited to, urine, serum, plasma, saliva, amniotic fluid, or cerebrospinal fluid. Such methods include immunoassay, ELISA, "sandwich assays", western blotting using antibodies directed to VEGF, PlGF or sFlt-1, immunodiffusion assays, agglutination assays, fluorescent immunoassays, protein A or G immunoassays, and immunoelectrophoresis assays and quantitative enzyme immunoassay techniques such as those described in Ong et al. (*Obstet. Gynecol.* 98:608-611, 2001) and Su et al. (*Obstet. Gynecol.*, 97:898-904, 2001). ELISA assays are the preferred method for measuring levels of VEGF, PlGF, or sFlt-1. Particularly preferred, for ease and simplicity of detection, and its quantitative nature, is the sandwich or double antibody assay of which a number of variations exist, all of which are contemplated by the present invention. For example, in a typical sandwich assay, unlabeled antibody that recognizes the antigen (i.e., sFlt-1, PlGF, or VEGF polypeptide) is immobilized on a solid phase, e.g. microtiter plate, and the sample to be tested is added. After a certain period of incubation to allow formation of an antibody-antigen complex, a second antibody, labeled with a reporter molecule capable of inducing a detectable signal, is added and incubation is continued to allow sufficient time for binding with the antigen at a different site, resulting with a formation of a complex of antibody-antigen-labeled antibody. The presence of the antigen is determined by observation of a signal which may be quantitated by comparison with control samples containing known amounts of antigen.

Elevated serum levels of sFlt-1 are considered a positive indicator of pre-eclampsia. This value of sFlt-1 may be preferentially 2 ng/ml or more. Additionally, any detectable alteration in levels of sFlt-1, VEGF, or PlGF relative to normal levels is indicative of eclampsia, pre-eclampsia, or the propensity to develop such conditions. Preferably, sFlt-1 is measured, more preferably measurement of VEGF and PlGF are combined with this measurement, and most preferably all three proteins (or mRNA levels indicative of protein levels) are measured. In additional preferred embodiments, the body mass index (BMI) and gestational age of the fetus is also measured and included the diagnostic metric.

In another embodiment, the PAAI (sFlt-1/VEGF+PlGF) is used as an anti-angiogenic index that is diagnostic of pre-eclampsia, eclampsia, or the propensity to develop such conditions. If the PAAI is greater than 10, more preferably greater than 20, then the subject is considered to have pre-eclampsia, eclampsia, or to be in imminent risk of developing the same. The PAAI (sFlt-1/VEGF+PlGF) ratio is merely one example of a useful metric that may be used as a diagnostic indicator. It is not intended to limit the invention. Virtually any metric that detects an alteration in the levels of any of sFlt-1, PlGF, or VEGF in a subject relative to a normal control may be used as a diagnostic indicator.

Expression levels of particular nucleic acids or polypeptides may be correlated with a particular disease state (e.g., pre-eclampsia or eclampsia), and thus are useful in diagnosis. Oligonucleotides or longer fragments derived from a sFlt-1, PlGF, or VEGF nucleic acid sequence may be used as a probe not only to monitor expression, but also to identify subjects having a genetic variation, mutation, or polymorphism in an sFlt-1, PlGF, or VEGF nucleic acid molecule that are indicative of a predisposition to develop the conditions. Such polymorphisms are known to the skilled artisan and are described, for example, by Parry et al. (*Eur. J. Immunogenet.* 26:321-3, 1999). A survey of the GenBank database (www.ncbi.nlm.nih.gov) reveals at least 330 known polymorphisms in the gene and the promoter region of Flt-1/sFlt-1. These polymorphisms may affect sFlt-1 nucleic acid or polypeptide expression levels or biological activity. Detection of genetic variation, mutation, or polymorphism relative to a normal, reference sample can be as a diagnostic indicator of pre-eclampsia, eclampsia, or the propensity to develop pre-eclampsia or eclampsia.

Such genetic alterations may be present in the promoter sequence, an open reading frame, intronic sequence, or untranslated 3' region of an sFlt-1 gene. Information related to genetic alterations can be used to diagnose a subject as having pre-eclampsia, eclampsia, or a propensity to develop such conditions. As noted throughout, specific alterations in the levels of biological activity of sFlt-1, VEGF, and/or PlGF can be correlated with the likelihood of pre-eclampsia or eclampsia, or the predisposition to the same. As a result, one skilled in the art, having detected a given mutation, can then assay one or more metrics of the biological activity of the protein to determine if the mutation causes or increases the likelihood of pre-eclampsia or eclampsia.

In one embodiment, a subject having pre-eclampsia, eclampsia, or a propensity to develop such conditions will show an increase in the expression of a nucleic acid encoding sFlt-1 or an alteration in PlGF or VEGF levels. Methods for detecting such alterations are standard in the art and are described in Ausubel et al., supra. In one example northern blotting or real-time PCR is used to detect sFlt-1, PlGF, or VEGF mRNA levels.

In another embodiment, hybridization with PCR probes that are capable of detecting an sFlt-1 nucleic acid molecule, including genomic sequences, or closely related molecules, may be used to hybridize to a nucleic acid sequence derived from a subject having pre-eclampsia or eclampsia or at risk of developing such conditions. The specificity of the probe, whether it is made from a highly specific region, e.g., the 5' regulatory region, or from a less specific region, e.g., a conserved motif, and the stringency of the hybridization or amplification (maximal, high, intermediate, or low), determine whether the probe hybridizes to a naturally occurring sequence, allelic variants, or other related sequences. Hybridization techniques may be used to identify mutations indicative of a pre-eclampsia or eclampsia in an sFlt-1 nucleic acid molecule, or may be used to monitor expression levels of a gene encoding an sFlt-1 polypeptide (for example, by Northern analysis, Ausubel et al., supra).

In yet another embodiment, humans may be diagnosed for a propensity to develop pre-eclampsia or eclampsia by direct analysis of the sequence of an sFlt-1, VEGF, or PlGF nucleic acid molecule.

A subject having pre-eclampsia, eclampsia, or a propensity to develop such conditions will show an increase in the expression of an sFlt-1 polypeptide. The sFlt-1 polypeptide can include full-length sFlt-1, degradation products, alternatively spliced isoforms of sFlt-1, enzymatic cleavage products of sFlt-1, and the like. An antibody that specifically binds an sFlt-1 polypeptide may be used for the diagnosis of pre-eclampsia or eclampsia or to identify a subject at risk of developing such conditions. A variety of protocols for measuring an alteration in the expression of such polypeptides are known, including immunological methods (such as ELISAs and RIAs), and provide a basis for diagnosing pre-eclampsia or eclampsia or a risk of developing such conditions. Again, an increase in the level of the sFlt-1 polypeptide is diagnostic of a subject having pre-eclampsia, eclampsia, or a propensity to develop such conditions.

In one embodiment, the level of sFlt-1, VEGF, or PlGF polypeptide or nucleic acid, or any combination thereof, is measured at least two different times and an alteration in the levels as compared to normal reference levels over time is used as an indicator of pre-eclampsia, eclampsia, or the propensity to develop such conditions. In another embodiment, the level of sFlt-1, VEGF, or PlGF polypeptide or nucleic acid, or any combination thereof is compared to the level in a reference sample.

The level of sFlt-1, VEGF, or PlGF polypeptide can also be compared to a standard curve to determine if it falls within "normal ranges" of the level of polypeptide. In this embodiment, a standard curve is established for each of the polypeptides using purified or recombinant forms (e.g., greater than 80%, 90%, 95%, 99% or 100% pure) of the polypeptide for comparison. A standard curve is generated and the concentration of the polypeptide is determined by comparison to a standard curve established for the same polypeptide. For example, a standard curve can be established for sFlt-1 and a subject sample that, when compared to the standard curve, has sFlt-1 concentrations greater than 2 ng/mL is considered indicative of pre-eclampsia, eclampsia, or the propensity to develop such conditions.

The level of sFlt-1, VEGF, or PlGF in the bodily fluids of a subject having pre-eclampsia, eclampsia, or the propensity to develop such conditions may be altered (increased or decreased) by as little as 10%, 20%, 30%, or 40%, or by as much as 50%, 60%, 70%, 80%, or 90% or more relative to the level of sFlt-1, VEGF, or PlGF in a normal control. The level of sFlt-1 present in the bodily fluids of a subject having pre-eclampsia, eclampsia, or the propensity to develop such conditions may be increased by 1.5-fold, 2-fold, 3-fold, 4-fold or even by as much as 10-fold or more relative to levels in a normal control subject.

In one embodiment, a subject sample of a bodily fluid (e.g., urine, plasma, serum, amniotic fluid, or cerebrospinal fluid) is collected early in pregnancy prior to the onset of pre-eclampsia symptoms. In another example, the sample can be a tissue or cell collected early in pregnancy prior to the onset of pre-eclampsia symptoms. Non-limiting examples include placental tissue, placental cells, endothelial cells, and leukocytes such as monocytes. In humans, for example, maternal blood serum samples are collected from the antecubital vein of pregnant women during the first, second, or third trimesters of the pregnancy. Preferably, the assay is carried out during the first trimester, for example, at 4, 6, 8, 10, or 12 weeks, or during the second trimester, for example at 14, 16, 18, 20, 22, or 24 weeks. Such assays may also be conducted at the end of the second trimester or the third trimester, for example at 26, 28, 30, 32, 34, 36, 37, 38, 39, or 40 weeks. It is preferable that levels of sFlt-1, VEGF, or PlGF be measured twice during this period of time. For the diagnosis of post-partum pre-eclampsia or eclampsia, assays for sFlt-1, VEGF, or PlGF may be carried out postpartum.

In one particular example, serial blood samples can be collected during pregnancy and the levels of soluble sFlt-1 determined by ELISA. In one study using this technique, the alternatively spliced mRNA encoding sFlt-1 is highly expressed by trophoblast cells and the protein was readily detectable in the plasma of pregnant women. It was observed that the levels of sFlt-1 increased approximately 3-fold between 20 and 36 weeks gestation. Levels were observed to be significantly higher in high-risk women who subsequently went on to develop pre-eclampsia (Charnock-Jones et al., *J. Soc. Gynecol. Investig.* 10(2):230, 2003).

In one preferred embodiment, PlGF polypeptide levels are measured in a bodily fluid sample, preferably urine, and used as a diagnostic indicator of pre-eclampsia, eclampsia, or the propensity to develop the same. Measurements of PlGF polypeptide levels in the urine can also be used as an initial assessment of the potential risk for pre-eclampsia or eclampsia and a woman determined to be "at risk" by PlGF measurements can then undergo additional diagnostic assays such as the ones described herein or known in the art. In one example, a woman diagnosed with a risk of developing pre-eclampsia or eclampsia by PlGF polypeptide measurement in a urine sample is further monitored by serum analysis of VEGF, sFlt-1, and/or PlGF levels as described above. In another example, the PAAI is determined using the serum values for each of these polypeptides. A woman identified as having a risk of developing pre-eclampsia or eclampsia by urine analysis for PlGF can be monitored regularly prior to pregnancy, throughout the pregnancy (e.g., every month, every three weeks, every two weeks, weekly, every third day, every other day, or daily), or after the pregnancy.

The free form of PlGF has an average molecular weight of about 30 kDa and is small enough to be filtered by the kidney and released into the urine. PlGF, when complexed to sFlt-1, has a much greater molecular weight and would therefore not be released into the urine. Although not wishing to be bound by theory, the inventors have discovered that during pre-eclampsia, when the levels of sFlt-1 are increased, sFlt-1 can complex to PlGF, thereby reducing the levels of free PlGF released into the urine. As a result, urine analysis for free PlGF levels can be used to diagnose pre-eclampsia or eclampsia or a patient at risk for having the same. In order to detect free PlGF, it is preferred that an antibody that specifically recognizes free PlGF is used for these assays. Such an antibody can recognize, for example, the sFlt-1 binding domain of PlGF. Examples of such a specific antibody include the capture antibody used in the human PlGF ELISA kit (catalog #DPG000, R&D Systems, Minneapolis, Minn.), monoclonal anti-placental growth factor (clone 37203.111, Sigma-Aldrich, St. Louis, Mo.). These antibodies recognize specific sequences in the N-terminal region of human PlGF protein. The sFlt1 binding region to PlGF is between amino acids 39-105 of the PlGF protein, wherein the total length of PlGF varies from 149 to 221 amino acids depending on the isoform of PlGF. Additional preferred antibodies include any antibody that recognizes the N-terminal region (preferably between amino acids 39-105 of PlGF) and that will specifically bind to free PlGE and not PlGF bound to sFlt-1. Antibodies raised to C-terminus will not have this property.

As with any of the diagnostic assays of the invention, PlGF levels in a subject sample can be compared to a reference sample to determine relative levels A reference sample can be a urine sample from a patient having pre-eclampsia (generally having a level of free PlGF less than 400 pg/ml, preferably less than 200 pg/ml) or from a normal urine sample (having a PlGF concentration ranging from 200 pg/ml to 800 pg/ml) depending on the desired use of the diagnostic assay. The PlGF levels can also be compared to a reference value or standard to determine absolute levels. The reference value or standard can be determined using a standard curve established based on purified or recombinant forms (e.g., greater than 80%, 90%, 95%, 99% or 100% pure) of PlGF for comparison. A value of PlGF less than 400 pg/ml, preferably less than 200 pg/ml, and most preferably less than 100 pg/ml or a PlGF/creatinine value less than 200 pg/mg of creatinine and preferably less than 100 pg/mg of creatinine is considered a diagnostic indicator of pre-eclampsia or eclampsia or a patient at risk for having the same. For standard curves, recombinant PlGF ranging from 10 pg/ml to 1 ng/ml can be used. Other examples of recombinant proteins that can be used to generate the standard curves include specific peptides that encompass the amino terminus of PlGF, preferably amino acids 39-105 of the PlGF protein (the region of PlGF that binds to sFlt-1). Alternatively, a recombinant PlGF/VEGF heterodimer (available commercially as catalog # 297-VP, R &D Systems, MN) can also be used. The latter has the advantage that this protein may also be used to generate the VEGF standard curve in the measurement of free VEGF.

ELISA assays are the preferred method for measuring levels of free PlGF. Particularly preferred, for ease and simplicity of detection, and its quantitative nature, is the sandwich or double antibody ELISA assay of which a number of variations exist, all of which are contemplated by the present invention. For example, in a typical sandwich assay, unlabeled antibody that recognizes the PlGF polypeptide is immobilized on a solid phase, e.g. microtiter plate, and the sample to be tested is added. After a certain period of incubation to allow formation of an antibody-antigen complex, a second antibody, labeled with a reporter molecule capable of inducing a detectable signal, is added and incubation is continued to allow sufficient time for binding with the antigen at a different site, resulting with a formation of a complex of antibody-antigen-labeled antibody. The presence of the antigen is determined by observation of a signal which may be quantitated by comparison with control samples containing known amounts of antigen.

In an example of the quantitative sandwich ELISA, a solid support (e.g., a microtiter plate or a membrane) is pre-coated with an anti-PlGF binding agent (e.g., a primary antibody). Standards or samples are added to the substrate and PlGF, if present, will bind to the antibody. A standardized preparation of enzyme-conjugated antibody that also recognizes PlGF is then added to "sandwich" the PlGF now immobilized on the plate. The substrate is added and the enzyme and substrate are allowed to react over a short incubation period. The enzyme-substrate reaction is terminated and the change is measured by art known methods (e.g., by eye, using a spectrophotometer, or measuring chemiluminescence). Such an assay can be used to determine the relative level of PlGF (e.g., as compared to the level in a reference sample, standard or level) or to determine the absolute concentration of PlGF. If so desired, the concentration of PlGF can be determined using a set of calibration standards of purified PlGF at varying concentrations. The calibration standards are assayed at the same time as the sample and are used to produce a standard curve measured by, for example, optical density, versus PlGF concentration. The concentration of PlGF in the sample is then determined by comparing, for example, the optical density of the samples to the standard curve. The concentrations of PlGF during normal pregnancy during mid-gestation and late-gestation will range from 200-800 pg/ml depending on the gestational age of the mother. Any value of urinary PlGF less than 400 pg/ml, preferably less than 200 pg/ml or a value of urinary PlGF less than 200 pg/mg of creatinine will be diagnostic of preeclampsia. In general, the standard curves on the ELISA kit will include recombinant or purified PlGF at concentrations ranging from 10 pg/ml-1 ng/ml of PlGF.

In another example, an assay for detecting PlGF in a urine sample includes a membrane having an immobilized PlGF binding agent that is detectably labeled in a manner that can distinguish between the PlGF when it is bound to free PlGF and when it is not bound to free PlGF. Preferred labels include fluorescent labels. The membrane is exposed to the sample for a time sufficient to allow binding of the PlGF binding agent to free PlGF present in the sample. The labeled PlGF binding agent bound to the free PlGF is then measured. Such an assay can be used to determine the relative level of PlGF (e.g., as compared to the level from a reference sample or standard or level) or to determine the absolute concentration of PlGF as described above. Preferred assays for the measurement of binding include fluorescence immunoassays.

In another example, an assay for detecting PlGF in a urine sample includes a membrane having a dehydrated labeled (e.g., for colorimetric detection) PlGF binding agent (primary agent) and an immobilized anti-PlGF binding agent (secondary agent). The membrane is exposed to the sample. The sample rehydrates the labeled PlGF binding agent and if PlGF is present in the sample, it will bind to the PlGF binding agent. The PlGF-primary agent complex will move down the membrane by capillary movement and will interact with the immobilized secondary agent. This interaction will produce a visible line from the colorimetric label at the position at which the secondary agent is immobilized.

In another example, an assay for detecting PlGF in a urine sample includes a membrane having a dehydrated labeled (e.g., for calorimetric detection) PlGF binding agent (primary agent), and an immobilized anti-PlGF binding agent (secondary agent). The membrane also includes purified PlGF at a threshold concentration also immobilized on the membrane. In this example, the membrane is exposed to the urine sample. The sample rehydrates the labeled primary agent and if PlGF is present in the sample at a concentration greater than the threshold concentration, it will bind to the PlGF binding agent. The PlGF-labeled primary agent complex will move down the membrane by capillary movement. As the primary agent is already bound to the PlGF from the sample, it will not bind to the immobilized purified PlGF and no visible line will appear at this "test" position. The PlGF-primary agent complex will continue down the membrane and will interact with the immobilized secondary agent. This interaction will produce a visible line from the calorimetric label at the "control" position at which the anti-PlGF binding agent is immobilized. In this example, only one visible line will appear and will indicate a PlGF concentration above a threshold concentration. If the concentration of PlGF is below the threshold concentration, the labeled primary agent will bind to the immobilized PlGF and a visible line will appear at this "test" location as well as at the "control" location. The test assay can also include multiple test lines aimed at detecting several concentrations of PlGF in the sample. Such a graded assay is described in U.S. Pat. No. 6,660,534.

In another example, a similar membrane based assay is used but is based on standard sandwich ELISA methods. In this example, the membrane includes a reaction zone having an immobilized primary PlGF binding agent conjugated to an enzyme; a test zone having another immobilized PlGF binding agent that binds to a region of PlGF not bound by the first PlGF binding agent, and a control zone having an immobilized substance that recognizes the primary PlGF binding agent. In both the test zone and the control zone a detectable substrate for the enzyme conjugated to the first immobilized PlGF binding agent is included. The membrane is exposed to the sample and the sample moves to the reaction zone by capillary action. If PlGF is present in the sample, it binds to the first immobilized PlGF binding agent conjugated to an enzyme and forms a complex which is then carried along by capillary flow to the test zone. The PlGF-immobilized PlGF binding agent conjugated to an enzyme complex then binds to the second PlGF binding agent and forms a visible line at the location of the immobilized second PlGF binding agent (the "test" zone). The remaining first PlGF binding agent is carried along by capillary flow and will bind to the immobilized substance that recognizes or binds to the first binding agent and produce a visible line at this location (the "control" zone). If PlGF is not present in the sample, only the second line will appear at the control zone. In preferred embodiments, the first and second PlGF binding agents are antibodies and the agent that recognizes or binds to the first binding agent is a secondary anti-immunoglobulin antibody that specifically recognizes the immunoglobulin of the first antibody. The intensity of the line in the test zone can be compared to assays using a standard amount of purified PlGF protein to determine if the sample contains PlGF above or below a threshold concentration.

In any of the assays described herein, normal pregnant serum can be used as an additional control and the activity of PlGF can be measured and quantified as a percentage of PlGF activity measured from normal pregnant serum.

For any of the assays described herein, the sample can be any bodily fluid. A urine sample is preferred for the PlGF-based diagnostic assays. The membrane can be in a standard dipstick type format or lateral flow format. The dipstick type of assay is known in the art for such assays as pregnancy detection (measuring hormone levels in that case) or urinalysis detection of creatinine or albumin in the diagnosis of kidney disease. Examples of various formats of dipstick type assays are described in U.S. Pat. No. 6,660,534, incorporated herein by reference.

Any of the above PlGF detection assays can be used alone or in combination with additional diagnostic assays described herein or in the art. In a preferred embodiment, the PlGF diagnostic assay is used as an initial screen followed by assays for the measurement of serum sFlt-1, PlGF and/or VEGF levels as described herein. In this way "at risk" patients can be identified and carefully monitored or screened further for even greater diagnostic accuracy.

In preferred embodiments of any of the above-described PlGF-based diagnostic assays, the PlGF binding agent is preferably a primary antibody that recognizes PlGF or a protein or peptide that interacts with PlGF. The secondary anti-PlGF binding agent is preferably a secondary antibody that recognizes the primary antibody or a protein that binds to the primary antibody (e.g., Protein A or Protein G), or an antibody that specifically binds the peptide that interacts with PlGF. In embodiments where the PlGF binding agent is labeled with an enzyme, the enzyme used preferably catalyzes a calorimetric reaction that can be detected by eye and/or measured by spectrophotometry. Non-limiting examples of preferred enzyme/substrate combinations are horseradish peroxidase/TMB, β-galactosidase/XGAL, and alkaline/phosphatase/1,2 dioxetane. For embodiments that include a labeled PlGF binding agent, preferred labels include colorimetric (e.g., colloidal gold), chemiluminescent, or fluorescent labels.

In veterinary practice, assays may be carried out at any time during the pregnancy, but are, preferably, carried out early in pregnancy, prior to the onset of pre-eclampsia symptoms. Given that the term of pregnancies varies widely between species, the timing of the assay will be determined by a veterinarian, but will generally correspond to the timing of assays during a human pregnancy.

The diagnostic methods described herein can be used individually or in combination with any other diagnostic method described herein for a more accurate diagnosis of the presence of, severity of, or estimated time of onset of pre-eclampsia or eclampsia. In addition, the diagnostic methods described herein can be used in combination with any other diagnostic methods determined to be useful for the accurate diagnosis of the presence of, severity of, or estimated time of onset of pre-eclampsia or eclampsia.

The diagnostic methods described herein can also be used to monitor and manage pre-eclampsia or eclampsia in a subject. In one example, if a subject is determined to have a serum sFlt-1 protein level of 10 ng/mL and a serum level of free PlGF of 100 pg/mL, then VEGF can be administered until the serum PlGF level rises to approximately 400 pg/mL. In this embodiment, the levels of sFlt-1, PlGF, and VEGF, or any and all of these, are measured repeatedly as a method of not only diagnosing disease but monitoring the treatment and management of the pre-eclampsia and eclampsia. As described above, in normal pregnancies, urinary levels of PlGF range from 200-800 pg/ml or 200-800 pg/mg of creatinine after 20 weeks of gestation. A value of PlGF less than 400 pg/ml, preferably less than 200 pg/ml or 200 pg/mg of creatinine in a urine sample is considered diagnostic of preeclampsia or a propensity to develop pre-eclampsia.

The invention also features diagnostic assays for the detection of a cardiovascular condition or a propensity to develop a cardiovascular condition. In a preferred embodiment, sFlt-1 levels are measured in women with a history of pre-eclampsia or eclampsia and compared to sFlt-1 levels from a reference sample. Reference samples preferably include samples taken from women with previous pregnancies and no history of pre-eclampsia or eclampsia. Alterations in the levels of sFlt-1 polypeptide or nucleic acid as compared to the reference sample can be used to diagnose a cardiovascular condition or to predict a propensity to develop a cardiovascular condition. Alterations in the nucleic acid sequence of sFlt-1, PlGF, or VEGF as compared to a reference sequence can also be used to diagnose a cardiovascular condition or to predict a propensity to develop a cardiovascular condition. Any of the diagnostic methods and metrics described above can be used to monitor women with a history of pre-eclampsia or eclampsia post-partum or to diagnose a cardiovascular condition or to predict a propensity to develop a cardiovascular condition. Post-partum monitoring can be performed on a regular basis (e.g., once a month, once every six months, yearly, every other year, or less frequently) to assist in the diagnosis, prediction, or prevention of future cardiovascular events or conditions.

Diagnostic Kits

The invention also provides for a diagnostic test kit. The diagnostic test kit includes the components required to carry out any of the diagnostic assays described above and instructions for the use of the components to diagnose pre-eclampsia or eclampsia or the propensity to develop pre-eclampsia or eclampsia. For example, a diagnostic test kit can include antibodies to sFlt-1, VEGF, or PlGF, and components useful for detecting, and more preferably evaluating, binding between the antibodies and the sFlt-1, VEGF, or PlGF polypeptide. For detection, either the antibody or the sFlt-1, VEGF, or PlGF polypeptide is labeled, and either the antibody or the sFlt-1, VEGF, or PlGF polypeptide is substrate-bound, such that the sFlt-1, VEGF, or PlGF polypeptide-antibody interaction can be established by determining the amount of label attached to the substrate following binding between the antibody and the sFlt-1, VEGF, or PlGF polypeptide. In one example, the kit includes a PlGF binding agent and components for detecting the presence of PlGF. A conventional ELISA or a sandwich ELSIA is a common, art-known method for detecting antibody-substrate interaction and can be provided with the kit of the invention. sFlt-1, VEGF, or PlGF polypeptides can be detected in virtually any bodily fluid including, but not limited to urine, serum, plasma, saliva, amniotic fluid, or cerebrospinal fluid. A kit that determines an alteration in the level of sFlt-1, VEGF, or PlGF polypeptide relative to a reference, such as the level present in a normal control, is useful as a diagnostic kit in the methods of the invention. The kit can also include purified proteins to be used as standards in the assay used to detect the level of sFlt-1, VEGF, or PlGF. Desirably, the kit will contain instructions for the use of the kit. In one example, the kit contains instructions for the use of the kit for the diagnosis of pre-eclampsia, eclampsia, or the propensity to develop pre-eclampsia or eclampsia. In another example, the kit contains instructions for the diagnosis of cardiovascular conditions or the propensity to develop cardiovascular conditions. In yet another example, the kit contains instructions for the use of the kit to monitor therapeutic treatment or dosage regimens.

In one embodiment of the invention, such a kit includes a solid support (e.g., a membrane or a microtiter plate) coated with a primary agent (e.g., an antibody or protein that recognizes the antigen), standard solutions of purified protein for preparation of a standard curve, a body fluid (e.g. serum or urine) control for quality testing of the analytical run, a secondary agent (e.g., a second antibody reactive with a second epitope in the antigen to be detected or an antibody or protein that recognizes the primary antibody) conjugated to a label or an enzyme such as horse radish peroxidase or otherwise labelled, a substrate solution, a stopping solution, a washing buffer and an instruction manual.

Assays for Gene and Protein Expression

Blood serum from the subject is measured for levels of VEGF, PlGF, or any protein ligand known to bind to sFlt-1. Methods used to measure serum levels of proteins include ELISA, western blotting, or immunoassays using specific antibodies. In addition, biological activity can be determined using an in vitro angiogenesis assay to determine if the subject's blood has converted from an anti-angiogenic state to a pro-angiogenic state. Such assays are described above in Example 2.

Blood serum samples from the subject can also be measured for levels of VEGF, PlGF or sFlt-1 nucleic acid levels.

There are several art-known methods to assay for gene expression. Some examples include the preparation of RNA from the blood samples of the subject and the use of the RNA for northern blotting, PCR based amplification, or RNAse protection assays.

Subject Monitoring

The disease state or treatment of a subject having pre-eclampsia, eclampsia, or a propensity to develop such a condition can be monitored using the methods and compositions of the invention. In one embodiment, the expression of an sFlt-1, VEGF, or PlGF polypeptide present in a bodily fluid, such as urine, plasma, amniotic fluid, or CSF, is monitored. Such monitoring may be useful, for example, in assessing the efficacy of a particular drug in a subject or in assessing disease progression. Therapeutics that decrease the expression of an sFlt-1 nucleic acid molecule or polypeptide or that increase the expression of a VEGF or PlGF nucleic acid molecule or polypeptide are taken as particularly useful in the invention.

Other Embodiments

From the foregoing description, it is apparent that variations and modifications may be made to the invention described herein to adopt it to various usages and conditions. Such embodiments are also within the scope of the following claims.

All publications mentioned in this specification are herein incorporated by reference to the same extent as if each independent publication or patent application was specifically and individually indicated to be incorporated by reference. In addition, U.S. application publication number 2004-0126828 and PCT publication number WO2004/008946A2 are hereby incorporated by reference in their entirety.

What is claimed is:

1. A method of diagnosing a pregnant human subject as having, or having a propensity to develop, pre-eclampsia or eclampsia, said method comprising:
   (a) measuring the level of free PlGF in a urine sample from said pregnant human subject, wherein said free PlGF is a PlGF polypeptide that has the ability to bind to sFlt-1; and
   (b) measuring the level of sFlt-1 in a bodily fluid sample from said pregnant human subject;
   wherein a level of free PlGF in said urine sample less than 400 pg/ml and a level of sFlt-1 polypeptide greater than 2 ng/ml measured during mid-gestation or late gestation is a diagnostic indicator of pre-eclampsia or eclampsia or a propensity to develop pre-eclampsia or eclampsia.

2. A method of diagnosing a pregnant human subject as having, or having a propensity to develop, pre-eclampsia or eclampsia, said method comprising measuring the level of free PlGF in a urine sample from said pregnant subject, wherein said sample is obtained during mid-gestation or late gestation, and measuring the level of creatinine in said urine sample, wherein said free PlGF is a PlGF polypeptide that than 200 pg per mg of creatinine is a diagnostic indicator of pre-eclampsia or eclampsia or a propensity to develop pre-eclampsia or eclampsia.

3. A method of diagnosing a pregnant human subject as having a propensity to develop, early onset pre-eclampsia or eclampsia, said method comprising measuring the level of free PlGF in a urine sample from said pregnant subject at 21-32 weeks and measuring the level of creatinine in said urine sample and comparing said level of free PlGF per mg of creatinine from said subject to the level of free PlGF per mg of creatinine from a reference sample, wherein said free PlGF is a PlGF polypeptide that has the ability to bind to sFlt-1 and wherein a decrease of at least 50% in said free PlGF per mg of creatinine from the subject sample compared to said reference sample is a diagnostic indicator of a propensity to develop early onset pre-eclampsia or eclampsia.

4. The method of claim 3, wherein said reference sample is a prior sample taken from said subject.

5. The method of claim 3, wherein said reference sample is a sample taken from a subject that is pregnant but does not have pre-eclampsia or eclampsia, or a propensity to develop pre-eclampsia or eclampsia.

6. The method of claim 2, further comprising:
   (a) measuring the level of at least one of sFlt-1, free PlGF, and free VEGF polypeptide in a sample from said subject, wherein said VEGF is a VEGF polypeptide that has the ability to bind to sFlt-1 and wherein said free PlGF is a PlGE polypeptide that has the ability to bind to sFlt-1 and wherein said sample is a bodily fluid selected from the group consisting of urine, blood, serum, and plasma; and
   (b) comparing said level of sFlt-1, free PlGF, or free VEGF from said subject sample to the level of sFlt-1, free PlGF, or free VEGF polypeptide in a reference sample, wherein an increase of at least 10% in said level of sFlt-1 or a decrease of at least 10% in said level of free VEGF or free PlGF polypeptide from said subject sample compared to said reference sample is a diagnostic indicator of pre-eclampsia or eclampsia or a propensity to develop pre-eclampsia or eclampsia.

7. The method of claim 6, wherein the level of sFlt-1 from a sample of serum from said subject is measured.

8. The method of claim 6, wherein the level of sFlt-1 and free PlGF from a sample of serum from said subject is measured.

9. The method of claim 6, comprising measuring the level of sFlt-1 and at least one of free VEGF and free PlGF and calculating the relationship between said levels of sFlt-1, and at least one of free VEGF, and free PlGF using a metric, wherein an increase of at least 10% in the level of said sFlt-1 relative to at least one of said free VEGF and free PlGF level in said metric from said subject sample as compared to said metric from a reference sample, diagnoses pre-eclampsia or eclampsia or a propensity to develop pre-eclampsia or eclampsia in said subject.

10. The method of claim 9, wherein said metric comprises a pre-eclampsia anti-angiogenic index (PAAI):[sFlt-1/VEGF+PlGF] and an increase of at least 10% in said PAAI from the subject sample relative to the reference sample diagnoses pre-eclampsia or eclampsia or a propensity to develop pre-eclampsia or eclampsia in said subject.

11. The method of claim 1, 2, or 3, wherein said measuring is done using an immunological assay.

12. The method of claim 11, wherein said immunological assay is an ELISA.

13. A method of diagnosing a pregnant human subject as having a propensity to develop early onset pre-eclampsia or eclampsia, said method comprising
   (a) obtaining a sample of urine from said subject;
   (b) contacting said sample with a solid support, wherein said solid support comprises an immobilized first free PlGF binding agent, for a time sufficient to allow binding of said first free PlGF binding agent with free PlGF present in said sample, wherein said free PlGF is a PlGF polypeptide that has the ability to bind to sFlt-1;
   (c) contacting said solid support after step (b) with a preparation of a second labeled PlGF binding agent, for a time sufficient to allow binding of said second labeled PlGF binding agent to said free PlGF bound to said first immobilized free PlGF binding agent;

(d) measuring the binding of said second labeled PlGF binding agent to the immobilized free PlGF binding agent bound to free PlGF at the position where the first free PlGF binding agent is immobilized;

(e) measuring the level of creatinine in said subject sample;

(f) comparing the binding measured in step (d) with the binding measured using a reference sample, and comparing the level of creatinine measured in step (e) with the level measured using a reference sample wherein a decrease of at least 50% in the binding measured in step (d) for said sample, as compared to the binding measured using a reference sample, when normalized for said creatinine levels measured in step (e) is a diagnostic indicator of a propensity to develop early onset pre-eclampsia or eclampsia.

14. The method of claim 13, wherein said reference sample is recombinant PlGF at a concentration of 400 to 800 pg/ml.

15. The method of claim 13, wherein said second labeled PlGF binding agent comprises a colorimetric label or a fluorescent label.

16. The method of claim 13, wherein said free PlGF binding agent is an antibody, or purified fragment thereof, or a peptide.

17. A method of diagnosing a pregnant human subject as having a propensity to develop early onset pre-eclampsia or eclampsia, said method comprising:

(a) obtaining a sample of urine from said subject;

(b) contacting said sample with a solid support, wherein said solid support comprises an immobilized free PlGF binding agent that is detectably labeled, wherein said contacting is for a time sufficient to allow binding of said first PlGF binding agent to free PlGF present in said sample, wherein said free PlGF is a PlGF polypeptide that has the ability to bind to sFlt-1;

(c) measuring said labeled free PlGF binding agent bound to said free PlGF, wherein said measuring is capable of distinguishing between said bound and unbound PlGF binding agent;

(d) measuring the level of creatinine in said subject sample; and (e) comparing the binding measured in step (c) with the binding measured using a reference sample, and comparing the level of creatinine measured in step (d) with the level measured using a reference sample, wherein a decrease of at least 50% in the binding measured in step (c) for said sample, as compared to the binding measured using a reference sample, when normalized for said creatinine levels measured in step (d) is a diagnostic indicator of a propensity to develop early onset pre-eclampsia or eclampsia.

18. The method of claim 17, wherein the free PlGF binding agent comprises a fluorescent label or a colorimetric label.

19. The method of claim 13 or 17, wherein said solid support is a membrane.

20. The method of claim 3, 13, or 17, further comprising measuring the level of sFlt-1, free PlGF, or free VEGF polypeptide, in a sample of bodily fluid from said subject, wherein said free VEGF is a VEGF polypeptide that has the ability to bind to sFlt-1 and wherein said free PlGF is a PlGF polypeptide that has the ability to bind to sFlt-1, and wherein said bodily fluid is selected from the group consisting of urine, blood, serum, and plasma, wherein an increase of at least 50% in the level of said sFlt-1 or a decrease of at least 50% in the level of said free PlGF or free VEGF diagnoses said subject with a propensity to develop early onset pre-eclampsia or eclampsia.

21. The method of claim 20, wherein said level of sFlt-1 polypeptide is measured in a sample of serum from said subject.

22. The method of claim 13 or 17, wherein said reference sample is a prior sample from said subject and a decrease of at least 50% in said levels of free PlGF, when normalized for said creatinine levels, over time is a diagnostic indicator of a propensity to develop early onset pre-eclampsia or eclampsia.

23. The method of claim 1, 2, 3, or 6, further comprising determining the body mass index or gestational age for said pregnant human subject.

24. The method of claim 13, or 17, wherein said pregnant human subject is in the second trimester of pregnancy.

25. The method of claim 13, or 17, wherein said pregnant human subject is 21 to 32 weeks pregnant.

26. The method of claim 2, further comprising:

(a) measuring the levels of sFlt-1, free VEGF, and free PlGF polypeptides in a sample from a human subject, wherein said free VEGF is a VEGF polypeptide that has the ability to bind to sFlt-1 and wherein said free PlGF is a PlGF polypeptide that has the ability to bind to sFlt-1 and wherein said sample is a bodily fluid selected from the group consisting of urine, blood, serum, and plasma; and (b) calculating the relationship between said levels of sFlt-1, free VEGF, and free PlGF using a PAAI metric, wherein a PAAI value greater than or equal to 20 is a diagnostic indicator of pre-eclampsia or eclampsia.

27. The method of claim 6, wherein said reference sample is a prior sample taken from said subject.

28. The method of claim 27, wherein said reference sample is taken during the first trimester of pregnancy.

29. The method of claim 6, wherein said reference sample is a sample taken from a subject that is pregnant but does not have pre-eclampsia or eclampsia, or a propensity to develop pre-eclampsia or eclampsia.

30. The method of claim 9, wherein said metric is sFlt-1/PlGF.

31. The method of claim 22, wherein the prior sample is taken during the first trimester of pregnancy and the subject sample is taken during the second or third trimester of pregnancy.

32. The method of claim 13 or 17, wherein the reference sample is PlGF ranging from 10 pg/ml to 1 ng/ml and a decrease of at least 50% in the binding measured in the subject sample, when normalized to said creatinine levels, compared to the binding measured using the reference sample is a diagnostic indicator of a propensity to develop early onset pre-eclampsia or eclampsia.

33. The method of claim 19, wherein said membrane is supported on a dipstick structure and the sample is deposited on the membrane by placing the dipstick structure into the sample.

34. The method of claim 4, wherein said prior sample is a sample taken during the first trimester of pregnancy.

35. The method of claim 6, 7, 8, or 21, wherein said sFlt-1 is the level of free sFlt-1.

36. The method of claim 6, wherein said sFlt-1 is the level of bound sFlt-1.

37. The method of claim 6, wherein said sFlt-1 is the level of total sFlt-1.

38. The method of claim 10, wherein an increase of at least 90% in said PAAI from said subject sample relative to the reference sample diagnoses pre-eclampsia or eclampsia or a propensity to develop pre-eclampsia or eclampsia in said subject.

39. The method of claim 6, wherein an increase of at least 50% in the level of sFlt-1 or a decrease of at least 50% in the level of free VEGF or free PlGF polypeptide relative to said reference diagnoses said subject as having a propensity to develop early onset pre-eclampsia or eclampsia.

40. The method of claim 9, wherein an increase of at least 50% in the level of said sFlt-1 relative to at least one of said free VEGF and free PlGF level in said metric from said subject sample as compared to said metric from said reference sample diagnoses said subject as having a propensity to develop, pre-eclampsia or eclampsia.

41. The method of claim 11, wherein said immunological assay comprises an antibody, or purified fragment thereof, that specifically binds to the sFlt-1 binding domain of PlGF.

42. The method of claim 17, wherein said free PlGF binding agent is an antibody, or purified fragment thereof, or a peptide.

43. The method of claim 16 or 42, wherein said antibody, or purified fragment thereof, specifically binds to the sFlt-1 binding domain of PlGF.

44. A method of diagnosing a pregnant human subject as having a propensity to develop early onset pre-eclampsia or eclampsia, said method comprising measuring the level of free PlGF in a urine sample from said pregnant human subject, wherein the subject is in the first or second trimester of pregnancy, and wherein said free PlGF is a PlGF polypeptide that has the ability to bind to sFlt-1, and comparing said level of free PlGF from said subject to the level of free PlGF from a reference sample, wherein a decrease of at least 50% in said free PlGF from the subject sample compared to said reference sample is a diagnostic indicator of a propensity to develop early onset pre-eclampsia or eclampsia.

45. A method of diagnosing a pregnant human subject as having or having a propensity to develop pre-eclampsia or eclampsia, said method comprising measuring the level of free PlGF in a urine sample from said pregnant human subject and measuring the level of sFlt-1 in a bodily fluid sample from said pregnant human subject, wherein said free PlGF is a PlGF polypeptide that has the ability to bind to sFlt-1, and comparing said level of free PlGF and said sFlt-1 from said subject to the level of free PlGF and said sFlt-1 from a reference sample, wherein a decrease of at least 10% in said free PlGF and an increase of at least 10% in said sFlt-1 from the subject sample compared to said reference sample is a diagnostic indicator of a pre-eclampsia or eclampsia or a propensity to develop pre-eclampsia or eclampsia.

46. A method of diagnosing a pregnant human subject as having a propensity to develop pre-eclampsia or eclampsia, said method comprising
(a) obtaining a sample of urine from said subject, wherein said subject is less than 16 weeks pregnant;
(b) contacting said sample with a solid support, wherein said solid support comprises an immobilized first free PlGF binding agent, for a time sufficient to allow binding of said first free PlGF binding agent with free PlGF present in said sample, wherein said free PlGF is a PlGF polypeptide that has the ability to bind to sFlt-1;
(c) contacting said solid support after step (b) with a preparation of a second labeled PlGF binding agent, for a time sufficient to allow binding of said second labeled PlGF binding agent to said free PlGF bound to said first immobilized free PlGF binding agent;
(d) measuring the binding of said second labeled PlGF binding agent to the immobilized free PlGF binding agent bound to free PlGF at the position where the first free PlGF binding agent is immobilized; and
(e) comparing the binding measured in step (d) with the binding measured using a reference sample, wherein a decrease of at least 10% in the binding measured in step (d) for said sample, as compared to the binding measured using a reference sample is a diagnostic indicator of pre-eclampsia or eclampsia or a propensity to develop pre-eclampsia or eclampsia.

47. A method of diagnosing a pregnant human subject as having or having a propensity to develop pre-eclampsia or eclampsia, said method comprising:
(a) obtaining a sample of urine from said subject, wherein said subject is less than 16 weeks pregnant;
(b) contacting said sample with a solid support, wherein said solid support comprises an immobilized free PlGF binding agent that is detectably labeled, wherein said contacting is for a time sufficient to allow binding of said first PlGF binding agent to free PlGF present in said sample, wherein said free PlGF is a PlGF polypeptide that has the ability to bind to sFlt-1;
(c) measuring said labeled free PlGF binding agent bound to said free PlGF, wherein said measuring is capable of distinguishing between said bound and unbound PlGF binding agent; and
(d) comparing the binding measured in step (c) with the binding measured using a reference sample,
wherein a decrease of at least 10% in the binding measured in step (d) for said sample, as compared to the binding measured using a reference sample is a diagnostic indicator of pre-eclampsia or eclampsia or a propensity to develop pre-eclampsia or eclampsia.

48. The method of claim 13 or 17, wherein the reference sample is PlGF ranging from 10 pg/ml to 1 ng/ml and wherein a binding observed in step (d) that is equal to or less than the binding observed for 200 pg/ml of PlGF, when normalized for creatinine levels, is a diagnostic indicator of a propensity to develop early onset pre-eclampsia or eclampsia.

49. The method of claim 45, 46, or 47, wherein a decrease of at least 50% diagnoses said pregnant human subject as having a propensity to develop early onset pre-eclampsia or eclampsia.

50. The method of claim 1, 2, 6, 7, 24, 25, or 30, wherein the method diagnoses said pregnant human subject as having a propensity to develop pre-eclampsia or eclampsia.

51. The method of claim 1, 2, 6, 7, 24, 25, or 30, wherein the method diagnoses said pregnant human subject as having pre-eclampsia or eclampsia.

52. The method of claim 30, wherein the subject is 21-32 weeks pregnant and an increase of at least 50% in the level of sFlt-1/PlGF diagnoses the subject as having a propensity to develop early onset pre-eclampsia or eclampsia.

53. The method of claim 39 or 40, wherein said subject is 21-32 weeks pregnant and the method diagnoses the pregnant human subject as having a propensity to develop early onset pre-eclampsia.

54. The method of claim 6 or 26, wherein said VEGF polypeptide is selected from the group consisting of VEGF-A, VEGF-B, VEGF189, VEGF165, and VEGF121.

55. The method of claim 1, 2, 3, 13, 17, or 44, wherein said PlGF polypeptide is an alternatively spliced isoform of PlGF.

56. The method of claim 45, wherein said sFlt-1 is free or total sFlt-1.

* * * * *

UNITED STATES PATENT AND TRADEMARK OFFICE
CERTIFICATE OF CORRECTION

PATENT NO. : 7,435,419 B2
APPLICATION NO. : 11/019559
DATED : October 14, 2008
INVENTOR(S) : Karumanchi et al.

It is certified that error appears in the above-identified patent and that said Letters Patent is hereby corrected as shown below:

Title Page; item (56);

On Page 2, Under Other Publications,
 replace "Charnock-Jones et al., Determination of the Circulating" with --Charnock-Jones et al., Determination of the Circulating--.
 replace "Charnock-Jones et al., Identification and Localization" with --Charnock-Jones et al., Identification and Localization--.
 Under Knebelmann et al., replace "Supressor" with --Suppressor--.
 Under Lai et al., replace "Neovascularisation" with --Neovascularization--.

On Page 4, Under Other Publications,
 Under Krussel et al., replace "soluable" with --soluble--.
 Under Lyall et al., replace "pre-eclamsia" with --pre-eclampsia--.

Column 1, Line 29, replace "ing" with --testing--.

Column 5, Line 23, replace "P-galactosidase" with --β-galactosidase--.

Column 30, Line 44, replace "pre-eclampsia 5(OR 5.1, 95 percent" with --pre-eclampsia (OR 5.1, 95 percent--.

Column 45,
 Line 7, replace "included the diagnostic metric" with --included in the diagnostic metric--.
 Line 37, replace "can be as a diagnostic" with --can be used as a diagnostic--.

Signed and Sealed this

First Day of June, 2010

David J. Kappos
*Director of the United States Patent and Trademark Office*

Column 47, Line 64, replace "#DPG000" with --#DPG00--.